(12) United States Patent
Hughes et al.

(10) Patent No.: US 7,674,936 B2
(45) Date of Patent: Mar. 9, 2010

(54) ORTHO-SUBSTITUTED ARYL AMIDES FOR CONTROLLING INVERTEBRATE PESTS

(75) Inventors: Kenneth Andrew Hughes, Rising Sun, MD (US); George Philip Lahm, Wilmington, DE (US); Thomas Paul Selby, Hockessin, DE (US); Benjamin Kenneth Smith, Newark, DE (US); William Thomas Zimmerman, Landenberg, PA (US)

(73) Assignee: E.I. du Pont De Nemours and Company, Wilmington, DE (US)

( * ) Notice: Subject to any disclaimer, the term of this patent is extended or adjusted under 35 U.S.C. 154(b) by 77 days.

(21) Appl. No.: 11/803,170

(22) Filed: May 11, 2007

(65) Prior Publication Data

US 2007/0249832 A1    Oct. 25, 2007

Related U.S. Application Data

(62) Division of application No. 10/483,118, filed as application No. PCT/US02/26959 on Aug. 13, 2002, now Pat. No. 7,288,554.

(60) Provisional application No. 60/312,423, filed on Aug. 15, 2001.

(51) Int. Cl.
    *C07C 211/00* (2006.01)
(52) U.S. Cl. ....................... 564/342; 564/345
(58) Field of Classification Search ................. 564/305
    See application file for complete search history.

(56) References Cited

U.S. PATENT DOCUMENTS

| 3,840,540 A | 10/1974 | Dominy et al. |
| 4,137,325 A | 1/1979 | Sellstedt et al. |
| 4,175,184 A | 11/1979 | Merkle et al. |
| 6,747,047 B2 * | 6/2004 | Lahm et al. .................. 514/341 |
| 2003/0229050 A1 * | 12/2003 | Lahm et al. .................... 514/63 |
| 2005/0075372 A1 | 4/2005 | Lahm et al. |
| 2005/0124600 A1 | 6/2005 | Clark et al. |

FOREIGN PATENT DOCUMENTS

| DE | 1543332 | 8/1969 |
| DE | 2710382 | 12/1983 |
| GB | 1178322 | 1/1970 |
| IT | 869213 | 8/1970 |
| NL | 6603319 | 9/1967 |
| WO | WO 99/32433 | 7/1999 |
| WO | WO 00/69823 | 11/2000 |
| WO | WO 01/56989 | 8/2001 |

OTHER PUBLICATIONS

Hcaplus 1948:8767, "6,8-Diiodobenzoyleneurea, and the interaction of 5,7-dihaloisatoic anhydrides with ammonia and with ethylamine. 3-Ethyl-6,8-dihalobenzoyleneureas" Sheibley, Fred E., 1047.*
Peter H. Gore et al., "Friedel-Crafts Reactions. Part XXV. Acetylation and Benzoylation of Iodobenzene and of o-, m-, and p-Iodotoluenes", J.C.S. Perkin I, 1973, 2940-2948.
Milton J. Kornet, "Synthesis and Anticonvulsant Activity of 3-Alkyl-3,4-dihydro-2(1H)-quinazolinones", J. Heterocyclic Chem., 1992, 103-105, 29.
Fred E. Sheibley, "6,8-Diiodobenzoyleneurea, and the Interaction of 5,7-Dihalogenoisatoic Anhydrides with Ammonia and with Ethyleamine. 3-Ethyl-6,8-dihalogenobenzoyleneureas", J. Org. Chem, 1947, 743-751, 12.

* cited by examiner

*Primary Examiner*—Janet L Andres
*Assistant Examiner*—Binta M Robinson

(57) ABSTRACT

Disclosed are compounds of Formula I, their N-oxides and agriculturally suitable salts

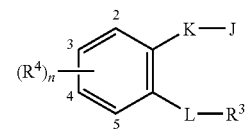

wherein
  J is a phenyl ring, a 5- or 6-membered heteroaromatic ring or an aromatic 8-, 9- or 10-membered fused carbobicyclic or heterobicyclic ring system wherein each ring or ring system is substituted with from one to four substituents independently selected from $R^5$;
  K is $-NR^1C(=A)-$, $-N=C(GR^6)-$ or $-NR^1SO_2-$;
  L is $-C(=B)NR^2-$, $-C(GR^6)=N-$, $-SO_2NR^2-$, $-C(=B)O-$ or $-C(=B)-$; and
  A, B, G, $R^1$, $R^2$, $R^3$, $R^4$, $R^5$, $R^6$ and n are as defined in the disclosure.

Also disclosed are methods for controlling invertebrate pests comprising contacting the pests or their environment with a biologically effective amount of a compound of Formula I and compositions containing the compounds of Formula I. Intermediate compounds useful in preparing the compounds of Formula I are also disclosed.

3 Claims, No Drawings

ORTHO-SUBSTITUTED ARYL AMIDES FOR CONTROLLING INVERTEBRATE PESTS

BACKGROUND OF THE INVENTION

This invention relates to certain ortho-substituted aryl amides, their N-oxides, salts and compositions suitable for agronomic and nonagronomic uses, including those listed below, and methods of their use for controlling invertebrate pests in both agronomic and nonagronomic environments.

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

NL 9202078 discloses N-acyl anthranilic acid derivatives of Formula i as insecticides

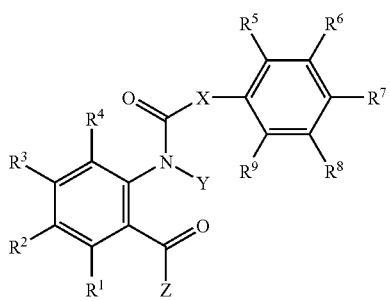

wherein, inter alia, X is a direct bond; Y is H or $C_1$-$C_6$ alkyl; Z is $NH_2$, $NH(C_1$-$C_3$ alkyl) or $N(C_1$-$C_3$ alkyl)$_2$; and $R^1$ through $R^9$ are independently H, halogen, $C_1$-$C_6$ alkyl, phenyl, hydroxy, $C_1$-$C_6$ alkoxy or $C_1$-$C_7$ acyloxy.

SUMMARY OF THE INVENTION

This invention pertains to compounds of Formula I, and N-oxides and salts thereof

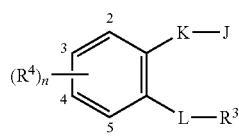

wherein
  J is a phenyl ring, a 5- or 6-membered heteroaromatic ring or an aromatic 8-, 9- or 10-membered fused carbobicyclic or heterobicyclic ring system wherein each ring or ring system is substituted with from one to four substituents independently selected from $R^5$;
  K is —$NR^1C(=A)$-, —$N=C(GR^6)$— or —$NR^1SO_2$—;
  L is —$C(=B)NR^2$—, —$C(GR^6)=N$—, —$SO_2NR^2$—, —$C(=B)O$— or —$C(=B)$—;

A and B are independently O, S, $NR^8$, $NOR^8$, $NN(R^8)_2$, S=O, N—CN or N—$NO_2$;
each G is independently O, S or $NR^8$;
$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents independently selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or
$R^1$ is $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl;
$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;
$R^3$ is H; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl or $C_2$-$C_6$ alkylcarbonyl; or $C_1$-$C_6$ alkyl, $C_2$-$C_6$ alkenyl, $C_2$-$C_6$ alkynyl or $C_3$-$C_6$ cycloalkyl, each optionally substituted with one or more substituents independently selected from the group consisting of halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, and a phenyl, phenoxy or 5- or 6-membered heteroaromatic ring, each ring optionally substituted with from one to three substituents independently selected from $R^9$; or
$R^2$ and $R^3$ can be taken together with the nitrogen to which they are attached to form a ring containing 2 to 6 atoms of carbon and optionally one additional atom selected from the group consisting of nitrogen, sulfur and oxygen, said ring optionally substituted with from one to four substituents independently selected from the group consisting of $C_1$-$C_2$ alkyl, halogen, CN, $NO_2$ and $C_1$-$C_2$ alkoxy;
each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, or $C_3$-$C_6$ trialkylsilyl; or
each $R^4$ is independently a phenyl, benzyl or phenoxy ring, each ring optionally substituted with from one to three substituents independently selected from $R^9$;
each $R^5$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl; or
each $R^5$ is independently a phenyl, benzyl, benzoyl, phenoxy or 5- or 6-membered heteroaromatic ring, or an aromatic 8-, 9- or 10-membered fused heterobicyclic ring system, each ring or ring system optionally substituted with from one to three substituents independently selected from $R^9$; or ($R^5$)$_2$ when attached to adjacent carbon atoms can be taken together as —OCF$_2$O—, —CF$_2$CF$_2$O— or —OCF$_2$CF$_2$O—;

each $R^6$ is independently C$_1$-C$_6$ alkyl, C$_2$-C$_6$ alkenyl, C$_2$-C$_6$ alkynyl, each optionally substituted with one or more substituents independently selected from the group consisting of halogen, CN, C$_1$-C$_4$ alkoxy, C$_2$-C$_6$ alkoxyalkoxy, C$_1$-C$_4$ alkylthio, (C$_3$-C$_6$ trialkylsilyl)C$_1$-C$_2$ alkoxy or $R^7$; C$_3$-C$_6$ cycloalkyl; C$_2$-C$_6$ alkylcarbonyl; C$_2$-C$_6$ alkoxycarbonyl; C$_2$-C$_6$ alkylaminocarbonyl; C$_3$-C$_8$ dialkylaminocarbonyl; C$_1$-C$_4$ alkylsulfonyl; C$_1$-C$_4$ haloalkylsulfonyl or C$_3$-C$_9$ trialkylsilyl; or each $R^6$ is independently a phenyl ring or a 5- or 6-membered heteroaromatic ring, each ring optionally substituted with from one to three substituents independently selected from $R^9$;

each $R^7$ is independently a phenyl, benzyloxy or 5- or 6-membered heteroaromatic ring, each ring optionally substituted with from one to three substituents independently selected from $R^9$;

each $R^8$ is independently H; C$_1$-C$_6$ alkyl, C$_2$-C$_6$ alkenyl, C$_2$-C$_6$ alkynyl, each optionally substituted with one or more substituents independently selected from the group consisting of halogen, CN, C$_1$-C$_4$ alkoxy, C$_1$-C$_4$ alkylthio or $R^7$; C$_3$-C$_6$ cycloalkyl; C$_2$-C$_6$ alkylcarbonyl; C$_2$-C$_6$ alkoxycarbonyl; C$_2$-C$_6$ alkylaminocarbonyl; C$_3$-C$_8$ dialkylaminocarbonyl or C$_3$-C$_9$ trialkylsilyl; or each $R^9$ is independently a phenyl ring or a 5- or 6-membered heteroaromatic ring, each ring optionally substituted with from one to three substituents independently selected from $R^9$;

each $R^9$ is independently C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_2$-C$_4$ haloalkenyl, C$_2$-C$_4$ haloalkynyl, C$_3$-C$_6$ halocycloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_6$ cycloalkylamino, C$_4$-C$_8$ (alkyl)cycloalkylamino, C$_2$-C$_4$ alkylcarbonyl, C$_2$-C$_6$ alkoxycarbonyl, C$_2$-C$_6$ alkylaminocarbonyl, C$_3$-C$_8$ dialkylaminocarbonyl or C$_3$-C$_6$ trialkylsilyl; and n is 1 to 4;

provided that when K is —NR$^1$C(=A)- and A is O or S, then L is other than —C(=O)NR$^2$— or —C(=S)NR$^2$—.

This invention also pertains to a method for controlling an invertebrate pest comprising contacting the invertebrate pest or its environment with a biologically effective amount of a compound of Formula I, an N-oxide thereof or a suitable salt of the compound (e.g., as a composition described herein). This invention also relates to such a method wherein the invertebrate pest or its environment is contacted with a biologically effective amount of a compound of Formula I, an N-oxide thereof or a suitable salt thereof, or a composition comprising the compound, N-oxide thereof or a suitable salt thereof and a biologically effective amount of at least one additional compound or agent for controlling an invertebrate pest.

This invention also pertains to a composition for controlling an invertebrate pest comprising a biologically effective amount of a compound of Formula I, an N-oxide thereof or a suitable salt of the compound and at least one additional component selected from the group consisting of surfactants, solid diluents and liquid diluents. This invention also pertains to a composition comprising a biologically effective amount of a compound of Formula I, an N-oxide thereof or a suitable salt of the compound and an effective amount of at least one additional biologically active compound or agent.

DETAILS OF THE INVENTION

In the above recitations, "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Cycloalkyl" includes, for example, cyclopropyl, cyclobutyl, cyclopentyl and cyclohexyl. "Trialkylsilyl" includes (CH$_3$)$_3$Si, (CH$_3$CH$_2$)$_3$Si and [(CH$_3$)$_3$C](CH$_3$)$_2$Si.

The term "aromatic" indicates that each of the ring atoms is essentially in the same plane and has a p-orbital perpendicular to the ring plane, and in which (4n+2) π electrons, when n is 0 or a positive integer, are associated with the ring to comply with Hückel's rule. The term "aromatic ring system" denotes fully unsaturated carbocycles and heterocycles in which at least one ring of a polycyclic ring system is aromatic. Aromatic carbocyclic rings or fused carbobicyclic ring systems includes fully aromatic carbocycles and carbocycles in which at least one ring of a polycyclic ring system is aromatic (e.g. phenyl, naphthyl and 1,2,3,4-tetrahydro-naphthyl). The term "nonaromatic carbocyclic ring" denotes fully saturated carbocycles as well as partially or fully unsaturated carbocycles where the Hückel rule is not satisfied by the ring. The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ling or ring system" and "aromatic fused heterobicyclic ring system" includes fully aromatic heterocycles and heterocycles in which at least one ring of a polycyclic ring system is aromatic (where aromatic indicates that the Hückel rule is satisfied). The term "nonaromatic heterocyclic ring or ring system" denotes fully saturated heterocycles as well as partially or fully unsaturated heterocycles where the Hückel rule is not satisfied by any of the rings in the ring system. The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The terms "haloalkenyl", "haloalkynyl", "haloalkoxy", and the like, are defined analogously to the term "haloalkyl". Examples of "haloalkenyl" include (Cl)$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O.

Examples of "alkylcarbonyl" include C(O)CH$_3$, C(O)CH$_2$CH$_2$CH$_3$ and C(O)CH(CH$_3$)$_2$. Examples of "alkoxycarbonyl" include CH$_3$OC(=O), CH$_3$CH$_2$OC(=O), CH$_3$CH$_2$CH$_2$OC(=O), (CH$_3$)$_2$CHOC(=O) and the different butoxy- or pentoxycarbonyl isomers. Examples of "alkylaminocarbonyl" include CH$_3$NHC(=O), CH$_3$CH$_2$NHC(=O), CH$_3$CH$_2$CH$_2$NHC(=O), (CH$_3$)$_2$CHNHC(=O) and the different butylamino- or pentylaminocarbonyl isomers. Examples of "dialkylaminocarbonyl" include (CH$_3$)$_2$NC(=O), (CH$_3$CH$_2$)$_2$NC(=O), CH$_3$CH$_2$(CH$_3$)NC(=O), CH$_3$CH$_2$CH$_2$(CH$_3$)NC(=O) and (CH$_3$)$_2$CHN(CH3)C(=O).

The total number of carbon atoms in a substituent group is indicated by the "$C_i$-$C_j$" prefix where i and j are integers from 1 to 8. For example, $C_1$-$C_3$ alkylsulfonyl designates methylsulfonyl through propylsulfonyl; $C_2$ alkoxyalkyl designates CH$_3$OCH$_2$; $C_3$ alkoxyalkyl designates, for example, CH$_3$CH(OCH$_3$), CH$_3$OCH$_2$CH$_2$ or CH$_3$CH$_2$OCH$_2$; and $C_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$.

In the above recitations, when a compound of Formula I contains a heterocyclic ring, all substituents are attached to this ring through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. (R)$_{i-j}$, then the number of substituents may be selected from the integers between i and j inclusive.

The term "optionally substituted" indicates that the group is either unsubstituted or substituted. The term "optionally substituted with from one to three substituents" and the like indicates that from one to three of the available positions on the group may be substituted. When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form. Some compounds of this invention can exist as one or more tautomers, and all tautomeric forms of such compounds are part of the present invention. Accordingly, the compounds of the invention may be present as a mixture of tautomers or the individual tautomers.

The present invention comprises compounds selected from Formula I, N-oxides and suitable salts thereof. One skilled in the art will appreciate that not all nitrogen containing heterocycles can form N-oxides since the nitrogen requires an available lone pair of electrons for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, Vol. 3, pp 18-19, A. J. Boulton and A. McKillop, Eds., Pergamon Press; M. R. Grimmett and B. R. T. Keene in *Advances in Heterocyclic Chemistry*, Vol. 43, pp 139-151, A. R. Katritzky, Ed., Academic Press; M. Tisler and B. Stanovnik in *Advances in Heterocyclic Chemistry*, Vol. 9, pp 285-291, A. R. Katritzky and A. J. Boulton, Eds., Academic Press; and G. W. H. Cheeseman and E. S. G. Werstiuk in *Advances in Heterocyclic Chemistry*, Vol. 22, pp 390-392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group such as a carboxylic acid or phenol.

As noted above, each J is independently a phenyl ring, a 5- or 6-membered heteroaromatic ring or an aromatic 8-, 9- or 10-membered fused carbobicyclic or heterobicyclic ring system, wherein each ring or ring system is substituted with from one to four $R^5$. An example of phenyl substituted with from one to four $R^5$ is the ring illustrated as U-1 in Exhibit 1 below, wherein $R^v$ is $R^5$ and r is an integer from 1 to 4. Examples of aromatic 8-, 9- or 10-membered fused carbobicyclic ring system substituted with from one to four $R^5$ include a naphthyl group illustrated as U-85 in Exhibit 1 and a 1,2,3,4-tetrahydronaphthyl group illustrated as U-89 in Exhibit 1, wherein $R^v$ is $R^3$ and r is an integer from 1 to 4. Examples of 5- or 6-membered heteroaromatic rings substituted with from one to four $R^5$ include the rings U-2 through U-53 illustrated in Exhibit 1 wherein $R^v$ is $R^5$ and r is an integer from 1 to 4. Note that J-1 through J-4 below also denote 5- or 6-membered heteroaromatic rings. Note that U-2 through U-20 are examples of J-1, U-21 through U-35 and U-40 are examples of J-2, U-41 through U-48 are examples of J-3 and U-49 through U-53 are examples of J-4. Examples of aromatic 8-, 9- or 10-membered fused heterobicyclic ring systems substituted with from one to four $R^5$ include U-54 through U-84 illustrated in Exhibit 1 wherein $R^v$ is $R^5$ and r is an integer from 1 to 4.

Although $R^v$ groups are shown in the structures U-1 through U-90, it is noted that when they are optional substituents they do not need to be present. Note that when $R^v$ is H when attached to an atom, this is the same as if said atom is unsubstituted. The nitrogen atoms that require substitution to fill their valence are substituted with H or $R^v$. Note that some U groups can only be substituted with less than 4 $R^v$ groups (e.g. U-14, U-15, U-18 through U-21 and U-32 through U-34 can only be substituted with one $R^v$). Note that when the attachment point between (R$^v$)$_r$ and the U group is illustrated as floating, (R$^v$)$_r$ can be attached to any available carbon atom of the U group. Note that when the attachment point on the U group is illustrated as floating, the U group can be attached to the remainder of Formula I through any available carbon of the U group by replacement of a hydrogen atom.
Exhibit 1
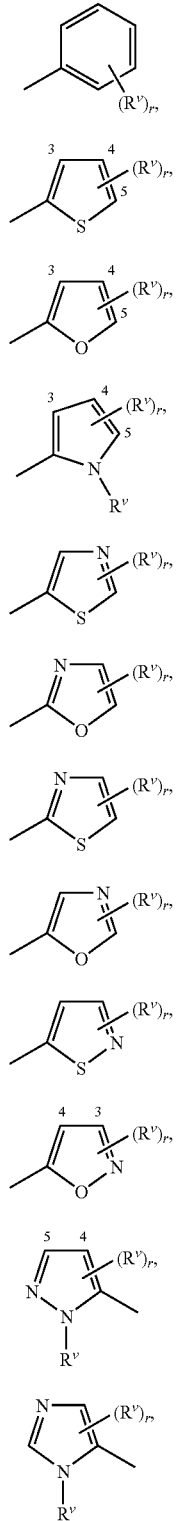
U-1, U-2, U-3, U-4, U-5, U-6, U-7, U-8, U-9, U-10, U-11, U-12
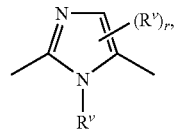
U-13
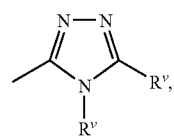
U-14
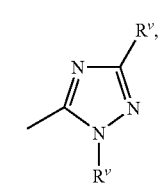
U-15
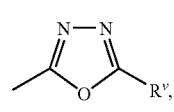
U-16
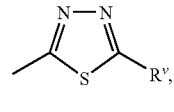
U-17
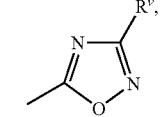
U-18
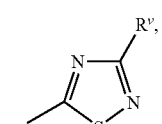
U-19
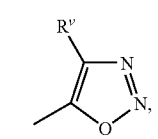
U-20
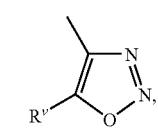
U-21
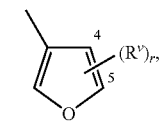
U-22
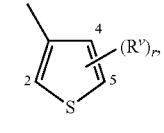
U-23

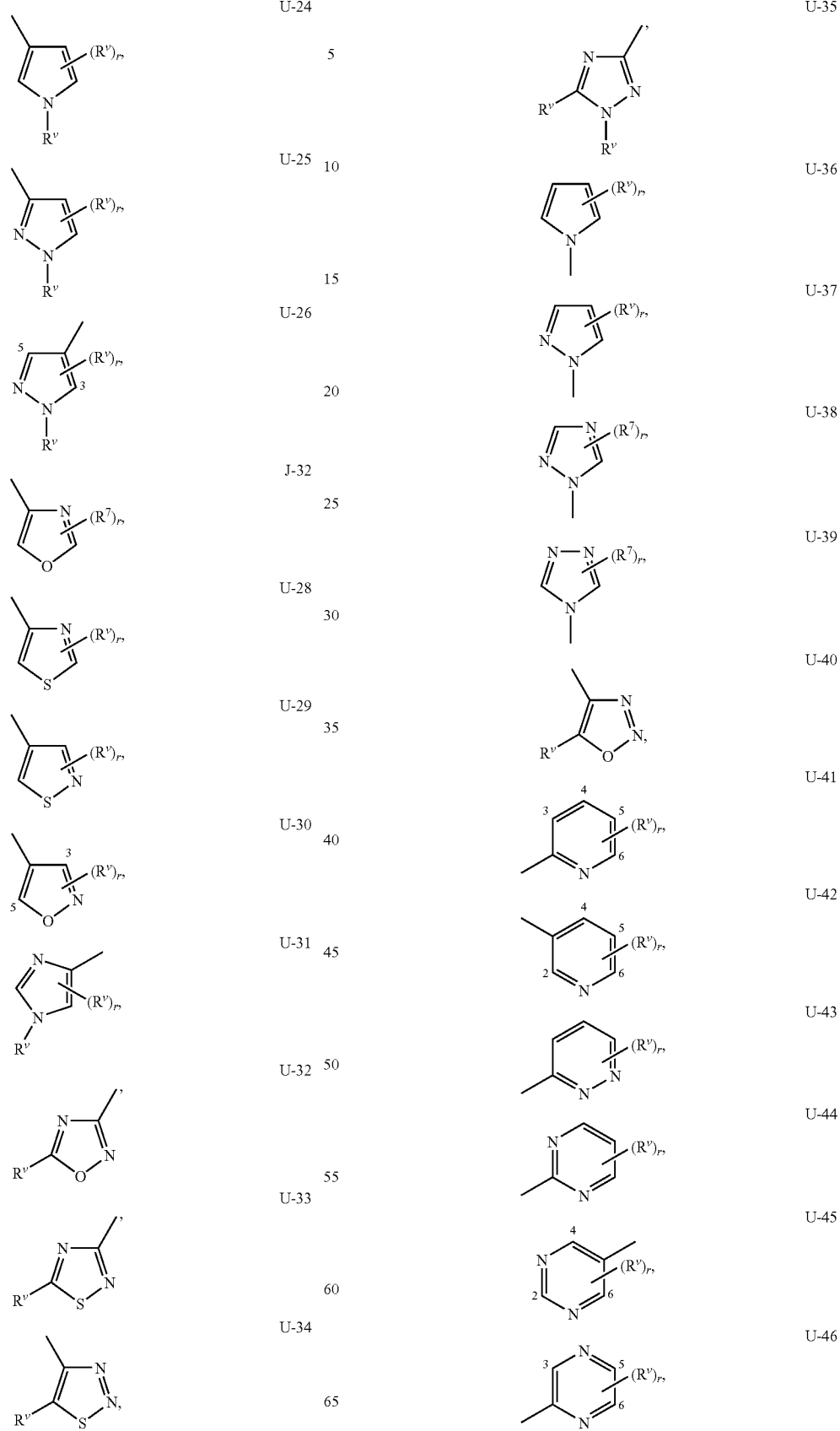

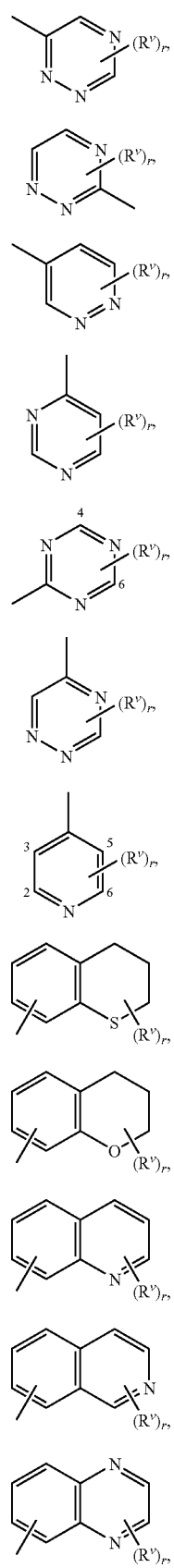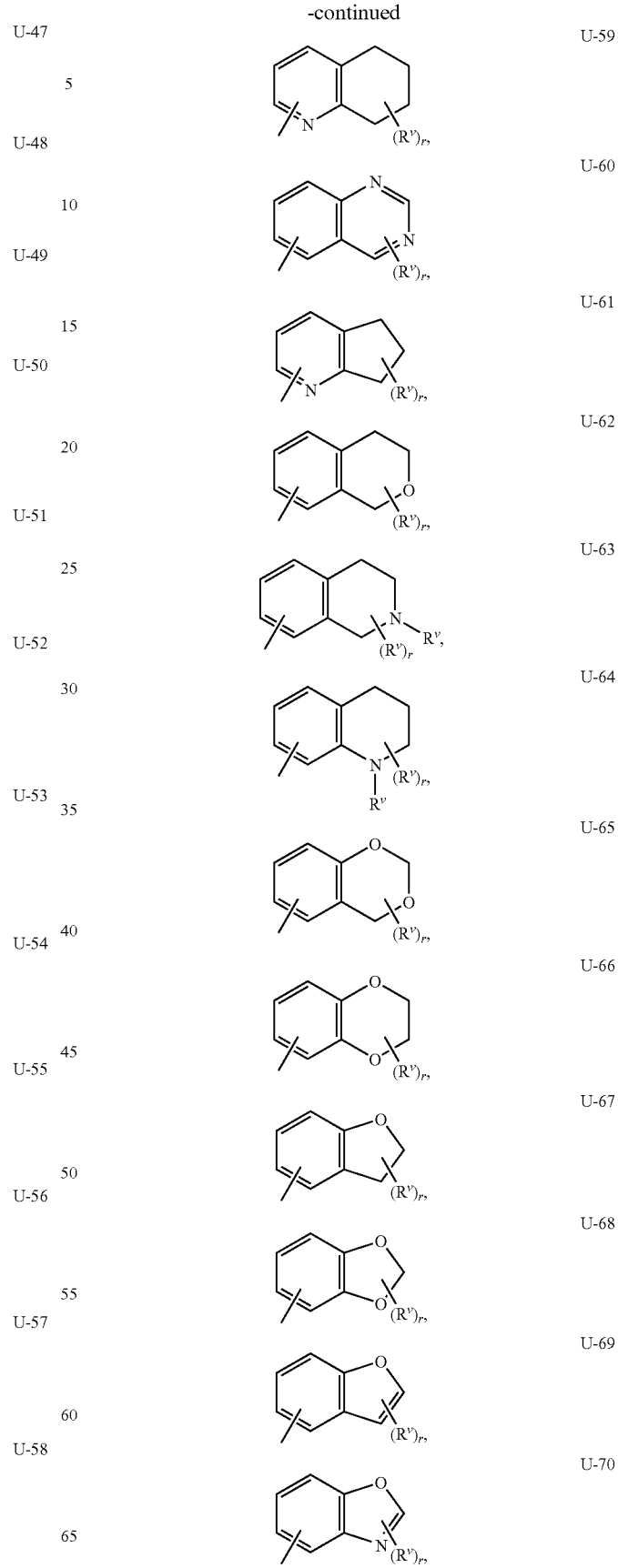

-continued

U-71 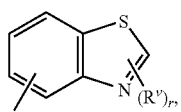

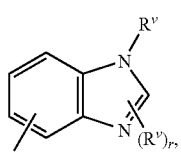

U-72

U-73 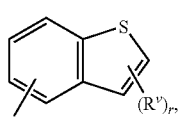

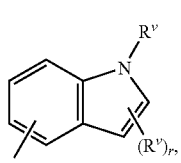

U-74

U-75 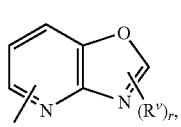

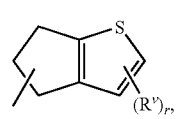

U-76

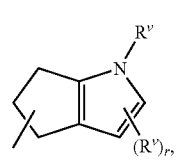

U-77

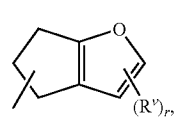

U-78

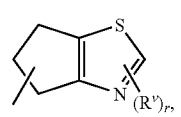

U-79

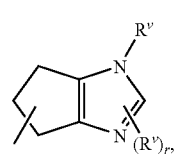

U-80

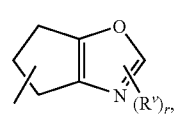

U-81

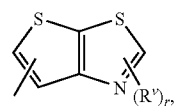

U-82

-continued

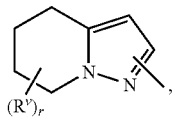 U-83

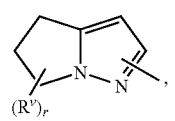 U-84

U-85

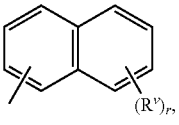

U-86

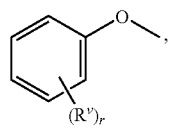

U-87

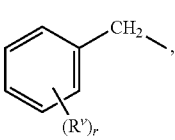

U-88

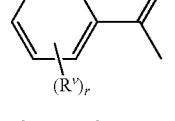

U-89

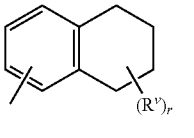 or

U-90

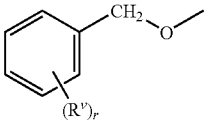

As noted above, certain $R^1$, $R^3$, $R^6$ and $R^8$ groups can be optionally substituted with one or more substituents. The term "optionally substituted" in connection with these $R^w$ groups (wherein w is 1, 3, 6 or 8) refers to R groups that are unsubstituted or have at least one non-hydrogen substituent. Examples of optionally substituted $R^w$ groups are those that are optionally substituted by replacement of a hydrogen on a carbon atom of the $R^w$ group with one or more (up to the total number of hydrogens available for replacement in any specific $R^w$ group) substituents independently selected from the substituents listed in the Summary of the Invention above. Although these substituents are listed, it is noted that they do not need to be present since they are optional substituents. Of particular note are $R^w$ groups that are unsubstituted. Of note are $R^v$ groups substituted with from one to five substituents. Also of note are $R^w$ groups substituted with one substituent.

As noted above, $R^3$ can be $C_1$-$C_6$ alkyl, $C_2$-$C_6$ alkenyl, $C_2$-$C_6$ alkynyl or $C_3$-$C_6$ cycloalkyl each optionally substituted with (among others) a phenyl, phenoxy or 5- or 6-membered heteroaromatic ring, each ring optionally substituted with from one to three substituents independently selected from $R^9$. Examples of such substituent rings include the rings illustrated as rings U-1 (phenyl), U-2 through U-53 (5- or 6-membered heteroaromatic rings) and U-86 (phenoxy) illustrated in Exhibit 1 above, wherein $R^v$ is $R^9$ and r is an integer from 1 to 3.

As noted above, each $R^4$ can be independently (among others) a phenyl, benzyl or phenoxy ring, each ring optionally substituted with from one to three substituents independently selected from $R^9$. Examples of such substituent rings include the rings illustrated as rings U-1 (phenyl), U-87 (benzyl) and U-86 (phenoxy) illustrated in Exhibit 1 above, wherein $R^v$ is $R^9$ and r is an integer from 1 to 3;

As noted above, each $R^5$ can be independently (among others) a phenyl, benzyl, benzoyl, phenoxy or 5- or 6-membered heteroaromatic ring, or an aromatic 8-, 9- or 10-membered fused heterobicyclic ring system, each ring or ring system optionally substituted with from one to three substituents independently selected from $R^9$. Examples of such substituent rings include the rings illustrated as rings U-1 (phenyl), U-87 (benzyl), U-88 (benzoyl), U-86 (phenoxy), U-2 through U-53. (5- or 6-membered heteroaromatic rings) and U-54 through. U-84 (aromatic 8-, 9- or 10-membered fused heterobicyclic ring systems) illustrated in Exhibit 1 above, wherein $R^v$ is $R^9$ and r is an integer from 1 to 3.

As noted above, each $R^6$ and each $R^8$ can be independently (among others) a phenyl ring or a 5- or 6-membered heteroaromatic ring, each ring optionally substituted with from one to three substituents independently selected from $R^9$. Examples of such $R^6$ each $R^8$ groups include the rings illustrated as rings U-1 (phenyl) and U-2 through U-53 (5- or 6-membered heteroaromatic rings)illustrated in Exhibit 1 above, wherein $R^v$ is $R^9$ and r is an integer from 1 to 3.

As noted above, each $R^7$ can be independently a phenyl, benzyloxy or 5- or 6-membered heteroaromatic ring, each ring optionally substituted with from one to three substituents independently selected from $R^9$. Examples of such $R^7$ groups include the rings illustrated as rings U-1 (phenyl), U-90 (benzyloxy) and U-2 through U-53 (5- or 6-membered heteroaromatic rings)illustrated in Exhibit 1 above, wherein $R^v$ is $R^9$ and r is an integer from 1 to 3.

Preferred compounds for reasons of better activity and/or ease of synthesis are:
Preferred 1. Compounds of Formula I wherein K is —NR$^1$C(=A)- and A is O.
Preferred 2. Compounds of Formula I wherein L is —C(=B)NR$^2$— and B is O.
Preferred 3. Compounds of Preferred 1 or Preferred 2 wherein
J is a phenyl ring or a 5- or 6-membered heteroaromatic ring selected from the group consisting of J-1, J-2, J-3 and J-4, each ring substituted with from one to four substituents independently selected from $R^5$

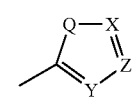
J-1

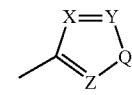
J-2

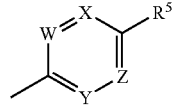
J-3

-continued

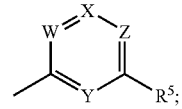
J-4

Q is O, S or NR$^5$;
W, X, Y and Z are independently N or CR$^5$, provided that in J-3 and J-4 at least one of W, X, Y or Z is N;
R$^1$ is H, C$_1$-C$_4$ alkyl, C$_2$-C$_4$ alkenyl, C$_2$-C$_4$ alkynyl, C$_3$-C$_6$ cycloalkyl, C$_2$-C$_6$ alkylcarbonyl or C$_2$-C$_6$ alkoxycarbonyl;
R$^2$ is H, C$_1$-C$_4$ alkyl, C$_2$-C$_4$ alkenyl, C$_2$-C$_4$ alkynyl, C$_3$-C$_6$ cycloalkyl, C$_2$-C$_6$ alkylcarbonyl or C$_2$-C$_6$ alkoxycarbonyl;
R$^3$ is H; or C$_1$-C$_6$ alkyl, C$_2$-C$_6$ alkenyl, C$_2$-C$_6$ alkynyl or C$_3$-C$_6$ cycloalkyl each optionally substituted with one or more substituents independently selected from the group consisting of halogen, CN, C$_1$-C$_2$ alkoxy, C$_1$-C$_2$ alkylthio, C$_1$-C$_2$ alkylsulfinyl and C$_1$-C$_2$ alkylsulfonyl;
one of the R$^4$ groups is attached to remainder of Formula I at either the 2-position or 5-position of the phenyl ring, and said R$^4$ is C$_1$-C$_4$ alkyl, C$_1$-C$_4$ haloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl or C$_1$-C$_4$ haloalkylsulfonyl;
each R$^5$ is independently H, C$_1$-C$_4$ alkyl, C$_1$-C$_4$ haloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_2$-C$_4$ alkoxycarbonyl, C$_2$-C$_6$ alkylaminocarbonyl or C$_3$-C$_8$ dialkylaminocarbonyl; or
each R$^5$ is independently a phenyl, benzyl or 5- or 6-membered heteroaromatic ring, each ring optionally substituted with from one to three substituents independently selected from R$^9$; or
(R$^5$)$_2$ when attached to adjacent carbon atoms can be taken together as —OCF$_2$O—, —CF$_2$CF$_2$O— or —OCF$_2$CF$_2$O—;
each R$^6$ is independently C$_1$-C$_6$ alkyl, C$_2$-C$_6$ alkenyl, C$_2$-C$_6$ alkynyl, each optionally substituted with one or more substituents independently selected from the group consisting of halogen, CN, C$_1$-C$_4$ alkoxy, C$_1$-C$_4$ alkylthio and R$^7$; and
n is 1 or 2.

Of note are compounds of Preferred 3 wherein K is —NR$^1$C(=O)— and L is —C(GR$^6$)=N— or —SO$_2$NR$^2$—. Also of note are compounds of Preferred 3 wherein K is —NR$^1$C(=O)— and L is —C(=O)—. Also of note are compounds of Preferred 3 wherein L is —C(=O)NR$^2$— and K is —N=C(GR$^6$)— or —NR$^1$SO$_2$—.

Preferred 4. Compounds of Preferred 3 wherein
R$^1$ and R$^2$ are each independently H or C$_1$-C$_4$ alkyl;
R$^3$ is C$_1$-C$_4$ alkyl optionally substituted with halogen, CN, OCH$_3$, or S(O)$_p$CH$_3$;
each R$^5$ is independently H, C$_1$-C$_4$ alkyl, C$_1$-C$_4$ haloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl or C$_2$-C$_4$ alkoxycarbonyl, C$_2$-C$_6$ alkylaminocarbonyl or C$_3$-C$_8$ dialkylaminocarbonyl; or a phenyl, benzyl, or 5- or 6-membered heteroaromatic ring, each ring optionally substituted with halogen, CN, NO$_2$, C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_1$-C$_4$ alkoxy or C$_1$-C$_4$ haloalkoxy; provided that one R$^5$ is attached to J at the position ortho to K and at least one R$^5$ is other than H;

G is O or S; and p is 0, 1 or 2.

Preferred 5. Compounds of Preferred 4 wherein J is a phenyl, pyrazole, pyrrole, pyridine or pyrimidine ring, each substituted with one R$^5$ attached to J at the position ortho to K and optionally one or two additional R$^5$.

Preferred 6. Compounds of Preferred 5 wherein

R$^1$ and R$^2$ are both H;

one R$^4$ is attached to remainder of Formula I at the 2-position of the phenyl ring ortho to the K-J moiety and is selected from the group consisting of C$_1$-C$_3$ alkyl, CF$_3$, OCF$_3$, OCHF$_2$, S(O)$_p$CF$_3$, S(O)$_p$CHF$_2$ and halogen and optionally a second R$^4$ is attached at the 4-position of the phenyl ring para to the K-J moiety and is selected from the group consisting of halogen, C$_1$-C$_3$ alkyl and C$_1$-C$_3$ haloalkyl.

Preferred 7. Compounds of Preferred 6 wherein

J is a pyrazole or pyrrole ring selected from the group consisting of J-5, J-6, J-7, J-8, J-9 and J-10, each ring substituted with R$^5$ and optionally substituted with R$^{10}$ and R$^{11}$;

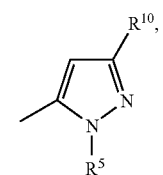
J-5

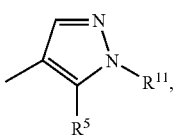
J-6

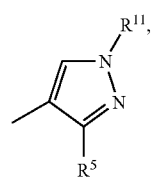
J-7

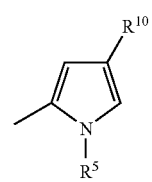
J-8

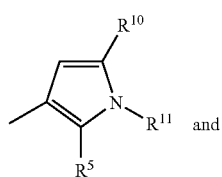
J-9 and

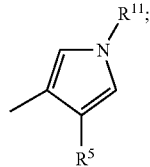
J-10

R$^5$ is H, C$_1$-C$_4$ alkyl, C$_1$-C$_4$ haloalkyl, or

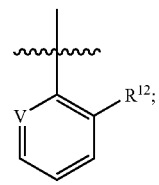

V is N, CH, CF, CCl, CBr or CI;

each R$^{10}$ and each R$^{12}$ is independently H, C$_1$-C$_6$ alkyl, C$_3$-C$_6$ cycloalkyl, C$_1$-C$_6$ haloalkyl, halogen, CN, C$_1$-C$_4$ alkoxy, C$_1$-C$_4$ haloalkoxy or C$_1$-C$_4$ haloalkylthio; and R$^{11}$ is H, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl or C$_3$-C$_6$ haloalkynyl.

Note that R$^{10}$ and R$^{11}$ are subsets of R$^5$. Note that when R$^{12}$ is other than H it is a subset of R$^9$ and that the F, Cl, Br or I atoms encompassed within V are also a subset of R$^9$. Note that the moiety illustrated for R$^5$ is attached to J via the bond highlighted with the wavy line.

Preferred 8. Compounds of Preferred 7 wherein V is N.

Preferred 9. Compounds of Preferred 7 wherein V is CH, CF, CCl or CBr.

Preferred 10. Compounds of Preferred 8 or Preferred 9 wherein

R$^{12}$ is H, C$_1$-C$_4$ alkyl, C$_1$-C$_4$ haloalkyl, halogen or CN;

R$^{10}$ is H, CH$_3$, CF$_3$, OCH$_2$CF$_3$, OCHF$_2$ or halogen; and

R$^{11}$ is CH$_2$CF$_3$, CHF$_2$ or CF$_3$.

Preferred 11. Compounds of Preferred 10 wherein J substituted with R$^5$ and optionally substituted with R$^{10}$ is J-5; R$^{12}$ is Cl or Br; and R$^{10}$ is halogen, OCH$_2$CF$_3$, OCHF$_2$ or CF$_3$.

Preferred 12. Compounds of Preferred 10 wherein J substituted with R$^5$ and optionally substituted with R$^{11}$ is J-6; R$^{12}$ is Cl or Br; and R$^{11}$ is CH$_2$CF$_3$, CHF$_2$ or CF$_3$.

Preferred 13. Compounds of Preferred 10 wherein J substituted with R$^5$ and optionally substituted with R$^{11}$ is J-7; R$^{12}$ is Cl or Br; and R$^{11}$ is CH$_2$CF$_3$, CHF$_2$ or CF$_3$.

Preferred 14. Compounds of Preferred 10 wherein J substituted with R$^5$ and optionally substituted with R$^{10}$ is J-8; R$^{12}$ is Cl or Br; and R$^{10}$ is halogen, OCH$_2$CF$_3$, OCHF$_2$ or CF$_3$.

Preferred 15. Compounds of Preferred 10 wherein J substituted with R$^5$ and optionally substituted with R$^{10}$ and R$^1$ is J-9; R$^{12}$ is Cl or Br; R$^{10}$ is halogen, OCH$_2$CF$_3$, OCHF$_2$ or CF$_3$; and R$^{11}$ is CH$_2$CF$_3$, CHF$_2$ or CF$_3$.

Preferred 16. Compounds of Preferred 10 wherein J substituted with R$^5$ and optionally substituted with R$^{11}$ is J-10; R$^{12}$ is Cl or Br; and R$^{11}$ is CH$_2$CF$_3$, CHF$_2$ or CF$_3$.

Most preferred is the compound of Formula I that is 1-(3-Chloro-2-pyridinyl)-N-[2-methyl-6-[[(1-methylethyl)amino]sulfonyl]phenyl]-3-(trifluoromethyl)-1H-pyrazole-5-carboxamide.

Of note are compounds of Formula If, their N-oxides and agriculturally suitable salts

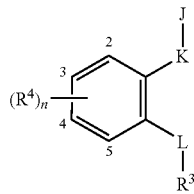

If wherein
J is a phenyl ring, a naphthyl ring system, a 5- or 6-membered heteroaromatic ring or an aromatic 8-, 9- or 10-membered fused heterobicyclic ring system wherein each ring or ring system is optionally substituted with 1 to 4 $R^5$;

K is —$NR^1C(=A)$-, —$N=C(GR^6)$— or —$NR^1SO_2$—;

L is —$C(=B)NR^2$—, —$C(GR^6)=N$—, —$SO_2NR^2$—, or —$C(=O)$—;

A and B are independently O, S, $NR^6$, $NOR^6$, $NN(R^6)_2$, S=O, N—CN or N—$NO_2$;

each G is independently O, S or $NR^6$;

$R^1$ is H; or $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $NO_2$, hydroxy, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkoxycarbonyl, $C_1$-$C_4$ alkylamino, $C_2$-$C_8$ dialkylamino and $C_3$-$C_6$ cycloalkylamino; or $R^1$ is $C_2$-$C_6$ alkylcarbonyl, $C_2$-$C_6$ alkoxycarbonyl, $C_2$-$C_6$ alkylaminocarbonyl or $C_3$-$C_8$ dialkylaminocarbonyl;

$R^2$ is H, $C_1$-$C_6$ alkyl, $C_2$-$C_6$ alkenyl, $C_2$-$C_6$ alkynyl, $C_3$-$C_6$ cycloalkyl, $C_1$-$C_4$ alkoxy, $C_1$-$C_4$ alkylamino, $C_2$-$C_8$ dialkylamino, $C_3$-$C_6$ cycloalkylamino, $C_2$-$C_6$ alkoxycarbonyl or $C_2$-$C_6$ alkylcarbonyl;

$R^3$ is H; $C_1$-$C_6$ alkyl, $C_2$-$C_6$ alkenyl, $C_2$-$C_6$ alkynyl, $C_3$-$C_6$ cycloalkyl, each optionally substituted with one or more substituents selected from the group consisting of halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, or a phenyl, phenoxy or 5- or 6-membered heteroaromatic ring, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl or $C_2$-$C_6$ alkylcarbonyl; or $R^2$ and $R^3$ can be taken together with the nitrogen to which they are attached to form a ring containing 2 to 6 atoms of carbon and optionally one additional atom of nitrogen, sulfur or oxygen, said ring optionally substituted with 1 to 4 substituents selected from the group consisting of $C_1$-$C_2$ alkyl, halogen, CN, $NO_2$ and $C_1$-$C_2$ alkoxy;

each $R^4$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, or $C_3$-$C_6$ trialkylsilyl; or each $R^4$ is independently phenyl, benzyl or phenoxy, each optionally substituted with $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, CN, $CO_2H$, $CONH_2$, $NO_2$, hydroxy, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_6$ alkylcarbonyl, $C_2$-$C_6$ alkoxycarbonyl, $C_2$-$C_6$ alkylaminocarbonyl, $C_3$-$C_8$ dialkylaminocarbonyl, $C_3$-$C_6$ trialkylsilyl; or each $R^5$ is independently a phenyl, benzyl, benzoyl, phenoxy, 5- or 6-membered heteroaromatic ring or an aromatic 8-, 9- or 10-membered fused heterobicyclic ring system, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $(R^5)_2$ when attached to adjacent carbon atoms can be taken together as —$OCF_2O$—, —$CF_2CF_2O$— or —$OCF_2CF_2O$—;

each $R^6$ is independently $C_1$-$C_6$ alkyl, $C_2$-$C_6$ alkenyl, $C_2$-$C_6$ alkynyl, optionally substituted with halogen, CN, $C_1$-$C_4$ alkoxy, $C_1$-$C_4$ alkylthio or $R^7$; $C_3$-$C_6$ cycloalkyl; or $C_2$-$C_4$ alkoxycarbonyl; or each $R^6$ is independently a phenyl ring or a 5- or 6-membered heteroaromatic ring, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^7$ is independently a phenyl ring or a 5- or 6-membered heteroaromatic ring, each ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and n is 1 to 4;

provided that when K is —$NR^1C(=A)$- and A is O or S, then L is other than —$C(=O)NR^2$— or —$C(=S)NR^2$—.

Also of note are selected compounds of Formula I

Selection A. Compounds of Formula I wherein K is —$NR^1C(=A)$- and A is O.

Selection B. Compounds of Formula I wherein L is —$C(=B)NR^2$— and B is O.

Selection C. Compounds of Selection B or Selection C wherein

J is a phenyl ring or a 5- or 6-membered heteroaromatic ring selected from the group consisting of J-1, J-2, J-3 and J-4, each J ring optionally substituted with 1 to 3 $R^5$

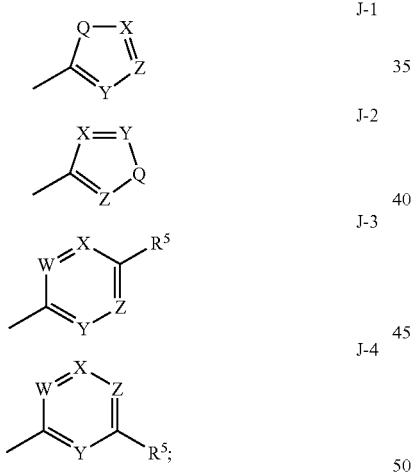

Q is O, S or $NR^5$;

W, X, Y and Z are independently N or $CR^5$, provided that in J-3 and J-4 at least one of W, X, Y or Z is N;

$R^1$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^2$ is H, $C_1$-$C_4$ alkyl, $C_2$-$C_4$ alkenyl, $C_2$-$C_4$ alkynyl, $C_3$-$C_6$ cycloalkyl, $C_2$-$C_6$ alkylcarbonyl or $C_2$-$C_6$ alkoxycarbonyl;

$R^3$ is $C_1$-$C_6$ alkyl, $C_2$-$C_6$ alkenyl, $C_2$-$C_6$ alkynyl or $C_3$-$C_6$ cycloalkyl each optionally substituted with one or more substituents selected from the group consisting of halogen, CN, $C_1$-$C_2$ alkoxy, $C_1$-$C_2$ alkylthio, $C_1$-$C_2$ alkylsulfinyl and $C_1$-$C_2$ alkylsulfonyl;

one of the $R^4$ groups is attached to the phenyl ring at the 2-position or 5-position, and said $R^4$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl or $C_1$-$C_4$ haloalkylsulfonyl;

each $R^5$ is independently H, $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl, $C_3$-$C_8$ dialkylaminocarbonyl; or each $R^5$ is independently a phenyl, benzyl or a 5- or 6-membered heteroaromatic ring, each ring optionally substituted with $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_3$-$C_6$ (alkyl)cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $(R^5)_2$ when attached to adjacent carbon atoms can be taken together as —$OCF_2O$—, —$CF_2CF_2O$— or $CF_2CF_2O$—;

each $R^6$ is independently $C_1$-$C_6$ alkyl, $C_2$-$C_6$ alkenyl, $C_2$-$C_6$ alkynyl, optionally substituted with halogen, CN, $C_1$-$C_4$ alkoxy, $C_1$-$C_4$ alkylthio or $R^7$; and n is 1 to 2.

Of note are compounds of Selection C wherein K is —$NR^1C(=O)$— and L is —$C(GR^6)=N$— or —$SO_2NR^2$—.

Also of note are compounds of Selection C wherein L is —$C(=O)NR^2$— and K is —$N=C(GR^6)$— or —$NR^1SO_2$—.

Selection D. Compounds of Selection C wherein $R^1$ is H or $C_1$-$C_4$ alkyl;

$R^2$ is H or $C_1$-$C_4$ alkyl;

$R^3$ is $C_1$-$C_4$ alkyl optionally substituted with halogen, CN, $OCH_3$, or $S(O)_pCH_3$;

one $R^5$ group is attached to the J at the position ortho to K, and said $R^5$ is $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; $C_3$-$C_8$ dialkylaminocarbonyl or a phenyl, benzyl, or a 5- or 6-membered heteroaromatic ring, each ring optionally substituted with halogen, CN, $NO_2$, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_1$-$C_4$ alkoxy or $C_1$-$C_4$ haloalkoxy;

and an optional second $R^5$ group is independently $C_1$-$C_4$ alkyl, $C_1$-$C_4$ haloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl or $C_2$-$C_4$ alkoxycarbonyl; $C_3$-$C_8$ dialkylaminocarbonyl or a phenyl, benzyl, or a 5- or 6-membered heteroaromatic ring, each ring optionally substituted with halogen, CN, $NO_2$, $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_1$-$C_4$ alkoxy or $C_1$-$C_4$ haloalkoxy;

G is O or S; and p is 0, 1 or 2.

Selection E. Compounds of Selection D wherein J is phenyl, pyrazole, pyrrole, pyridine or pyrimidine, each substituted with one $R^5$ attached to the J at the position ortho to K and a second optional $R^5$.

Selection F. Compounds of Selection L wherein
  $R^1$ and $R^2$ are each H;
    one $R^4$ is attached at the 2-position ortho to the K-J moiety and is selected from the group consisting of $C_1$-$C_3$ alkyl, $CF_3$, $OCF_3$, $OCHF_2$, $S(O)_pCF_3$, $S(O)_pCHF_2$ and halogen and an optional second $R^4$ is attached at the 4-position para to the K-J moiety and is selected from the group consisting of halogen, $C_1$-$C_3$ alkyl and $C_1$-$C_3$ haloalkyl.
Selection G. Compounds of Selection F wherein
  J is J-1;
  Q is $NR^{5a}$;
  X is N or CH;
  Y is CH; Z is $CR^{5b}$;
  $R^{5a}$ is a phenyl or 2-pyridyl ring substituted with one or two substituents selected from the group consisting of halogen, $C_1$-$C_4$ alkyl, $C_1$-$C_4$ haloalkyl or $C_1$-$C_4$ haloalkoxy; and
  $R^{5b}$ is halogen or $CF_3$.

One or more of the following methods and variations as described in Schemes 1-33 can be used to prepare the compounds of Formula I. The definitions of A, B, J, $R^1$, $R^2$, $R^3$, $R^4$, $R^5$, $R^6$, $R^7$, $R^8$, $R^9$ and n in the compounds of Formulae 1-88 below are as defined above in the Summary of the Invention. Compounds of Formulae Ia-e, 2a-b, 4a-s, 5a-d are various subsets of the compounds of Formula I, 2, 4 and 5.

Compounds of Formula Ia (wherein K is $NR^1C(=O)$) can be prepared by coupling of an amine of Formula 2 with an acid chloride of Formula 3 in the presence of an acid scavenger to provide the compound of Formula Ia. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diisopropylethylamine and polymer-bound dimethylaminopyridine. The coupling can be run in a suitable inert solvent such as tetrahydrofuran, dioxane, diethylether or dichloromethane to afford the anilide of Formula Ia. In a subsequent step, amides of Formula Ia can be converted to thioamides of Formula Ib using a variety of standard thio transfer reagents including phosphorus pentasulfide and Lawesson's reagent.

An alternate procedure for the preparation of compounds of Formula Ia involves coupling of an amine of Formula 2 with an acid of Formula 4 in the presence of a dehydrating agent such as dicyclohexylcarbodiimide (DCC). Polymer supported reagents are again useful here, such as polymer-bound cyclohexylcarbodiimide. Synthetic procedures of Schemes 1 and 2 are only representative examples of useful methods for the preparation of Formula I compounds as the synthetic literature is extensive for this type of reaction.

Scheme 2

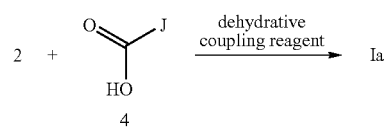

One skilled in the art will also realize that acid chlorides of Formula 3 may be prepared from acids of Formula 4 by numerous well-known methods. For example, acid chlorides of Formula 3 are readily made from carboxylic acids of Formula 4 by reacting the carboxylic acid 4 with thionyl chloride or oxalyl chloride in an inert solvent such as toluene or dichloromethane in the presence of a catalytic amount of N,N-dimethylformamide.

Amines of Formula 2a are typically available from the corresponding nitro compounds of Formula 5 via catalytic hydrogenation of the nitro group. Typical procedures involve reduction with hydrogen in the presence of a metal catalyst such as palladium on carbon or platinum oxide and in hydroxylic solvents such as ethanol and isopropanol. They can also be prepared by reduction with zinc in acetic acid. These procedures are well documented in the chemical literature. $R^1$ substituents such as alkyl, substituted alkyl and the like can generally be introduced at this stage through the generally preferred method of reductive alkylation of the amine. A commonly employed procedure is to combine the aniline 2a with an aldehyde in the presence of a reducing agent such as sodium cyanoborohydride to produce the Formula 2b compounds where $R^1$ is alkyl, alkenyl, alkynyl or substituted derivatives thereof.

Scheme 1

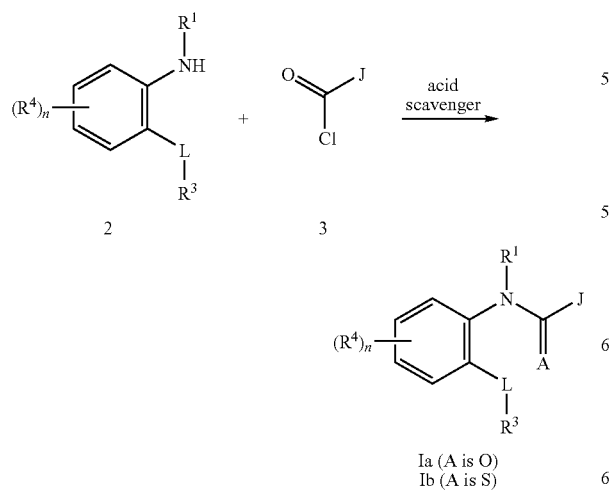

Scheme 3

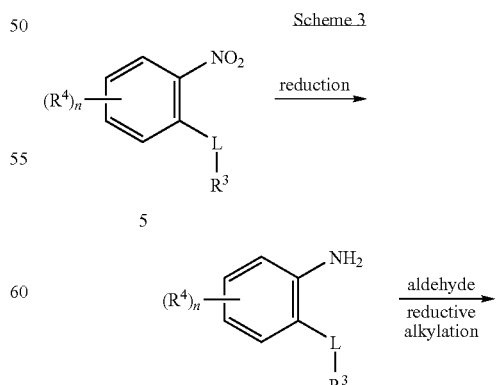

-continued

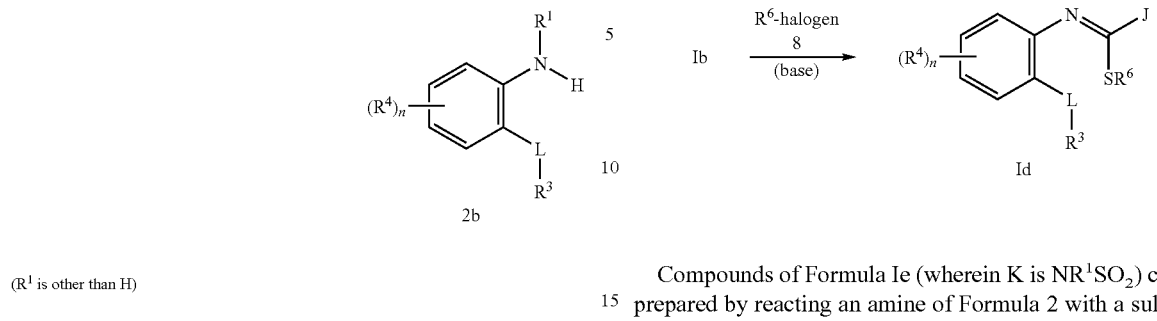

($R^1$ is other than H)

Compounds of Formula Ic (wherein K is N═C(GR$^6$) can be prepared by reaction of imidoylhalides of Formula 6 with sulfur, oxygen and nitrogen nucleophiles of Formula 7. Typically the reactions are conducted in the presence of a base such as a tertiary amine or an alkali metal hydroxide.

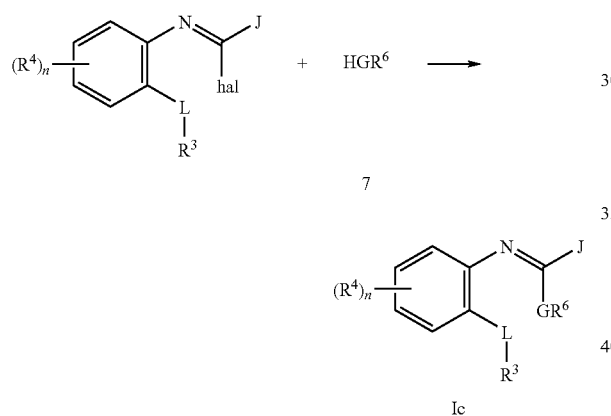

hal is halogen
G is O, S or NR$^8$

Compounds of Formula 6 can be prepared from compounds of Formula Ia by reaction with an appropriate halogenating agent such as phosphorous pentachloride, phosphorous oxychloride, thionyl chloride or triphenyl phosphine and carbon tetrachloride.

Scheme 5

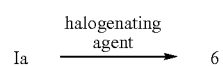

Alternatively compounds of Formula Id (wherein K is N═C(SR$^6$)) when R$^6$ is an alkyl or substituted alkyl group can be prepared from compounds of Formula Ib by reaction with an alkyl halide of Formula 8 optionally in the presence of a base such as a tertiary amine or an alkali metal alkoxide.

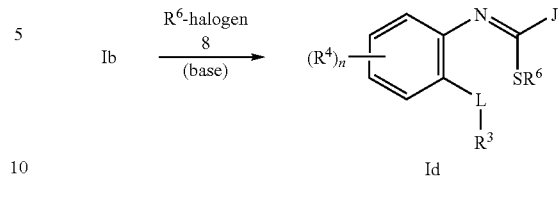

Compounds of Formula Ie (wherein K is NR$^1$SO$_2$) can be prepared by reacting an amine of Formula 2 with a sulfonyl chloride of Formula 9 in the presence of an acid scavenger. Typical acid scavengers include amine bases such as triethylamine, diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound diiospropylethylamine and polymer-bound dimethylaminopyridine.

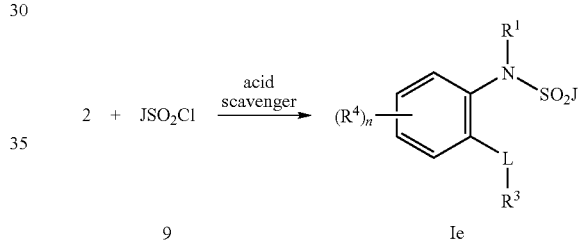

Nitro compounds of Formula 5a (wherein L is C(═O)NR$^2$) can be readily prepared from commercially available 2-nitrobenzoic acids (Scheme 8). Typical methods for amide formation can be applied here. These include direct dehydrative coupling of acids of Formula 10 with amines of Formula 11 using for example DCC, and conversion of the acids to an activated form such as the acid chlorides or anhydrides and subsequent coupling with amines to form amides of Formula 5a. The chemical literature is extensive on this type of reaction. Amides of Formula 5a are readily converted to thioamides of Formula 5b by using commercially available thio transfer reagents such as phosphorus pentasulfide and Lawesson's reagent.

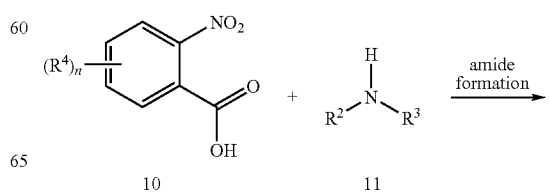

-continued

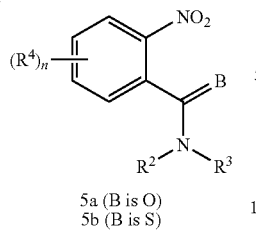

5a (B is O)
5b (B is S)

Nitro compounds of Formula 5c (wherein L is C(GR$^6$)=N) can be prepared from compounds of Formula 5a via imidoyl halides of Formula 12 by methods similar to those described in Schemes 4 and 5.

Scheme 9

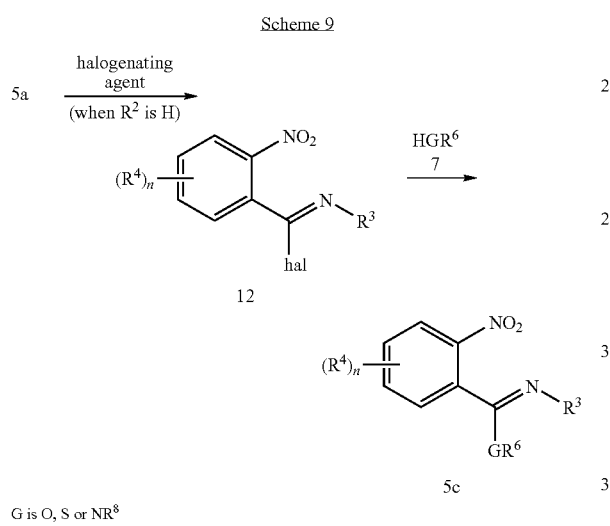

G is O, S or NR$^8$ 379-387) followed by reaction with amines of Formula 11 (see Scheme 8). The synthesis of amines of Formula 13 is well known in the art.

Scheme 10

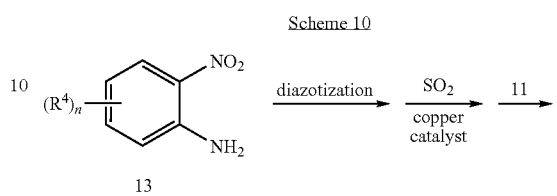

Benzoic acids of Formula 4a (compounds of Formula 4 wherein J is an optionally substituted phenyl ring) are well known in the art. Preparation of certain heterocyclic acids of Formula 4 are described in Schemes 11-16. A variety of heterocyclic acids and general methods for their synthesis may be found in World Patent Application WO 98/57397.

The synthesis of representative pyridine acids (4b) is depicted in Scheme 11. This procedure involves the known synthesis of pyridines from β-ketoesters and 4-aminobutenones (17). Substituent groups R$^5$(c) and R$^5$(d) include e.g. alkyl and haloalkyl.

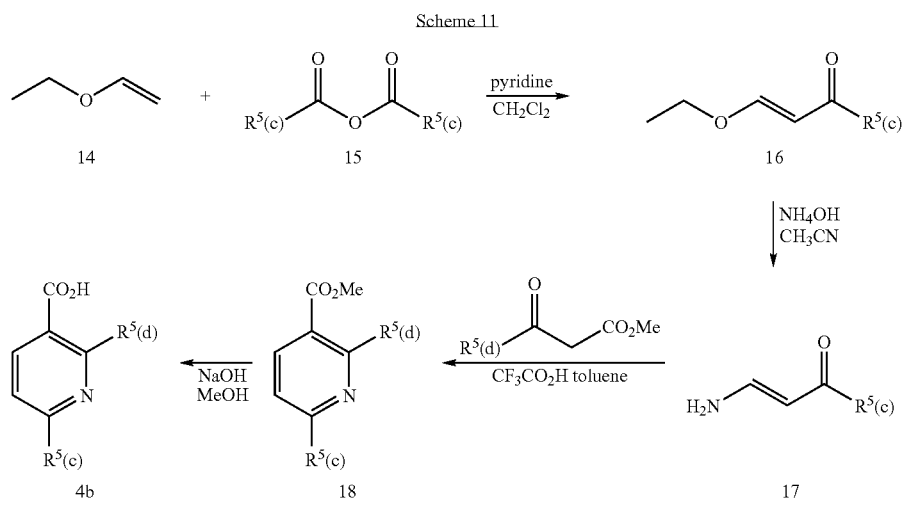

Nitro compounds for Formula 5d (wherein L is SO$_2$NR$^2$) can be prepared from amines of Formula 13 by diazotization with reagents such as sodium nitrite or an alkyl nitrite and reaction with sulfur dioxide in the presence of a copper catalyst (see for instance, Courtin, A. *Helv. Chim. Acta*, 1976, 59, The synthesis of representative pyrimidine acids (4c) is depicted in Scheme 12. This procedure involves the known synthesis of pyrimidines from vinylidene-β-ketoesters (20) and amidines. Substituent groups R$^5$(c) and R$^5$(d) include e.g. alkyl and haloalkyl.

Scheme 12

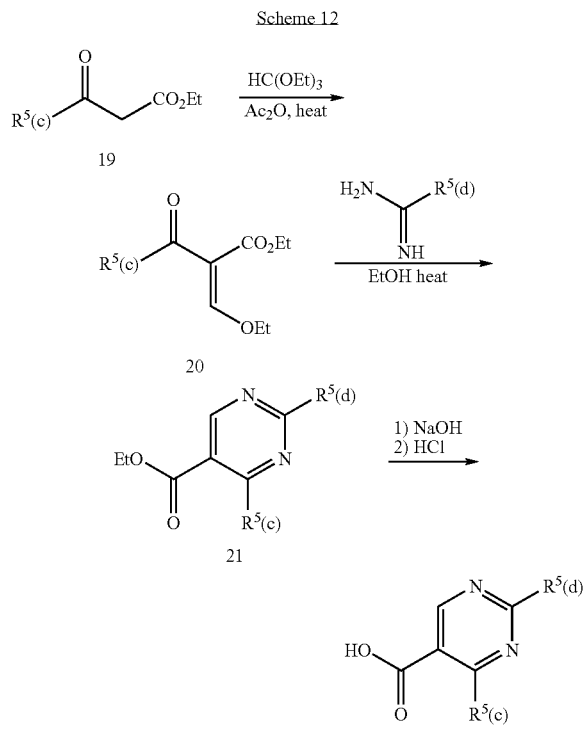

Syntheses of representative pyrazole acids (4d-4g) are depicted in Schemes 13-16. The synthesis of 4d in Scheme 13 involves as the key step introduction of the $R^5(c)$ substituent via alkylation of the pyrazole. The alkylating agent $R^5(c)$-Lg (wherein Lg is a leaving group such as Cl, Br, I, sulfonates such as p-toluenesulfonate or methanesulfonate or sulfates such as —$SO_2OR^5(c)$) includes $R^5(c)$ groups such as $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_6$ alkylcarbonyl, $C_2$-$C_6$ alkoxycarbonyl, $C_3$-$C_8$ dialkylaminocarbonyl, $C_3$-$C_6$ trialkylsilyl; or phenyl, benzyl, benzoyl, 5- or 6-membered heteroaromatic ring or an aromatic 8-, 9- or 10-membered fused heterobicyclic ring system, each ring or ring system optionally substituted. Oxidation of the methyl group affords the pyrazole carboxylic acid. Some of the more preferred $R^5(d)$ groups include haloalkyl.

Scheme 13

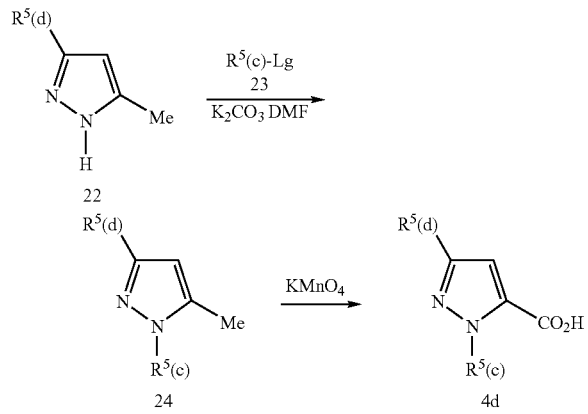

Lg is a leaving group

Some pyrazole acids of Formula 4d may be prepared via metallation and carboxylation of pyrazoles of Formula 26 as the key step (Scheme 14). The $R^5(c)$ group is introduced in a manner similar to that of Scheme 13, i.e. via alkylation with a $R^5(c)$ alkylating agent. Representative $R^5(d)$ groups include e.g. cyano and haloalkyl.

Scheme 14

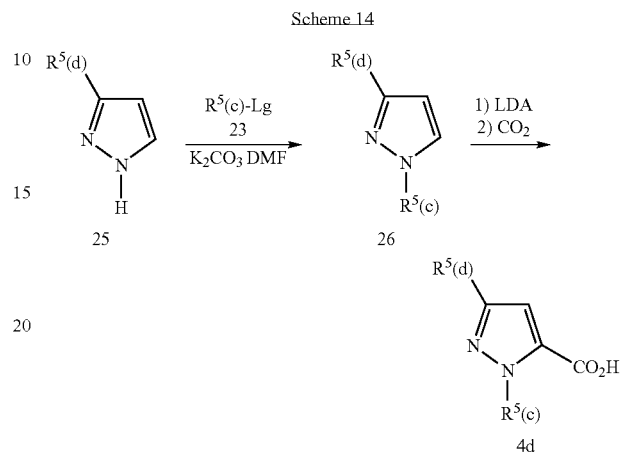

This procedure is particularly useful for preparing 1-(2-pyridinyl)pyrazolecarboxylic acids of Formula 4e, related to preferred moiety J-5 wherein $R^5$ is a substituted 2-pyridinyl ring, as shown in Scheme 15. Reaction of a pyrazole of Formula 27 with a 2,3-dihalopyridine of Formula 23 affords good yields of the 1-pyridinylpyrazole of Formula 28 with good specificity for the desired regiochemistry. Metallation of 28 with lithium diisopropylamide (LDA) followed by quenching of the lithium salt with carbon dioxide affords the 1-(2-pyridinyl)pyrazolecarboxylic acid of Formula 4e.

Scheme 15

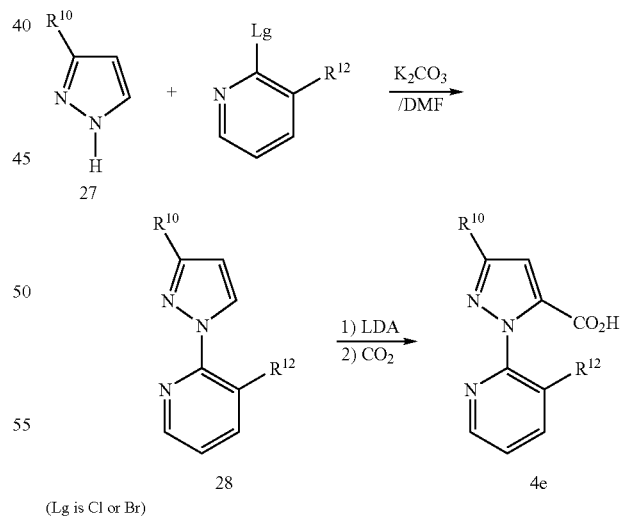

(Lg is Cl or Br)

Other pyrazoles of Formula 4d can be prepared via reaction of an optionally substituted phenyl hydrazine of Formula 30 with a pyruvate of Formula 29 to yield pyrazole esters of Formula 31 (Scheme 16). Hydrolysis of the ester affords the pyrazole acids 4d. This procedure is particularly useful for the preparation of compounds where $R^5(c)$ is optionally substituted phenyl and $R^5(d)$ is haloalkyl.

Scheme 16

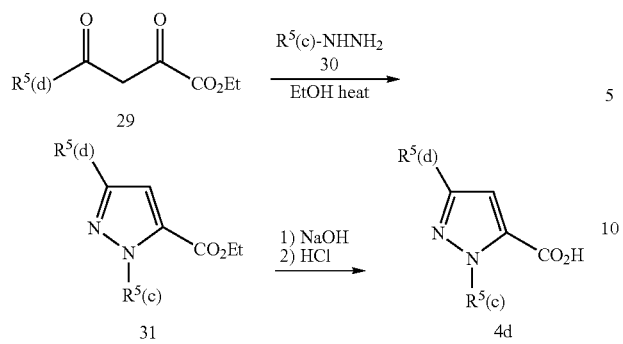

Pyrazole acids of Formula 4d can also be prepared via 3+2 cycloaddition of an appropriately substituted nitrilimine of Formula 32 with either substituted propiolates of Formula 33 or acrylates of Formula 34 (Scheme 17). Cycloaddition with acrylates requires additional oxidation of the intermediate pyrazoline to the pyrazole. Hydrolysis of the ester of Formula 31 affords the pyrazole acids 4d. Preferred iminohalides for this reaction include the trifluoromethyl iminochloride (35) and the iminodibromide (36). Compounds such as 35 are known (*J. Heterocycl. Chem.* 1985, 22(2), 565-8). Compounds such as 36 are available by known methods (*Tetrahedron Letters* 1999, 40, 2605). These procedures are particularly useful for the preparation of compounds where $R^5(c)$ is optionally substituted phenyl and $R^5(d)$ is haloalkyl or bromo.

either hexachloroethane (for $R^5(d)$ being Cl) or 1,2-dibromotetrachloroethane (for $R^5(d)$ being Br) affords the halogenated derivatives of Formula 38a. Removal of the sulfamoyl group with trifluoroacetic acid (TFA) at room temperature proceeds cleanly and in good yield to afford the pyrazoles of Formula 25c. One skilled in the art will recognize that Formula 25c is a tautomer of Formula 25b.

Scheme 18

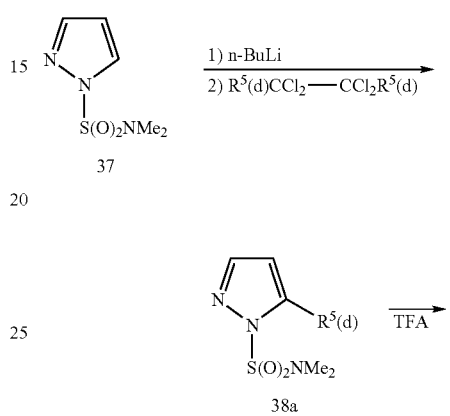

Scheme 17

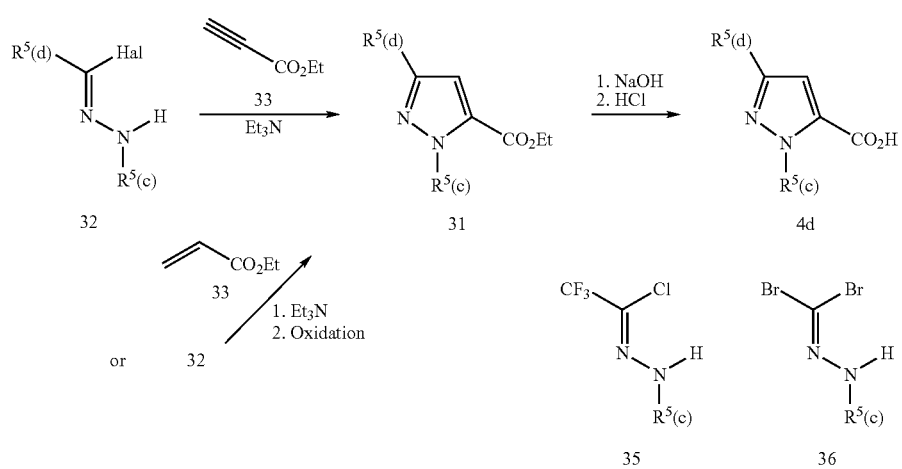

Hal is halogen

The starting pyrazoles of Formula 25 are known compounds or can be prepared according to known methods. The pyrazole of Formula 25a (the compound of Formula 25 wherein $R^5(d)$ is $CF_3$) can be prepared by literature procedures (*J. Fluorine Chem.* 1991, 53(1), 61-70). The pyrazoles of Formula 25b (compounds of Formula 25 wherein $R^5(d)$ is Cl or Br) can be prepared by literature procedures (*Chem. Ber.* 1966, 99(10), 33507). A useful alternative method for the preparation of compound 25b is depicted in Scheme 18. Metallation of the sulfamoyl pyrazole of Formula 37 with n-butyllithium followed by direct halogenation of the anion with -continued

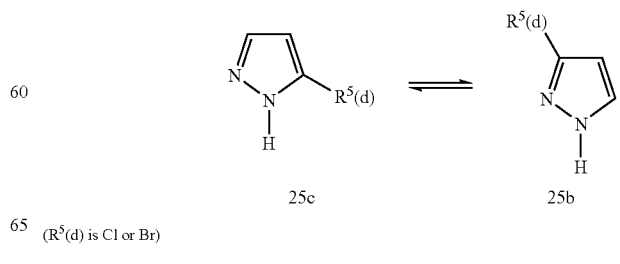

($R^5(d)$ is Cl or Br)

Pyrazolecarboxylic acids of Formula 4f wherein $R^{10}$ is $CF_3$ can be prepared by the method outlined in Scheme 19.

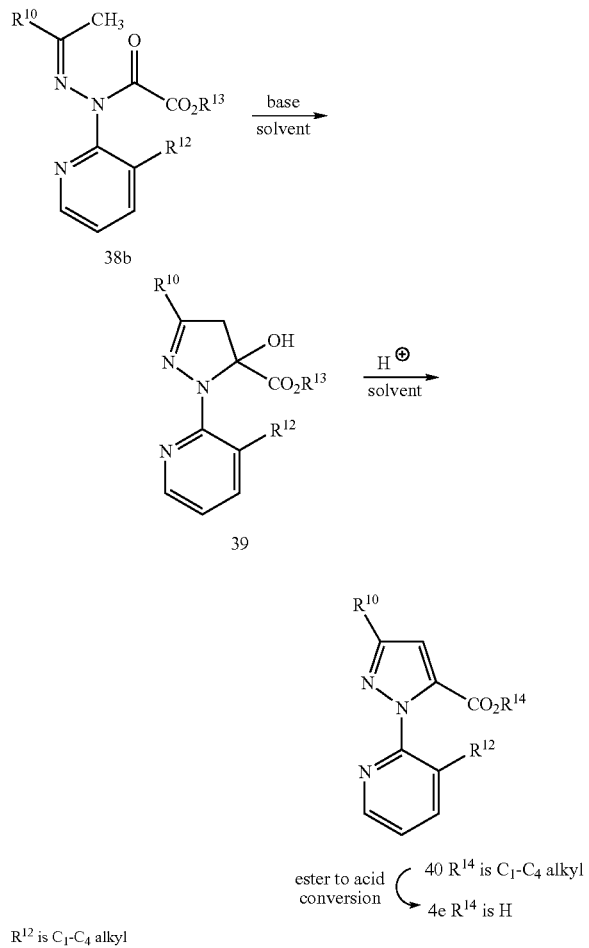

Scheme 19

$R^{12}$ is $C_1$-$C_4$ alkyl

Reaction of a compound of Formula 38b wherein $R^{12}$ is $C_1$-$C_4$ alkyl with a suitable base in a suitable organic solvent affords the cyclized product of Formula 39 after neutralization with an acid such as acetic acid. The suitable base can be, for example but not limitation, sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 39 to give the compound of Formula 40, followed by converting the carboxylic ester function to carboxylic acid, affords the compound of Formula 4f. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 19, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 19, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4f. The carboxylic acid can be isolated by methods known to those skilled in the art, including crystallization, extraction and distillation.

Compounds of Formula 38b can be prepared by the method outlined in Scheme 20.

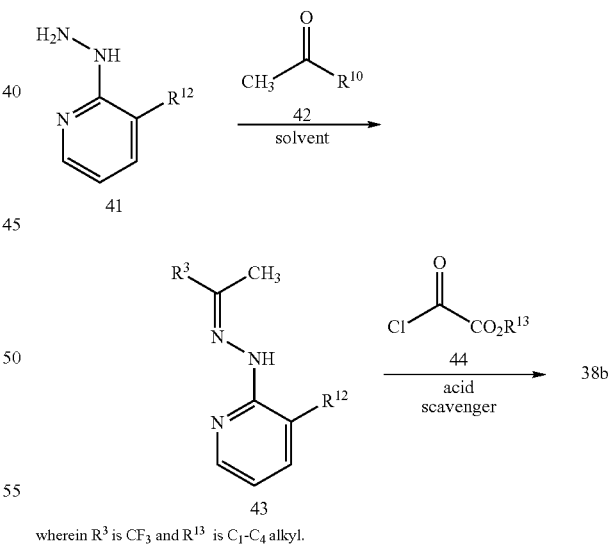

Scheme 20 wherein $R^3$ is $CF_3$ and $R^{13}$ is $C_1$-$C_4$ alkyl.

Treatment of a hydrazine compound of Formula 41 with a ketone of Formula 42 in a solvent such as water, methanol or acetic acid gives the hydrazone of Formula 43. One skilled in the art will recognize that this reaction may require catalysis by an optional acid and may also require elevated temperatures depending on the molecular substitution pattern of the hydrazone of Formula 43. Reaction of the hydrazone of Formula 43 with the compound of Formula 44 in a suitable organic solvent such as, for example but not limitation, dichloromethane or tetrahydrofuran in the presence of an acid scavenger such as triethylamine provides the compound of Formula 38. The reaction is usually conducted at a temperature between about 0 and 100° C. Hydrazine compounds of Formula 98 can be prepared by standard methods, such as by contacting the corresponding halo compound of Formula 23 (Scheme 15) with hydrazine.

Pyrazolecarboxylic acids of Formula 4g wherein $R^{10}$ is Cl or Br can be prepared by the method outlined in Scheme 21.

Scheme 21

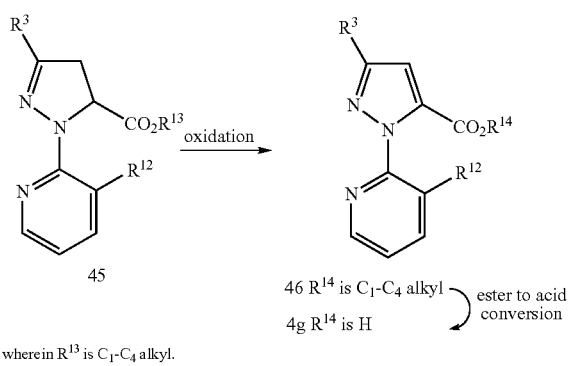

46 $R^{14}$ is $C_1$-$C_4$ alkyl
4g $R^{14}$ is H
} ester to acid conversion wherein $R^{13}$ is $C_1$-$C_4$ alkyl.

Oxidization of the compound of Formula 45 optionally in the presence of acid to give the compound of Formula 46 followed by conversion of the carboxylic ester function to the carboxylic acid provides the compound of Formula 4g. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 45 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 45. To obtain complete conversion, one to five equivalents of acid can be used. The preferred oxidant is potassium persulfate and the oxidation is preferably carried out in the presence of sulfuric acid. The reaction can be carried out by mixing the compound of Formula 45 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 46, can be isolated by methods known to those skilled in the art, including crystallization, extraction and distillation. Methods suitable for converting the ester of Formula 46 to the carboxylic acid of Formula 4g are already described for Scheme 19.

Compounds of Formula 45 can be prepared from corresponding compounds of Formula 47 as shown in Scheme 22.

Scheme 22

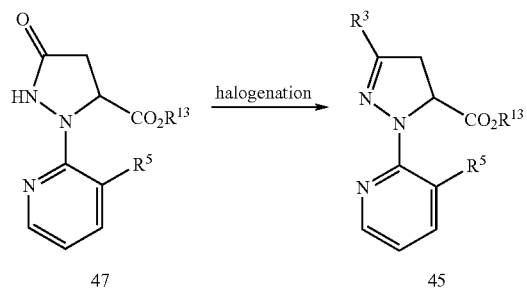

wherein $R^{13}$ is $C_1$-$C_4$ alkyl.

Treatment of a compound of Formula 47 with a halogenating reagent, usually in the presence of a solvent, affords the corresponding halo compound of Formula 45. Halogenating reagents that can be used include phosphorus oxyhalides, phosphorus trihalides, phosphorus pentahalides, thionyl chloride, dihalotlialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 47 should be used, preferably between about 0.33 and 1.2 equivalents. To obtain complete conversion, at least 0.20 equivalents of phosphorus pentahalide versus the compound of Formula 47 should be used, preferably between about 0.20 and 1.0 equivalents. Compounds of Formula 47 wherein $R^{13}$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 47 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 45, can be isolated by methods known to those skilled in the art, including crystallization, extraction and distillation.

Alternatively, compounds of Formula 45 wherein $R^{10}$ is Br or Cl can be prepared by treating the corresponding compounds of Formula 45 wherein $R^{10}$ is a different halogen (e.g., Cl for making Formula 45 wherein $R^{10}$ is Br) or a sulfonate group such as p-toluenesulfonate with hydrogen bromide or hydrogen chloride, respectively. By this method the $R^{10}$ halogen or sulfonate substituent on the Formula 45 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^{10}$ in the starting compound of Formula 45 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 45 wherein $R^{10}$ is Br) can facilitate the reaction. The product of Formula 45 is isolated by the usual methods known to those skilled in the art, including extraction, distillation and crystallization.

Starting compounds of Formula 45 wherein $R^{10}$ is Cl or Br can be prepared from corresponding compounds of Formula 47 as already described. Starting compounds of Formula 45 wherein $R^{10}$ is a sulfonate group can likewise be prepared from corresponding compounds of Formula 47 by standard methods such as treatment with a sulfonyl chloride (e.g., p-toluenesulfonyl chloride) and base such as a tertiary amine (e.g., triethylamine) in a suitable solvent such as dichloromethane.

Pyrazolecarboxylic acids of Formula 4h wherein $R^{10}$ is $OCH_2CF_3$ can be prepared by the method outlined in Scheme 23. In this method, instead of being halogenated as shown in Scheme 22, the compound of Formula 47 is oxidized to the compound of Formula 48. The reaction conditions for this oxidation are as already described for the conversion of the compound of Formula 45 to the compound of Formula 46 in Scheme 21.

The compound of Formula 48 is then alkylated to form the compound of Formula 50 by contact with an alkylating agent $CF_3CH_2Lg$ (49) in the presence of a base. In the alkylating agent 49, Lg is a nucleophilic reaction leaving group such as halogen (e.g., Br, I), $OS(O)_2CH_3$ (methanesulfonate), $OS(O)_2 CF_3$, $OS(O)_2Ph\text{-}p\text{-}CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C. The product of Formula 50 can be isolated by conventional techniques such as extraction. The ester of Formula 50 can then be converted to the carboxylic acid of Formula 4h by the methods already described for the conversion of Formula 40 to Formula 4f in Scheme 19.

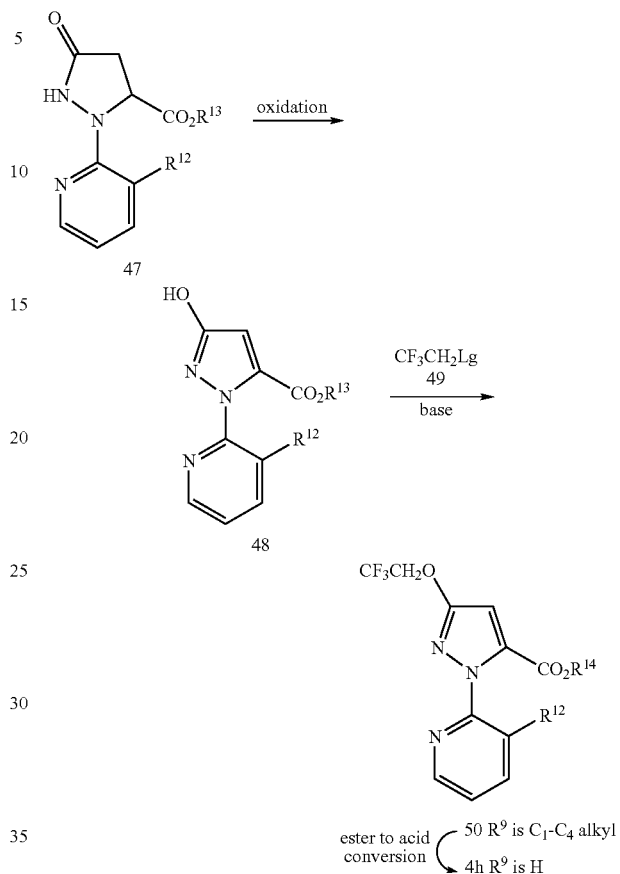

wherein $R^8$ is $C_1\text{-}C_4$ alkyl, and Lg is a leaving group.

Compounds of Formula 47 can be prepared from compounds of Formula 41 (Scheme 20) as outlined in Scheme 24.

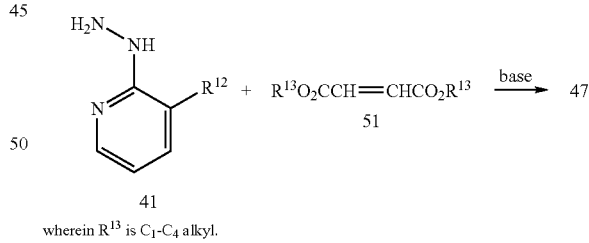

wherein $R^{13}$ is $C_1\text{-}C_4$ alkyl.

In this method, a hydrazine compound of Formula 41 is contacted with a compound of Formula 51 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 51 should be used, preferably between 0.9 and 1.3 equivalents. Greater than 1.0 equivalents of the compound of Formula 108 should be used, preferably between 1.0 to 1.3 equivalents.

Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 108 and the base in the solvent. The mixture can be heated or cooled to a desired temperature and the compound of Formula 98 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 98 and Formula 51. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^{13}$ function on the compound of Formula 47 may be hydrolyzed to —$CO_2H$; for example, the presence of water in the reaction mixture can promote such hydrolysis. If the carboxylic acid (—$CO_2H$) is formed, it can be converted back to —$CO_2R^{13}$ wherein $R^{13}$ is $C_1$-$C_4$ alkyl using esterification methods well-known in the art. The desired product, a compound of Formula 47, can be isolated by methods known to those skilled in the art, such as crystallization, extraction or distillation.

The synthesis of representative pyrazole acids of Formula 4i is depicted in Scheme 25. Reaction of a dimethylaminoylidene ketoester of Formula 53 with substituted hydrazines of formula 30 affords the pyrazoles of Formula 54. Preferred $R^5$(c) substituents include alkyl and haloalkyl, with 2,2,2-trifluoroethyl especially preferred. The esters of Formula 54 are converted to the acids of Formula 4i by standard hydrolysis.

Scheme 25

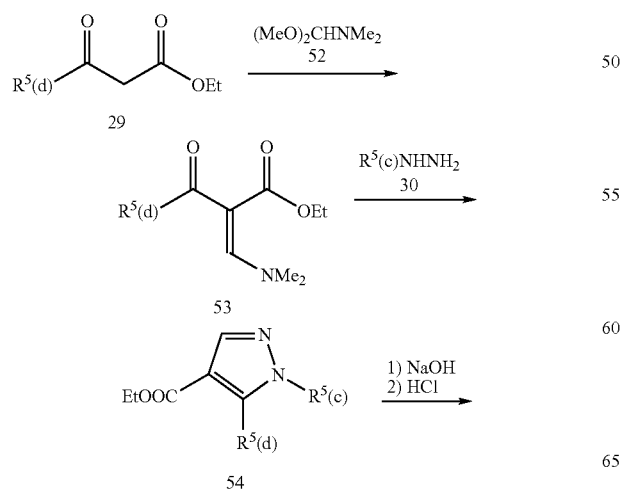

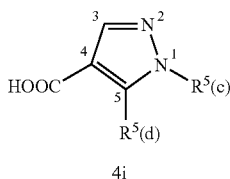

4i

The synthesis of pyrazole acids of Formula 4j, which are related to the preferred moiety J-6 wherein $R^5$ is a substituted 2-pyridyl moiety attached to the 5-position of the pyrazole ring, is depicted in Scheme 26. This synthesis is conducted according to the general synthesis described in Scheme 27.

Scheme 26

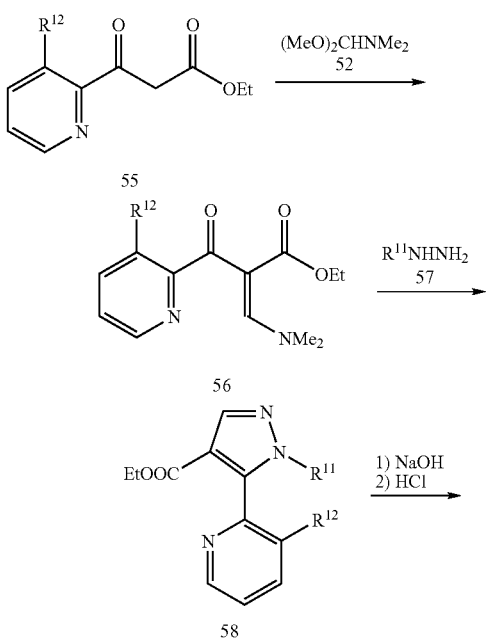

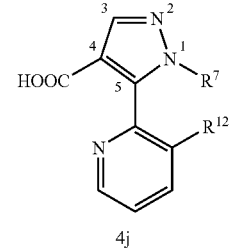

4j

The synthesis of representative pyrazole acids of Formula 4k, as well as an alternative synthesis of Formula 4i, is depicted in Scheme 27. Reaction of the dimethylaminoylidene ketoester of Formula 53 with hydrazine affords the pyrazole of Formula 59. Reaction of the pyrazole 59 with alkylating agents of Formula 60 ($R^5$(c)-Lg wherein Lg is a leaving group such as halogen (e.g., Br, I), OS(O)$_2$CH$_3$ (methanesulfonate), OS(O)$_2$CF$_3$, OS(O)$_2$Ph-p-CH$_3$ (p-toluenesulfonate), and the like) affords a mixture of pyrazoles of Formulae 61 and 62. This mixture of pyrazole isomers is readily separated by chromatographic methods and converted to the corresponding acids. Preferred $R^5$(c) substituents include alkyl and haloalkyl groups.

Scheme 27

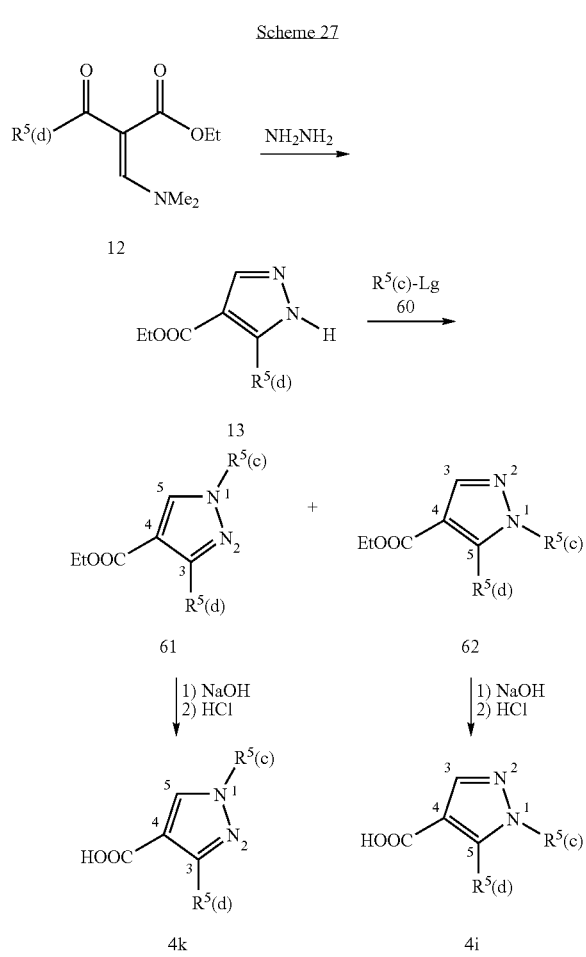

Of note is the synthesis of pyridinylpyrazole acids of Formula 4m, which are related to Formula J-7 wherein $R^5$ is a substituted 2-pyridinyl and attached to the 3-position of the pyrazole ring, as well as an alternative synthesis of Formula 4j, is depicted in Scheme 28. This synthesis is conducted according to the general synthesis described in Scheme 27.

Scheme 28

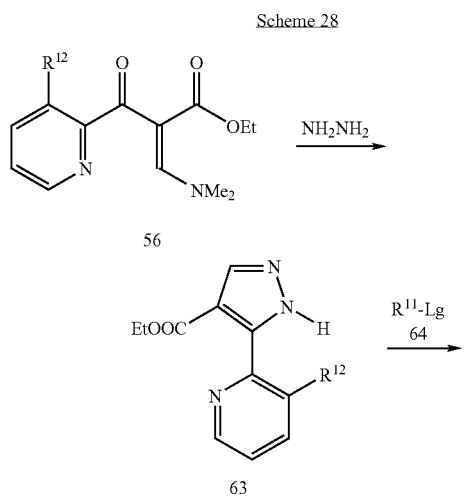

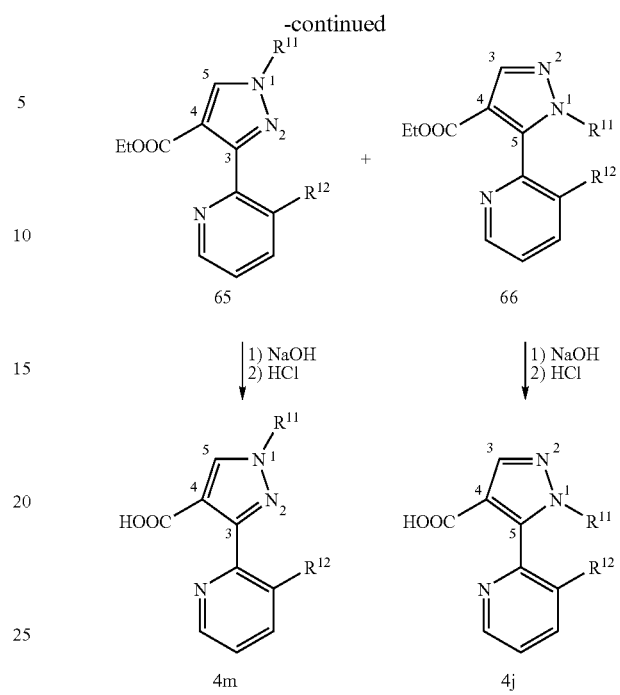

A general synthesis of pyrrole acids of Formula 4n is depicted in Scheme 29. Treatment of a compound of Formula 67 with 2,5-dimethoxytetrahydrofuran (68) affords a pyrrole of Formula 69. Formylation of the pyrrole 69 to provide the aldehyde of Formula 70 can be accomplished by using standard Vilsmeier-Haack formylation conditions, such as N,N-dimethylformamide (DMF) and phosphorus oxychloride. Halogenation of the compound of Formula 70 with N-halosuccinimides (NXS) such as N-chlorosuccinimide or N-bromosuccinimide occurs preferentially at the 4-position of the pyrrole ring. Oxidation of the halogenated aldehyde affords the pyrrole acid of Formula 4n. The oxidation can be accomplished by using a variety of standard oxidation conditions.

Scheme 29

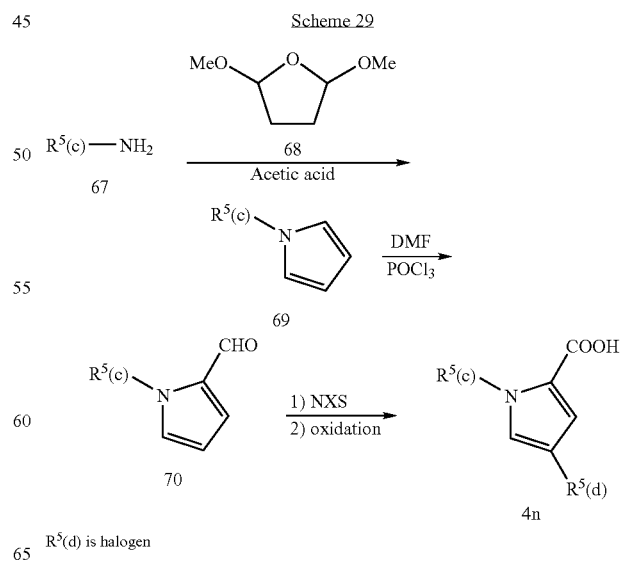

$R^5(d)$ is halogen

The synthesis of certain pyridinylpyrrole acids of Formula 4o, which are related to Formula J-8 wherein $R^5$ is 2-pyridinyl and attached to the nitrogen of the pyrrole ring, is depicted in Scheme 30. The compound of Formula 72, 3-chloro-2-aminopyridine, is a known compound (see *J. Heterocycl. Chem.* 1987, 24(5), 1313-16). A convenient preparation of 72 from the 2-aminopyridine of Formula 71 involves protection, ortho-metallation, chlorination and subsequent deprotection. The remaining synthesis is conducted according to the general synthesis described in Scheme 29.

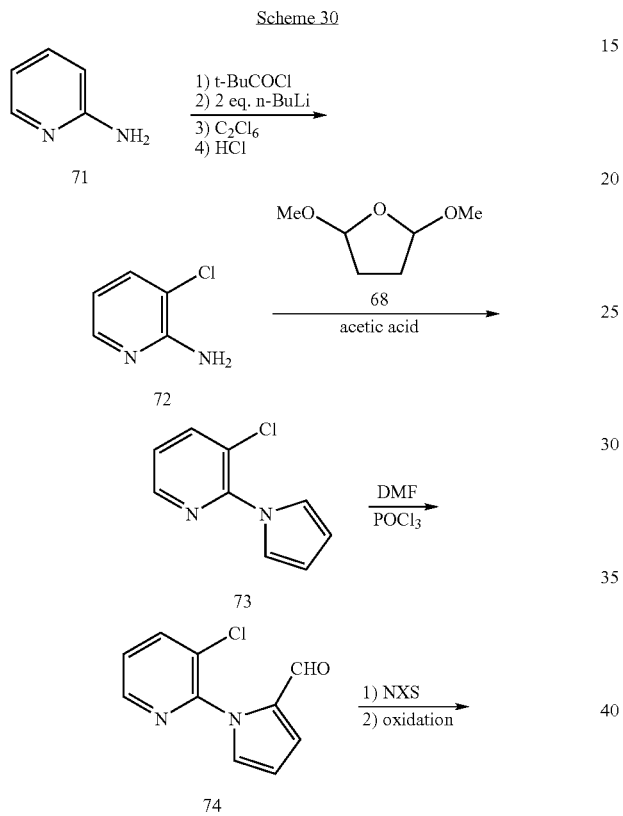

$R^{10}$ is halogen

The synthesis of pyrrole acids of Formula 4p is depicted in Scheme 31. Cycloaddition of an allene of Formula 78 with a phenylsulfonyl hydrazide of Formula 77 (see Pavri, N. P.; Trudell, M. L. *J. Org. Chem.* 1997, 62, 2649-2651) affords a pyrroline of Formula 79. Treatment of the pyrroline of Formula 79 with tetrabutylammonium fluoride (TBAF) gives a pyrrole of Formula 80. Reaction of the pyrrole 80 with an alkylating agent $R^5$(d)-Lg (wherein Lg is a leaving group as defined above), followed by hydrolysis, affords a pyrrole acid of Formula 4p.

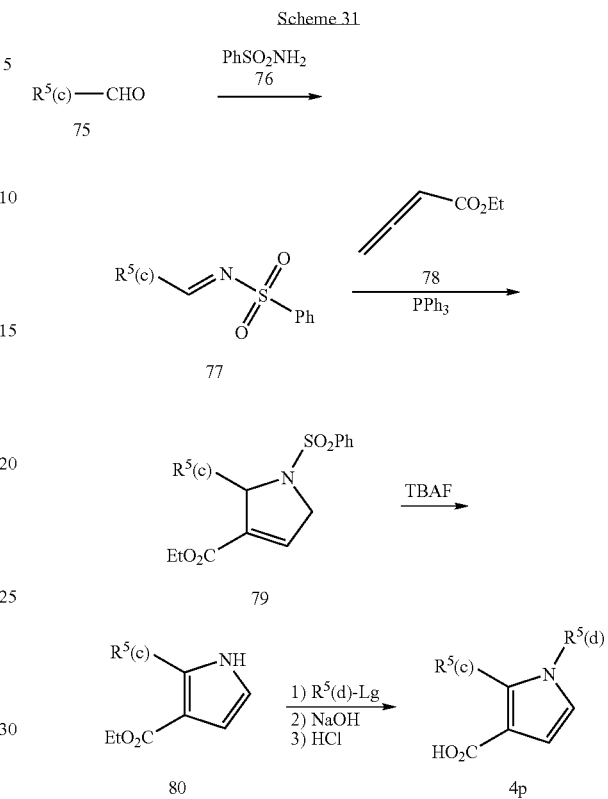

The synthesis of pyrrole acids of Formula 4q, which are related to Formula J-9 wherein $R^5$ is phenyl or 2-pyridyl and attached to the 2-position of the pyrrole ring, is depicted in Scheme 32. The synthesis is conducted according to the general method described for Scheme 31.

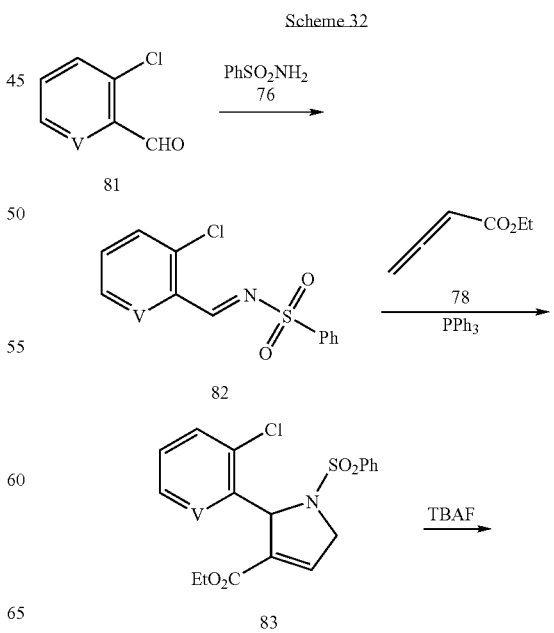

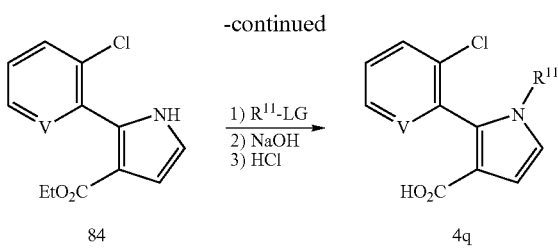

The synthesis of pyrrole acids of Formula 4r is depicted in Scheme 33. Reaction of an α,β-unsaturated ester of Formula 85 with p-tolylsulfonylmethyl isocyanide (TosMIC) provides a pyrrole of Formula 86. For a leading reference, see Xu, Z. et al, *J. Org. Chem.*, 1988, 63, 5031-5041. Reaction of the pyrrole of Formula 86 with an alkylating agent $R^5$(d)-Lg (wherein Lg is a leaving group as defined above) followed by hydrolysis affords a pyrrole acid of Formula 4r.

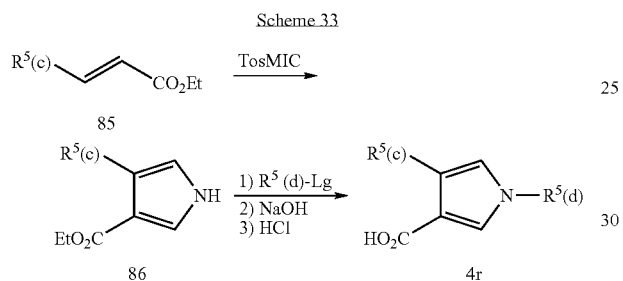

The synthesis of pyrrole acids of Formula 4s, which are related to Formula J-6, wherein $R^5$ is a substituted phenyl or a substituted 2-pyridinyl ring, is depicted in Scheme 35. The synthesis is conducted according to the general method described for Scheme 33.

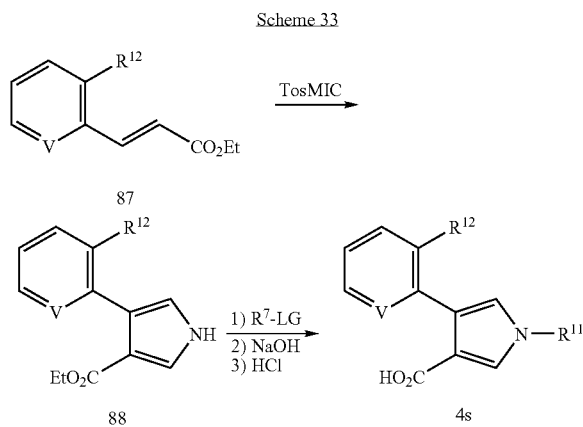

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s means singlet, d means doublet, t means triplet, q means quartet, m means multiplet, dd means doublet of doublets, dt means doublet of triplets, br s means broad singlet and br d means broad doublet.

EXAMPLE 1

Preparation of N-[2-methyl-6-[[(1-methylethyl)amino]sulfonyl]phenyl]-4-(trifluoromethoxy)benzamide Step A: Preparation of 3-methyl-N-(1-methylethyl)-2-nitrobenzenesulfonamide To a solution of isopropylamine (13 mL, 155 mmol) in 60 mL of dichloromethane at 0° C. was added a solution of 5.3 g of 3-methyl-2-nitrobenzenesulfonyl chloride (prepared according to Courtin, A. *Helv. Chim. Acta*, 1976, 59, 379-387) in 60 mL of dichloromethane dropwise. The reaction mixture was stirred 2 hours at room temperature. Water was added and the layers were separated. The organic layer was dried (sodium sulfate) and the volatiles were removed with a rotary evaporator. The residue was purified by medium pressure liquid chromatography (MPLC), using 20-40% ethyl acetate in hexanes as eluant, to afford 4.3 g of the title compound as a yellow solid.

$^1$H NMR (CDCl$_3$) δ 1.12 (d, 6H), 2.39 (s, 1H), 3.56 (m, 1H), 4.65 (br d, 1H), 7.54 (m, 2H), 7.91 (dd, 1H).

Step B: Preparation of 2-amino-3-methyl-N-(1-methylethyl)benzenesulfonamide

To a mixture of 4.13 g of the material from Step A and 0.25 g of 10% palladium on carbon was added 150 mL of ethanol. The reaction mixture was stirred under a balloon of hydrogen for three days. The mixture was filtered through celite and the solvent was removed with a rotary evaporator to afford 3.65 g of the title compound as a brown oil.

$^1$H NMR (CDCl$_3$) δ 1.03 (d, 6H), 2.21 (s, 1H), 3.60 (m, 1H), 4.57 (br d, 1H), 4.86 (br s, 2H), 6.73 (dd, 1H), 7.24 (d, 1H), 7.64 (d, 1H).

Step C: Preparation of N-[2-methyl-6-[[(1-methylethyl)amino]sulfonyl]phenyl]-4-(trifluoromethoxy)benzamide To 0.30 g (1.4 mmol) of the material from Step B in 5 mL of chloroform was added 0.28 ml (3.5 mmol) of pyridine and 0.27 mL (1.7 mmol) of 4-(trifluoromethoxy)benzoyl chloride. The reaction mixture was stirred overnight at room temperature and then heated at reflux for 5 hours. After cooling to room temperature the reaction mixture was washed with 1N HCl, dried (sodium sulfate) and filtered. The volatiles were removed with a rotary evaporator. The residue was purified by MPLC (5-25% ethyl acetate in hexanes as eluant) to afford 0.10 g of the title compound, a compound of the invention, as a white solid melting at 104-107° C.

$^1$H NMR (CDCl$_3$) δ 0.99 (d, 6H), 2.36 (s, 1H), 3.32 (m, 1H), 4.07 (br d, 1H), 7.35 (m, 3H), 7.56 (d, 1H), 7.89 (d, 1H), 8.05 (d, 2H), 8.78 (br s, 1H).

EXAMPLE 2

Preparation of 2-[[[1-(3-Chloro-2-pyridinyl)-3-(trifluoromethyl)-1H-pyrazol-5-yl]sulfonyl]amino]-3-methyl-N-(1-methylethyl)benzamide Step A: Preparation of 3-chloro-2-[3-(trifluoromethyl)-1H-pyrazol-1-yl]pyridine To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the desired intermediate as a clear yellow oil (113.4 g).

$^1$H NMR (CDCl$_3$) δ 6.78 (s, 1H), 7.36 (t, 1H), 7.93 (d, 1H), 8.15 (s, 1H), 8.45 (d, 1H).

Step B: Preparation of Lithium 1-(3-chloro-2-pyridinyl)-3-(trifluoromethyl)-1H-pyrazole-5-sulfinate To a solution of isopropylamine (2.5 mL, 30 mmol) in 25 mL of tetrahydrofuran at −78° C. was added dropwise 7.1 mL (18 mmol) of a 2.5M solution of n-butyllithium in hexanes. This solution was added via cannula to a solution of 4.0 g of 3-chloro-2-[3-(trifluoromethyl)-1H-pyrazol-1-yl]pyridine (i.e. the title material from Step A) in 50 mL of tetrahydrofuran at −78° C. The reaction mixture turned orange. After 15 minutes an additional 20 mL of tetrahydrofuran was added. Sulfur dioxide was bubbled through the solution for 5 minutes. The orange color disappeared. After 15 minutes the reaction mixture was filtered and the solvent was removed from the filtrate with a rotary evaporator. The residue was triturated with ether to afford 4.53 g of the title compound as an off-white solid.

1H NMR (D$_2$O) δ 7.08 (s, 1H), 7.72 (dd, 1h), 8.24 (dd, 1h), 8.55 (dd, 1h).

Step C: Preparation of 1-(3-Chloro-2-pyridinyl)-3-(trifluoromethyl)-1H-pyrazole-5-sulfonic acid To 100 mL of pH 6 buffer (prepared by dissolving 1.2 g (10 mmol) of sodium dihydrogenphosphate in 100 mL of water and adding 11.2 mL of 1N sodium hydroxide) was added 3.52 g (11.1 mmol) of the title material from Step B. This solution was cooled in an ice bath and 75 mL of ethyl acetate and 1.48 g (11.1 mmol) of N-chlorosuccinimide were added. After 30 minutes the layers were separated. The organic layer was dried (sodium sulfate) and the solvent was removed with a rotary evaporator. To the residue was added carbon tetrachloride and the solids were removed by filtration. The solvent was removed from the filtrate with a rotary evaporator to afford 2.84 g of the title compound as an amber oil. $^1$HNMR (CDCl$_3$) δ 7.45 (s, 1H), 7.58 (dd, 1h), 8.01 (dd, 1h), 8.58 (dd, 1h).

Step D: Preparation of 3-methyl-N-(1-methylethyl)-2-nitrobenzamide

A solution of 3-methyl-2-nitrobenzoic acid (2.00 g, 11.0 mmol) and triethylamine (1.22 g, 12.1 mmol) in 25 mL of dichloromethane was cooled to 10° C. Ethyl chloroformate was carefully added and a solid precipitate formed. After the mixture was stirred for 30 minutes isopropylamine (0.94 g, 16.0 mmol) was added and a homogeneous solution resulted. The reaction mixture was stirred for an additional hour, poured into water and extracted with ethyl acetate. The organic extracts were washed with water, dried over magnesium sulfate and evaporated under reduced pressure to afford 1.96 g of the desired intermediate as a white solid melting at 126-128° C.

$^1$H NMR (CDCl$_3$) δ 1.24 (d, 6H), 2.38 (s, 3H), 4.22 (m, 1H), 5.80 (br s, 1H), 7.4 (m, 3H).

Step E: Preparation of 2-amino-3-methyl-N-(1-methylethyl)benzamide

The 2-nitrobenzamide of Step D (1.70 g, 7.6 mmol) was hydrogenated over 5% palladium on carbon in 40 mL of ethanol at 345 kPa (50 psi). When the uptake of hydrogen ceased the reaction was filtered through Celite® filter agent and the Celite® was washed with ether. The filtrate was evaporated under reduced pressure to afford 1.41 g of the title compound as a solid melting at 149-151° C.

$^1$H NMR (CDCl$_3$) δ 1.24 (dd, 6H), 2.16 (s, 3H), 4.25 (m, 1H), 5.54 (br s, 2H), 5.85 (br s, 1H), 6.59 (t, 1H), 7.13 (d, 1H), 7.17 (d, 1H).

Step F: Preparation of 2-[[[1-(3-Chloro-2-pyridinyl)-3-(trifluoromethyl)-1H-pyrazol-5-yl]sulfonyl]amino]-3-methyl-N-(1-methylethyl)benzamide To 2.84 g (10.2 mmol) of 1-(3-chloro-2-pyridinyl)-3-(trifluoromethyl)-1H-pyrazole-5-sulfonic acid (i.e. the title material from Step C) in 70 mL of dichloromethane was added 1.96 g (10.2 mmol) of 2-amino-3-methyl-N-(1-methylethyl)benzamide (i.e. the title compound of Step E) 1.78 mL (10.2 mmol) of diisopropylethylamine and approximately 5 mg of 4-(dimethylamino)pyridine. The reaction mixture was stirred for 9 hours, then washed with water and dried (sodium sulfate). The solvent was removed with a rotary evaporator. The residue was purified by MPLC (20-40% ethyl acetate in hexanes as eluant) to afford 0.50 g of the title compound as a foamy white solid melting at 69-72° C.

$^1$H NMR (CDCl$_3$) δ 0.1.12 (d, 6H), 2.32 (s, 1H), 3.85 (m, 1H), 5.96 (brd, 1H), 7.07 (s, 1H), 7.35 (m, 3H), 7.39 (dd, 1H), 7.89 (dd, 1H), 8.20 (dd, 1H), 9.26 (s, 1H).

EXAMPLE 3

Preparation of 3-Bromo-1-(3-chloro-2-pyridinyl)-N-[2-methyl-6-(3-methyl-1-oxobutyl)phenyl]-1H-pyrazole-5-carboxamide Step A: Preparation of 3-bromo-N,N-dimethyl-1H-pyrazole-1-sulfonamide To a solution of N,N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes, after which time a solution of 1,2-dibromo-tetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with dichloromethane (4×), and the organic extracts were dried over magnesium sulfate and concentrated. The crude product was further purified by chromatography on silica gel using dichloromethane-hexane (50:50) as eluent to afford the title compound as a clear colorless oil (57.04 g).

$^1$H NMR (CDCl$_3$) δ 3.07 (d, 6H), 6.44 (m, 1H), 7.62 (m, 1H).

Step B: Preparation of 3-bromopyrazole

To trifluoroacetic acid (70 mL) was slowly added 3-bromo-N,N-dimethyl-1H-pyrazole-1-sulfonamide (i.e. the bromopyrazole product of Step A) (57.04 g). The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with dichloromethane (3×), dried over magnesium sulfate and concentrated to afford the title compound as a white solid (25.9 g), m.p. 61-64° C.

$^1$H NMR (CDCl$_3$) δ 6.37 (d, 1H), 7.59 (d, 1H), 12.4 (br s, 1H).

Step C: Preparation of 2-(3-bromo-1H-pyrazol-1-yl)-3-chloropyridine

To a mixture of 2,3-dichloropyridine (27.4 g, 185 mmol) and 3-bromopyrazole (i.e. the product of Step B) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The aqueous mixture of precipitated solids was stirred for 1.5 hours, filtered and washed with water (2×100 mL). The solid filter cake was taken up in dichloromethane and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hour. The solids were filtered, washed with hexane and dried to afford the title compound as an off-white powder (30.4 g) determined to be >94% pure by NMR. This material was used without further purification in Step D.

$^1$H NMR (CDCl$_3$) δ 6.52 (s, 1H), 7.30 (dd, 1H), 7.92 (d, 1H), 8.05 (s, 1H), 8.43 (d, 1H).

Step D: Preparation of 3-Bromo-1-(3-chloro-2-pyridinyl)-1H-pyrazole-5-carboxylic acid To a solution of 2-(3-bromo-1H-pyrazol-1-yl)-3-chloropyridine (i.e. the pyrazole product of Step C) (30.4 g, 118 mmol) in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous 1N sodium hydroxide solution (20 mL) was added. The aqueous extracts were washed with ether and acidified with hydrochloric acid. The precipitated solids were filtered, washed with water and dried to afford the title compound as a tan solid (27.7 g). (Product from another run following a similar procedure melted at 200-201° C.)

$^1$H NMR (DMSO-d$_6$) δ 7.25 (s, 1H), 7.68 (dd, 1H), 8.24 (d, 1H), 8.56 (d, 1H).

Step E: Preparation of 3-Bromo-1-(3-chloro-2-pyridinyl)-N-[2-methyl-6-(3-methyl-1-oxobutyl)phenyl]-1H-pyrazole-5-carboxamide To a solution of 3-bromo-1-(3-chloro-2-pyridinyl)-1H-pyrazole-5-carboxylic acid (i.e. the pyrazole product of Step D) (500 mg, 1.65 mmol) in dichloromethane (10 mL) was added 1 drop of N,N-dimethylformamide. Oxalyl Chloride (0.43 mL, 5 mmol) was added and the mixture was stirred at 23° C. for 1 hour. The solvent was removed under reduced pressure and the residue was diluted with acetonitrile (20 mL) and the solvent was again removed under reduced pressure. The residue was dissolved in tetrahydrofuran (10 mL) and treated with 1-(2-amino-3-methylphenyl)-3-methyl-1-butanone, prepared according to Chem. Pharm. Bull., 2000, 48, 1-15, (330 mg, 1.6 mmol) and finally triethylamine (0.45 mL, 3.2 mmol). The mixture was heated at 60° C. for 1 hour. The cooled reaction mixture was diluted with ethyl acetate (50 mL) and water (50 mL). The organic layer was washed with water (2×30 mL) and 1N hydrochloric acid (2×30 mL). The separated organic layer was dried over magnesium sulfate and evaporated to dryness under reduced pressure. The residue was subjected to silica gel chromatography using ethyl acetate/hexanes (3:7) as eluent. Appropriate fractions were pooled to afford, after removal of the solvents, the title compound, a compound of the invention (210 mg), as a yellow solid melting at 119-120° C.

$^1$H NMR (CDCl$_3$) δ 0.97 (d, 6H), 2.21 (s, 3H), 2.84 (d, 2H), 7.06 (s, 1H), 7.21 (m, 1H), 7.4 (m, 2H), 7.62 (d, 1H), 7.81 (d, 1H), 8.42 (d, 1H), 10.6 (br, 1H).

By the procedures described herein together with methods known in the art, the following compounds of Tables 1 to 12 can be prepared. The following abbreviations are used in the Tables: i means iso, Me means methyl, Pr means propyl, i-Pr means isopropyl, Ph means phenyl, OMe means methoxy, SMe means methylthio, CN means cyano and NO$_2$ means nitro.

TABLE 1

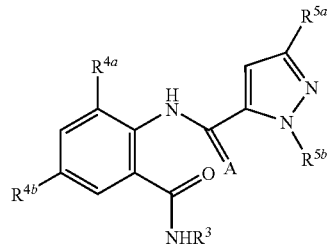

| $R^{4a}$ | $R^{4b}$ | $R^3$ | $R^{5a}$ | $R^{5b}$ |
|---|---|---|---|---|
| \multicolumn{5}{c}{A is NOMe} | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |

TABLE 1-continued

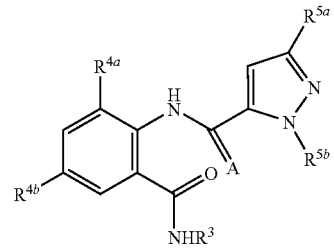

| $R^{4a}$ | $R^{4b}$ | $R^3$ | $R^{5a}$ | $R^{5b}$ |
|---|---|---|---|---|
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| \multicolumn{5}{c}{A is NNMe$_2$} | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |

TABLE 1-continued

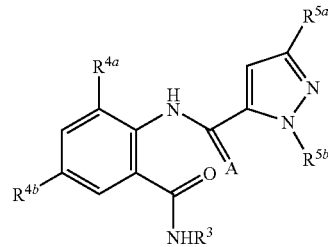

| R4a | R4b | R3 | R5a | R5b |
|---|---|---|---|---|
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |

TABLE 1-continued

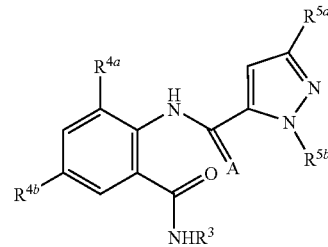

| R4a | R4b | R3 | R5a | R5b |
|---|---|---|---|---|
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |

A is S=O

| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |

TABLE 1-continued

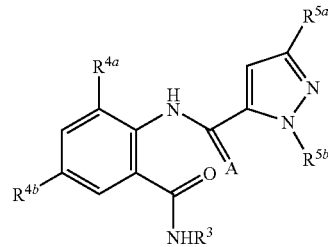

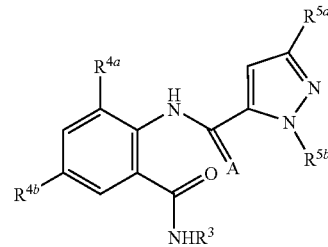

| $R^{4a}$ | $R^{4b}$ | $R^3$ | $R^{5a}$ | $R^{5b}$ |
|---|---|---|---|---|
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| A is N—CN | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |

TABLE 1-continued

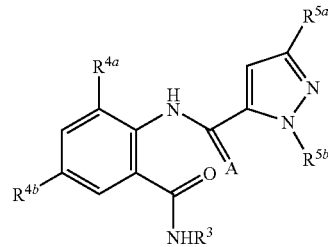 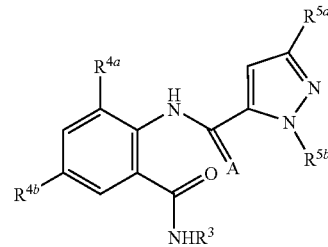

| R4a | R4b | R3 | R5a | R5b |
|---|---|---|---|---|
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| A is N—$NO_2$ | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |

TABLE 1-continued

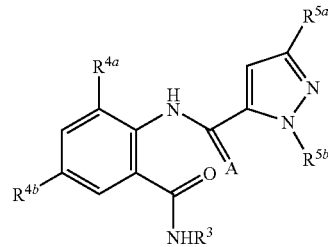

| R4a | R4b | R3 | R5a | R5b |
|---|---|---|---|---|
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |

TABLE 1-continued

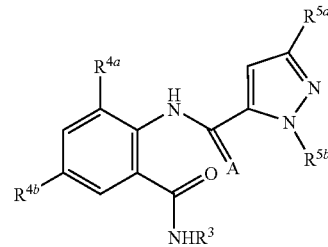

| R4a | R4b | R3 | R5a | R5b |
|---|---|---|---|---|
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| | A is NMe |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |

TABLE 1-continued

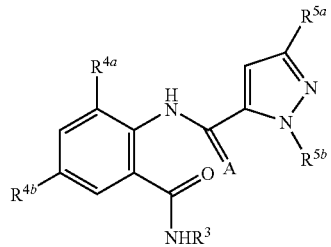

| R4a | R4b | R3 | R5a | R5b |
|---|---|---|---|---|
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |

TABLE 1-continued

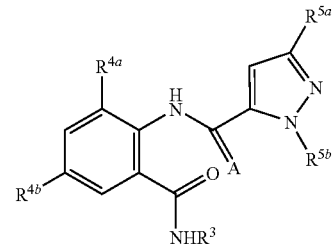

| R4a | R4b | R3 | R5a | R5b |
|---|---|---|---|---|
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |

TABLE 2

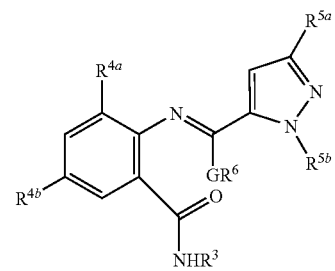

| R4a | R4b | R3 | R5a | R5b |
|---|---|---|---|---|
| GR6 is OMe | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Fr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |

TABLE 2-continued

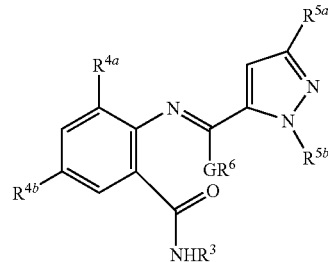

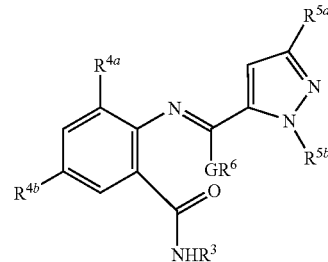

| $R^{4a}$ | $R^{4b}$ | $R^3$ | $R^{5a}$ | $R^{5b}$ |
|---|---|---|---|---|
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| | | | $GR^6$ is SMe | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |

TABLE 2-continued

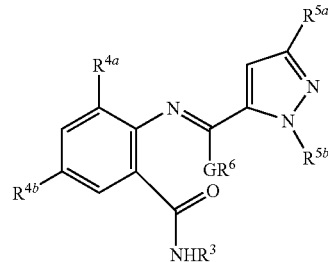

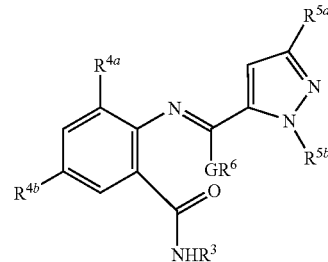

| $R^{4a}$ | $R^{4b}$ | $R^3$ | $R^{5a}$ | $R^{5b}$ |
|---|---|---|---|---|
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| | | | $GR^6$ is $SCH_2Ph$ | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |

TABLE 2-continued

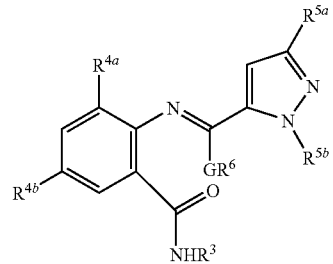

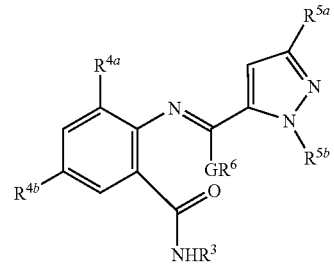

| R4a | R4b | R3 | R5a | R5b |
|---|---|---|---|---|
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| $GR^6$ is $NMe_2$ | | | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |

TABLE 2-continued

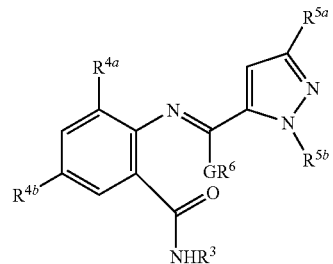

| $R^{4a}$ | $R^{4b}$ | $R^3$ | $R^{5a}$ | $R^{5b}$ |
|---|---|---|---|---|
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |

TABLE 2-continued

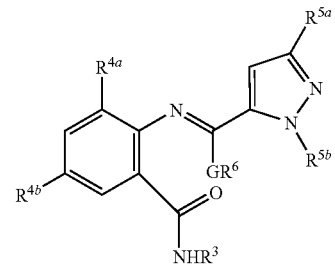

| $R^{4a}$ | $R^{4b}$ | $R^3$ | $R^{5a}$ | $R^{5b}$ |
|---|---|---|---|---|
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |

TABLE 3

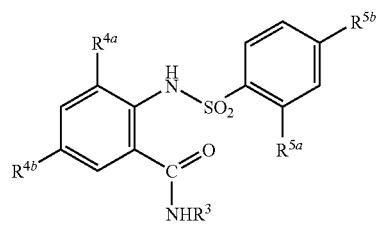

| $R^{4a}$ | $R^{4b}$ | $R^3$ | $R^{5a}$ | $R^{5b}$ |
|---|---|---|---|---|
| Me | H | i-Pr | Me | $CF_3$ |
| Cl | H | i-Pr | Me | $CF_3$ |
| Me | Cl | i-Pr | Me | $CF_3$ |
| Cl | Cl | i-Pr | Me | $CF_3$ |
| Me | Br | i-Pr | Me | $CF_3$ |
| Cl | Br | i-Pr | Me | $CF_3$ |
| Me | H | Me | Me | $CF_3$ |
| Cl | H | Me | Me | $CF_3$ |
| Me | Cl | Me | Me | $CF_3$ |
| Cl | Cl | Me | Me | $CF_3$ |
| Me | Br | Me | Me | $CF_3$ |
| Cl | Br | Me | Me | $CF_3$ |
| Me | H | i-Pr | Me | $OCF_3$ |
| Cl | H | i-Pr | Me | $OCF_3$ |

TABLE 3-continued

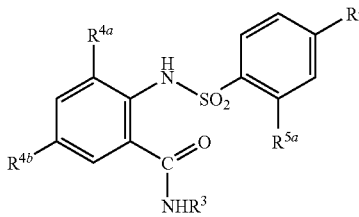

| R<sup>4a</sup> | R<sup>4b</sup> | R<sup>3</sup> | R<sup>5a</sup> | R<sup>5b</sup> |
|---|---|---|---|---|
| Me | Cl | i-Pr | Me | OCF$_3$ |
| Cl | Cl | i-Pr | Me | OCF$_3$ |
| Me | Br | i-Pr | Me | OCF$_3$ |
| Cl | Br | i-Pr | Me | OCF$_3$ |
| Me | H | Me | Me | OCF$_3$ |
| Cl | H | Me | Me | OCF$_3$ |
| Me | Cl | Me | Me | OCF$_3$ |
| Cl | Cl | Me | Me | OCF$_3$ |
| Me | Br | Me | Me | OCF$_3$ |
| Cl | Br | Me | Me | OCF$_3$ |
| Me | H | i-Pr | Me | OCH$_2$CF$_3$ |
| Cl | H | i-Pr | Me | OCH$_2$CF$_3$ |
| Me | Cl | i-Pr | Me | OCH$_2$CF$_3$ |
| Cl | Cl | i-Pr | Me | OCH$_2$CF$_3$ |
| Me | Br | i-Pr | Me | OCH$_2$CF$_3$ |
| Cl | Br | i-Pr | Me | OCH$_2$CF$_3$ |
| Me | H | Me | Me | OCH$_2$CF$_3$ |
| Cl | H | Me | Me | OCH$_2$CF$_3$ |
| Me | Cl | Me | Me | OCH$_2$CF$_3$ |
| Cl | Cl | Me | Me | OCH$_2$CF$_3$ |
| Me | Br | Me | Me | OCH$_2$CF$_3$ |
| Cl | Br | Me | Me | OCH$_2$CF$_3$ |
| Me | H | i-Pr | Me | CF(CF$_3$)$_2$ |
| Cl | H | i-Pr | Me | CF(CF$_3$)$_2$ |
| Me | Cl | i-Pr | Me | CF(CF$_3$)$_2$ |
| Cl | Cl | i-Pr | Me | CF(CF$_3$)$_2$ |
| Me | Br | i-Pr | Me | CF(CF$_3$)$_2$ |
| Cl | Br | i-Pr | Me | CF(CF$_3$)$_2$ |
| Me | H | Me | Me | CF(CF$_3$)$_2$ |
| Cl | H | Me | Me | CF(CF$_3$)$_2$ |
| Me | Cl | Me | Me | CF(CF$_3$)$_2$ |
| Cl | Cl | Me | Me | CF(CF$_3$)$_2$ |
| Me | Br | Me | Me | CF(CF$_3$)$_2$ |
| Cl | Br | Me | Me | CF(CF$_3$)$_2$ |

TABLE 4

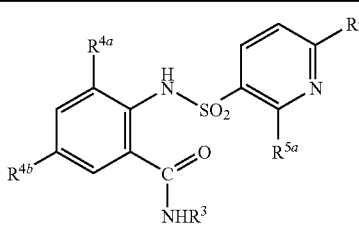

| R<sup>4a</sup> | R<sup>4b</sup> | R<sup>3</sup> | R<sup>5a</sup> | R<sup>5b</sup> |
|---|---|---|---|---|
| Me | H | i-Pr | Me | CF$_3$ |
| Cl | H | i-Pr | Me | CF$_3$ |
| Me | Cl | i-Pr | Me | CF$_3$ |
| Cl | Cl | i-Pr | Me | CF$_3$ |
| Me | Br | i-Pr | Me | CF$_3$ |
| Cl | Br | i-Pr | Me | CF$_3$ |
| Me | H | Me | Me | CF$_3$ |
| Cl | H | Me | Me | CF$_3$ |
| Me | Cl | Me | Me | CF$_3$ |
| Cl | Cl | Me | Me | CF$_3$ |
| Me | Br | Me | Me | CF$_3$ |
| Cl | Br | Me | Me | CF$_3$ |
| Me | H | i-Pr | Me | OCF$_3$ |

TABLE 4-continued

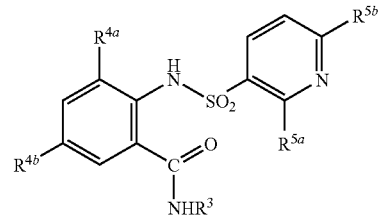

| R<sup>4a</sup> | R<sup>4b</sup> | R<sup>3</sup> | R<sup>5a</sup> | R<sup>5b</sup> |
|---|---|---|---|---|
| Cl | H | i-Pr | Me | OCF$_3$ |
| Me | Cl | i-Pr | Me | OCF$_3$ |
| Cl | Cl | i-Pr | Me | OCF$_3$ |
| Me | Br | i-Pr | Me | OCF$_3$ |
| Cl | Br | i-Pr | Me | OCF$_3$ |
| Me | H | Me | Me | OCF$_3$ |
| Cl | H | Me | Me | OCF$_3$ |
| Me | Cl | Me | Me | OCF$_3$ |
| Cl | Cl | Me | Me | OCF$_3$ |
| Me | Br | Me | Me | OCF$_3$ |
| Cl | Br | Me | Me | OCF$_3$ |
| Me | H | i-Pr | Me | OCH$_2$CF$_3$ |
| Cl | H | i-Pr | Me | OCH$_2$CF$_3$ |
| Me | Cl | i-Pr | Me | OCH$_2$CF$_3$ |
| Cl | Cl | i-Pr | Me | OCH$_2$CF$_3$ |
| Me | Br | i-Pr | Me | OCH$_2$CF$_3$ |
| Cl | Br | i-Pr | Me | OCH$_2$CF$_3$ |
| Me | H | Me | Me | OCH$_2$CF$_3$ |
| Cl | H | Me | Me | OCH$_2$CF$_3$ |
| Me | Cl | Me | Me | OCH$_2$CF$_3$ |
| Cl | Cl | Me | Me | OCH$_2$CF$_3$ |
| Me | Br | Me | Me | OCH$_2$CF$_3$ |
| Cl | Br | Me | Me | OCH$_2$CF$_3$ |
| Me | H | i-Pr | Me | CF(CF$_3$)$_2$ |
| Cl | H | i-Pr | Me | CF(CF$_3$)$_2$ |
| Me | Cl | i-Pr | Me | CF(CF$_3$)$_2$ |
| Cl | Cl | i-Pr | Me | CF(CF$_3$)$_2$ |
| Me | Br | i-Pr | Me | CF(CF$_3$)$_2$ |
| Cl | Br | i-Pr | Me | CF(CF$_3$)$_2$ |
| Me | H | Me | Me | CF(CF$_3$)$_2$ |
| Cl | H | Me | Me | CF(CF$_3$)$_2$ |
| Me | Cl | Me | Me | CF(CF$_3$)$_2$ |
| Cl | Cl | Me | Me | CF(CF$_3$)$_2$ |
| Me | Br | Me | Me | CF(CF$_3$)$_2$ |
| Cl | Br | Me | Me | CF(CF$_3$)$_2$ |

TABLE 5

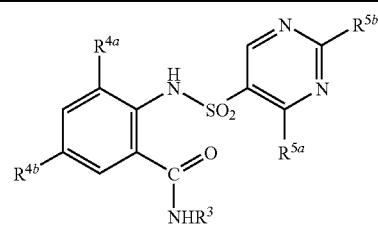

| R<sup>4a</sup> | R<sup>4b</sup> | R<sup>3</sup> | R<sup>5a</sup> | R<sup>5b</sup> |
|---|---|---|---|---|
| Me | H | i-Pr | Me | CF$_3$ |
| Cl | H | i-Pr | Me | CF$_3$ |
| Me | Cl | i-Pr | Me | CF$_3$ |
| Cl | Cl | i-Pr | Me | CF$_3$ |
| Me | Br | i-Pr | Me | CF$_3$ |
| Cl | Br | i-Pr | Me | CF$_3$ |
| Me | H | Me | Me | CF$_3$ |
| Cl | H | Me | Me | CF$_3$ |
| Me | Cl | Me | Me | CF$_3$ |
| Cl | Cl | Me | Me | CF$_3$ |
| Me | Br | Me | Me | CF$_3$ |
| Cl | Br | Me | Me | CF$_3$ |

TABLE 5-continued

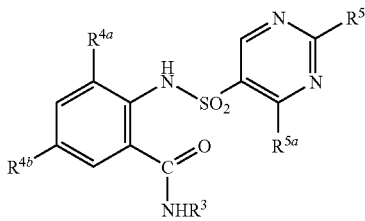

| R4a | R4b | R3 | R5a | R5b |
|---|---|---|---|---|
| Me | H | i-Pr | Me | OCF3 |
| Cl | H | i-Pr | Me | OCF3 |
| Me | Cl | i-Pr | Me | OCF3 |
| Cl | Cl | i-Pr | Me | OCF3 |
| Me | Br | i-Pr | Me | OCF3 |
| Cl | Br | i-Pr | Me | OCF3 |
| Me | H | Me | Me | OCF3 |
| Cl | H | Me | Me | OCF3 |
| Me | Cl | Me | Me | OCF3 |
| Cl | Cl | Me | Me | OCF3 |
| Me | Br | Me | Me | OCF3 |
| Cl | Br | Me | Me | OCF3 |
| Me | H | i-Pr | Me | OCH2CF3 |
| Cl | H | i-Pr | Me | OCH2CF3 |
| Me | Cl | i-Pr | Me | OCH2CF3 |
| Cl | Cl | i-Pr | Me | OCH2CF3 |
| Me | Br | i-Pr | Me | OCH2CF3 |
| Cl | Br | i-Pr | Me | OCH2CF3 |
| Me | H | Me | Me | OCH2CF3 |
| Cl | H | Me | Me | OCH2CF3 |
| Me | Cl | Me | Me | OCH2CF3 |
| Cl | Cl | Me | Me | OCH2CF3 |
| Me | Br | Me | Me | OCH2CF3 |
| Cl | Br | Me | Me | OCH2CF3 |
| Me | H | i-Pr | Me | CF(CF3)2 |
| Cl | H | i-Pr | Me | CF(CF3)2 |
| Me | Cl | i-Pr | Me | CF(CF3)2 |
| Cl | Cl | i-Pr | Me | CF(CF3)2 |
| Me | Br | i-Pr | Me | CF(CF3)2 |
| Cl | Br | i-Pr | Me | CF(CF3)2 |
| Me | H | Me | Me | CF(CF3)2 |
| Cl | H | Me | Me | CF(CF3)2 |
| Me | Cl | Me | Me | CF(CF3)2 |
| Cl | Cl | Me | Me | CF(CF3)2 |
| Me | Br | Me | Me | CF(CF3)2 |
| Cl | Br | Me | Me | CF(CF3)2 |

TABLE 6

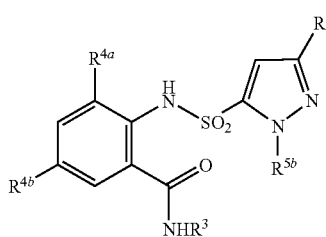

| R4a | R4b | R3 | R5a | R5b |
|---|---|---|---|---|
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |

TABLE 6-continued

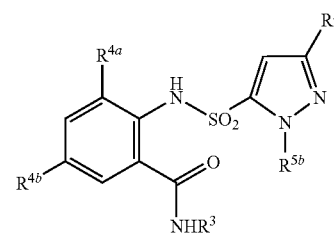

| R4a | R4b | R3 | R5a | R5b |
|---|---|---|---|---|
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |

TABLE 6-continued

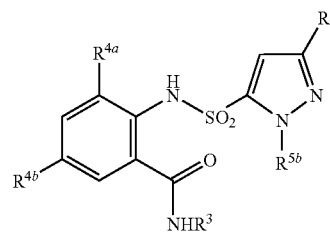

| $R^{4a}$ | $R^{4b}$ | $R^3$ | $R^{5a}$ | $R^{5b}$ |
|---|---|---|---|---|
| Cl | Cl | i-Pr | OCH₂CF₃ | 2-Cl-phenyl |
| Me | Br | i-Pr | OCH₂CF₃ | 2-Cl-phenyl |
| Cl | Br | i-Pr | OCH₂CF₃ | 2-Cl-phenyl |
| Me | H | i-Pr | OCH₂CF₃ | 3-Cl-2-pyridyl |
| Cl | H | i-Pr | OCH₂CF₃ | 3-Cl-2-pyridyl |
| Me | Cl | i-Pr | OCH₂CF₃ | 3-Cl-2-pyridyl |
| Cl | Cl | i-Pr | OCH₂CF₃ | 3-Cl-2-pyridyl |
| Me | Br | i-Pr | OCH₂CF₃ | 3-Cl-2-pyridyl |
| Cl | Br | i-Pr | OCH₂CF₃ | 3-Cl-2-pyridyl |
| Me | H | i-Pr | OCHF₂ | 2-Cl-phenyl |
| Cl | H | i-Pr | OCHF₂ | 2-Cl-phenyl |
| Me | Cl | i-Pr | OCHF₂ | 2-Cl-phenyl |
| Cl | Cl | i-Pr | OCHF₂ | 2-Cl-phenyl |
| Me | Br | i-Pr | OCHF₂ | 2-Cl-phenyl |
| Cl | Br | i-Pr | OCHF₂ | 2-Cl-phenyl |
| Me | H | i-Pr | OCHF₂ | 3-Cl-2-pyridyl |
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | Me | OCH₂CF₃ | 2-Cl-phenyl |
| Cl | H | Me | OCH₂CF₃ | 2-Cl-phenyl |
| Me | Cl | Me | OCH₂CF₃ | 2-Cl-phenyl |
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |
| Me | Cl | Me | OCH₂CF₃ | 3-Cl-2-pyridyl |
| Cl | Cl | Me | OCH₂CF₃ | 3-Cl-2-pyridyl |
| Me | Br | Me | OCH₂CF₃ | 3-Cl-2-pyridyl |
| Cl | Br | Me | OCH₂CF₃ | 3-Cl-2-pyridyl |
| Me | H | Me | OCHF₂ | 2-Cl-phenyl |
| Cl | H | Me | OCHF₂ | 2-Cl-phenyl |
| Me | Cl | Me | OCHF₂ | 2-Cl-phenyl |
| Cl | Cl | Me | OCHF₂ | 2-Cl-phenyl |
| Me | Br | Me | OCHF₂ | 2-Cl-phenyl |
| Cl | Br | Me | OCHF₂ | 2-Cl-phenyl |
| Me | H | Me | OCHF₂ | 3-Cl-2-pyridyl |
| Cl | H | Me | OCHF₂ | 3-Cl-2-pyridyl |
| Me | Cl | Me | OCHF₂ | 3-Cl-2-pyridyl |
| Cl | Cl | Me | OCHF₂ | 3-Cl-2-pyridyl |
| Me | Br | Me | OCHF₂ | 3-Cl-2-pyridyl |
| Cl | Br | Me | OCHF₂ | 3-Cl-2-pyridyl |
| Me | H | i-Pr | CF₃ | 2-Cl-phenyl |
| Cl | H | i-Pr | CF₃ | 2-Cl-phenyl |
| Me | Cl | i-Pr | CF₃ | 2-Cl-phenyl |
| Cl | Cl | i-Pr | CF₃ | 2-Cl-phenyl |
| Me | Br | i-Pr | CF₃ | 2-Cl-phenyl |
| Cl | Br | i-Pr | CF₃ | 2-Cl-phenyl |
| Me | H | i-Pr | CF₃ | 3-Cl-2-pyridyl |
| Cl | H | i-Pr | CF₃ | 3-Cl-2-pyridyl |
| Me | Cl | i-Pr | CF₃ | 3-Cl-2-pyridyl |
| Cl | Cl | i-Pr | CF₃ | 3-Cl-2-pyridyl |
| Me | Br | i-Pr | CF₃ | 3-Cl-2-pyridyl |
| Cl | Br | i-Pr | CF₃ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |

TABLE 6-continued

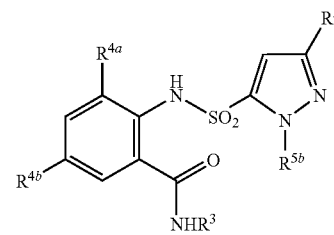

| $R^{4a}$ | $R^{4b}$ | $R^3$ | $R^{5a}$ | $R^{5b}$ |
|---|---|---|---|---|
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF₃ | 2-Cl-phenyl |
| Cl | H | Me | CF₃ | 2-Cl-phenyl |
| Me | Cl | Me | CF₃ | 2-Cl-phenyl |
| Cl | Cl | Me | CF₃ | 2-Cl-phenyl |
| Me | Br | Me | CF₃ | 2-Cl-phenyl |
| Cl | Br | Me | CF₃ | 2-Cl-phenyl |
| Me | H | Me | CF₃ | 3-Cl-2-pyridyl |
| Cl | H | Me | CF₃ | 3-Cl-2-pyridyl |
| Me | Cl | Me | CF₃ | 3-Cl-2-pyridyl |
| Cl | Cl | Me | CF₃ | 3-Cl-2-pyridyl |
| Me | Br | Me | CF₃ | 3-Cl-2-pyridyl |
| Cl | Br | Me | CF₃ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH₂CF₃ | 2-Cl-phenyl |
| Cl | H | i-Pr | OCH₂CF₃ | 2-Cl-phenyl |
| Me | Cl | i-Pr | OCH₂CF₃ | 2-Cl-phenyl |
| Cl | Cl | i-Pr | OCH₂CF₃ | 2-Cl-phenyl |
| Me | Br | i-Pr | OCH₂CF₃ | 2-Cl-phenyl |
| Cl | Br | i-Pr | OCH₂CF₃ | 2-Cl-phenyl |
| Me | H | i-Pr | OCH₂CF₃ | 3-Cl-2-pyridyl |
| Cl | H | i-Pr | OCH₂CF₃ | 3-Cl-2-pyridyl |
| Me | Cl | i-Pr | OCH₂CF₃ | 3-Cl-2-pyridyl |
| Cl | Cl | i-Pr | OCH₂CF₃ | 3-Cl-2-pyridyl |
| Me | Br | i-Pr | OCH₂CF₃ | 3-Cl-2-pyridyl |
| Cl | Br | i-Pr | OCH₂CF₃ | 3-Cl-2-pyridyl |
| Me | H | i-Pr | OCHF₂ | 2-Cl-phenyl |

TABLE 6-continued

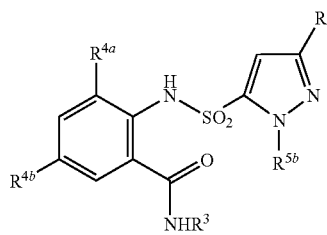

| R⁴ᵃ | R⁴ᵇ | R³ | R⁵ᵃ | R⁵ᵇ |
|---|---|---|---|---|
| Cl | H | i-Pr | OCHF₂ | 2-Cl-phenyl |
| Me | Cl | i-Pr | OCHF₂ | 2-Cl-phenyl |
| Cl | Cl | i-Pr | OCHF₂ | 2-Cl-phenyl |
| Me | Br | i-Pr | OCHF₂ | 2-Cl-phenyl |
| Cl | Br | i-Pr | OCHF₂ | 2-Cl-phenyl |
| Me | H | i-Pr | OCHF₂ | 3-Cl-2-pyridyl |
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |
| Me | Cl | Me | OCH₂CF₃ | 3-Cl-2-pyridyl |
| Cl | Cl | Me | OCH₂CF₃ | 3-Cl-2-pyridyl |
| Me | Br | Me | OCH₂CF₃ | 3-Cl-2-pyridyl |
| Cl | Br | Me | OCH₂CF₃ | 3-Cl-2-pyridyl |
| Me | H | Me | OCHF₂ | 2-Cl-phenyl |
| Cl | H | Me | OCHF₂ | 2-Cl-phenyl |
| Me | Cl | Me | OCHF₂ | 2-Cl-phenyl |
| Cl | Cl | Me | OCHF₂ | 2-Cl-phenyl |
| Me | Br | Me | OCHF₂ | 2-Cl-phenyl |
| Cl | Br | Me | OCHF₂ | 2-Cl-phenyl |
| Me | H | Me | OCHF₂ | 3-Cl-2-pyridyl |
| Cl | H | Me | OCHF₂ | 3-Cl-2-pyridyl |
| Me | Cl | Me | OCHF₂ | 3-Cl-2-pyridyl |
| Cl | Cl | Me | OCHF₂ | 3-Cl-2-pyridyl |
| Me | Br | Me | OCHF₂ | 3-Cl-2-pyridyl |
| Cl | Br | Me | OCHF₂ | 3-Cl-2-pyridyl |

TABLE 7

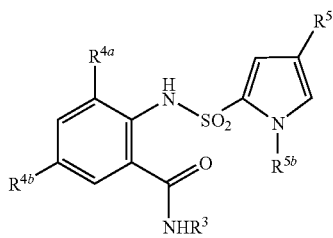

| R⁴ᵃ | R⁴ᵇ | R³ | R⁵ᵃ | R⁵ᵇ |
|---|---|---|---|---|
| Me | H | i-Pr | CF₃ | 2-Cl-phenyl |
| Cl | H | i-Pr | CF₃ | 2-Cl-phenyl |
| Me | Cl | i-Pr | CF₃ | 2-Cl-phenyl |
| Cl | Cl | i-Pr | CF₃ | 2-Cl-phenyl |
| Me | Br | i-Pr | CF₃ | 2-Cl-phenyl |
| Cl | Br | i-Pr | CF₃ | 2-Cl-phenyl |
| Me | H | i-Pr | CF₃ | 3-Cl-2-pyridyl |
| Cl | H | i-Pr | CF₃ | 3-Cl-2-pyridyl |
| Me | Cl | i-Pr | CF₃ | 3-Cl-2-pyridyl |
| Cl | Cl | i-Pr | CF₃ | 3-Cl-2-pyridyl |
| Me | Br | i-Pr | CF₃ | 3-Cl-2-pyridyl |

TABLE 7-continued

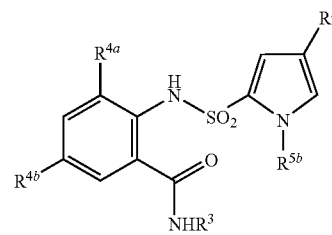

| R⁴ᵃ | R⁴ᵇ | R³ | R⁵ᵃ | R⁵ᵇ |
|---|---|---|---|---|
| Cl | Br | i-Pr | CF₃ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF₃ | 2-Cl-phenyl |
| Cl | H | Me | CF₃ | 2-Cl-phenyl |
| Me | Cl | Me | CF₃ | 2-Cl-phenyl |
| Cl | Cl | Me | CF₃ | 2-Cl-phenyl |
| Me | Br | Me | CF₃ | 2-Cl-phenyl |
| Cl | Br | Me | CF₃ | 2-Cl-phenyl |
| Me | H | Me | CF₃ | 3-Cl-2-pyridyl |
| Cl | H | Me | CF₃ | 3-Cl-2-pyridyl |
| Me | Cl | Me | CF₃ | 3-Cl-2-pyridyl |
| Cl | Cl | Me | CF₃ | 3-Cl-2-pyridyl |
| Me | Br | Me | CF₃ | 3-Cl-2-pyridyl |
| Cl | Br | Me | CF₃ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH₂CF₃ | 2-Cl-phenyl |
| Cl | H | i-Pr | OCH₂CF₃ | 2-Cl-phenyl |
| Me | Cl | i-Pr | OCH₂CF₃ | 2-Cl-phenyl |
| Cl | Cl | i-Pr | OCH₂CF₃ | 2-Cl-phenyl |

TABLE 7-continued

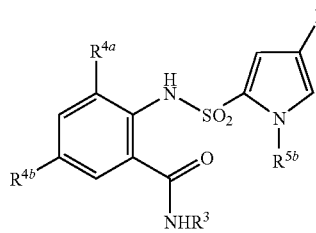

| $R^{4a}$ | $R^{4b}$ | $R^3$ | $R^{5a}$ | $R^{5b}$ |
|---|---|---|---|---|
| Me | Br | i-Pr | OCH$_2$CF$_3$ | 2-Cl-phenyl |
| Cl | Br | i-Pr | OCH$_2$CF$_3$ | 2-Cl-phenyl |
| Me | H | i-Pr | OCH$_2$CF$_3$ | 3-Cl-2-pyridyl |
| Cl | H | i-Pr | OCH$_2$CF$_3$ | 3-Cl-2-pyridyl |
| Me | Cl | i-Pr | OCH$_2$CF$_3$ | 3-Cl-2-pyridyl |
| Cl | Cl | i-Pr | OCH$_2$CF$_3$ | 3-Cl-2-pyridyl |
| Me | Br | i-Pr | OCH$_2$CF$_3$ | 3-Cl-2-pyridyl |
| Cl | Br | i-Pr | OCH$_2$CF$_3$ | 3-Cl-2-pyridyl |
| Me | H | i-Pr | OCHF$_2$ | 2-Cl-phenyl |
| Cl | H | i-Pr | OCHF$_2$ | 2-Cl-phenyl |
| Me | Cl | i-Pr | OCHF$_2$ | 2-Cl-phenyl |
| Cl | Cl | i-Pr | OCHF$_2$ | 2-Cl-phenyl |
| Me | Br | i-Pr | OCHF$_2$ | 2-Cl-phenyl |
| Cl | Br | i-Pr | OCHF$_2$ | 2-Cl-phenyl |
| Me | H | i-Pr | OCHF$_2$ | 2-Cl-2-pyridyl |
| Cl | H | i-Pr | OCHF$_2$ | 3-Cl-2-pyridyl |
| Me | Cl | i-Pr | OCHF$_2$ | 3-Cl-2-pyridyl |
| Cl | Cl | i-Pr | OCHF$_2$ | 3-Cl-2-pyridyl |
| Me | Br | i-Pr | OCHF$_2$ | 3-Cl-2-pyridyl |
| Cl | Br | i-Pr | OCHF$_2$ | 3-Cl-2-pyridyl |
| Me | H | Me | OCH$_2$CF$_3$ | 2-Cl-phenyl |
| Cl | H | Me | OCH$_2$CF$_3$ | 2-Cl-phenyl |
| Me | Cl | Me | OCH$_2$CF$_3$ | 2-Cl-phenyl |
| Cl | Cl | Me | OCH$_2$CF$_3$ | 2-Cl-phenyl |
| Me | Br | Me | OCH$_2$CF$_3$ | 2-Cl-phenyl |
| Cl | Br | Me | OCH$_2$CF$_3$ | 2-Cl-phenyl |
| Me | H | Me | OCH$_2$CF$_3$ | 3-Cl-2-pyridyl |
| Cl | H | Me | OCH$_2$CF$_3$ | 3-Cl-2-pyridyl |
| Me | Cl | Me | OCH$_2$CF$_3$ | 3-Cl-2-pyridyl |
| Cl | Cl | Me | OCH$_2$CF$_3$ | 3-Cl-2-pyridyl |
| Me | Br | Me | OCH$_2$CF$_3$ | 3-Cl-2-pyridyl |
| Cl | Br | Me | OCH$_2$CF$_3$ | 3-Cl-2-pyridyl |
| Me | H | Me | OCHF$_2$ | 2-Cl-phenyl |
| Cl | H | Me | OCHF$_2$ | 2-Cl-phenyl |
| Me | Cl | Me | OCHF$_2$ | 2-Cl-phenyl |
| Cl | Cl | Me | OCHF$_2$ | 2-Cl-phenyl |
| Me | Br | Me | OCHF$_2$ | 2-Cl-phenyl |
| Cl | Br | Me | OCHF$_2$ | 2-Cl-phenyl |
| Me | H | Me | OCHF$_2$ | 3-Cl-2-pyridyl |
| Cl | H | Me | OCHF$_2$ | 3-Cl-2-pyridyl |
| Me | Cl | Me | OCHF$_2$ | 3-Cl-2-pyridyl |
| Cl | Cl | Me | OCHF$_2$ | 3-Cl-2-pyridyl |
| Me | Br | Me | OCHF$_2$ | 3-Cl-2-pyridyl |
| Cl | Br | Me | OCHF$_2$ | 3-Cl-2-pyridyl |
| Me | H | i-Pr | CF$_3$ | 2-Cl-phenyl |
| Cl | H | i-Pr | CF$_3$ | 2-Cl-phenyl |
| Me | Cl | i-Pr | CF$_3$ | 2-Cl-phenyl |
| Cl | Cl | i-Pr | CF$_3$ | 2-Cl-phenyl |
| Me | Br | i-Pr | CF$_3$ | 2-Cl-phenyl |
| Cl | Br | i-Pr | CF$_3$ | 2-Cl-phenyl |
| Me | H | i-Pr | CF$_3$ | 3-Cl-2-pyridyl |
| Cl | H | i-Pr | CF$_3$ | 3-Cl-2-pyridyl |
| Me | Cl | i-Pr | CF$_3$ | 3-Cl-2-pyridyl |
| Cl | Cl | i-Pr | CF$_3$ | 3-Cl-2-pyridyl |
| Me | Br | i-Pr | CF$_3$ | 3-Cl-2-pyridyl |
| Cl | Br | i-Pr | CF$_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |

TABLE 7-continued

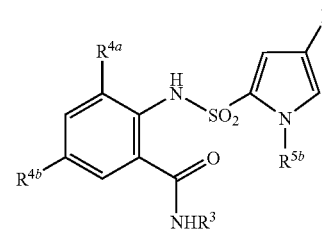

| $R^{4a}$ | $R^{4b}$ | $R^3$ | $R^{5a}$ | $R^{5b}$ |
|---|---|---|---|---|
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF$_3$ | 2-Cl-phenyl |
| Cl | H | Me | CF$_3$ | 2-Cl-phenyl |
| Me | Cl | Me | CF$_3$ | 2-Cl-phenyl |
| Cl | Cl | Me | CF$_3$ | 2-Cl-phenyl |
| Me | Br | Me | CF$_3$ | 2-Cl-phenyl |
| Cl | Br | Me | CF$_3$ | 2-Cl-phenyl |
| Me | H | Me | CF$_3$ | 3-Cl-2-pyridyl |
| Cl | H | Me | CF$_3$ | 3-Cl-2-pyridyl |
| Me | Cl | Me | CF$_3$ | 3-Cl-2-pyridyl |
| Cl | Cl | Me | CF$_3$ | 3-Cl-2-pyridyl |
| Me | Br | Me | CF$_3$ | 3-Cl-2-pyridyl |
| Cl | Br | Me | CF$_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH$_2$CF$_3$ | 2-Cl-phenyl |
| Cl | H | i-Pr | OCH$_2$CF$_3$ | 2-Cl-phenyl |
| Me | Cl | i-Pr | OCH$_2$CF$_3$ | 2-Cl-phenyl |
| Cl | Cl | i-Pr | OCH$_2$CF$_3$ | 2-Cl-phenyl |
| Me | Br | i-Pr | OCH$_2$CF$_3$ | 2-Cl-phenyl |
| Cl | Br | i-Pr | OCH$_2$CF$_3$ | 2-Cl-phenyl |
| Me | H | i-Pr | OCH$_2$CF$_3$ | 3-Cl-2-pyridyl |
| Cl | H | i-Pr | OCH$_2$CF$_3$ | 3-Cl-2-pyridyl |
| Me | Cl | i-Pr | OCH$_2$CF$_3$ | 3-Cl-2-pyridyl |
| Cl | Cl | i-Pr | OCH$_2$CF$_3$ | 3-Cl-2-pyridyl |
| Me | Br | i-Pr | OCH$_2$CF$_3$ | 3-Cl-2-pyridyl |
| Cl | Br | i-Pr | OCH$_2$CF$_3$ | 3-Cl-2-pyridyl |
| Me | H | i-Pr | OCHF$_2$ | 2-Cl-phenyl |
| Cl | H | i-Pr | OCHF$_2$ | 2-Cl-phenyl |

TABLE 7-continued

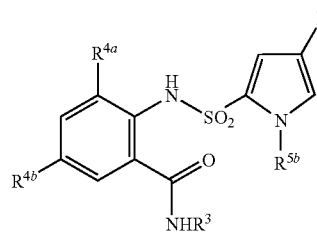

| R4a | R4b | R3 | R5a | R5b |
|---|---|---|---|---|
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |

TABLE 8

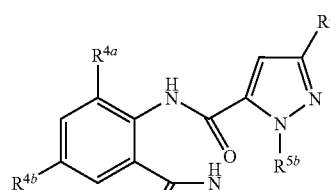

| R4a | R4b | R3 | R5a | R5b |
|---|---|---|---|---|
| B is NOMe | | | | |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |

TABLE 8-continued

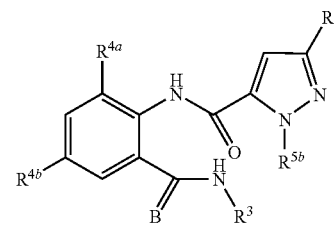

| R4a | R4b | R3 | R5a | R5b |
|---|---|---|---|---|
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |

TABLE 8-continued

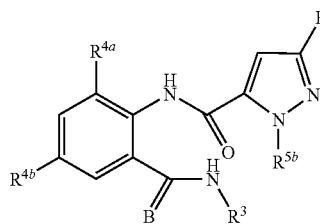

| R4a | R4b | R3 | R5a | R5b |
|---|---|---|---|---|
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | Me | OCH2CF3 | 2-Cl-phenyl |
| Cl | H | Me | OCH2CF3 | 2-Cl-phenyl |
| Me | Cl | Me | OCH2CF3 | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |
| B is NNMe2 | | | | |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |

TABLE 8-continued

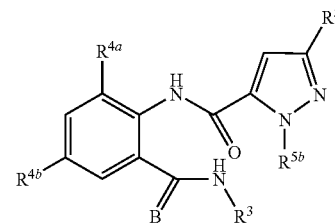

| R4a | R4b | R3 | R5a | R5b |
|---|---|---|---|---|
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |

TABLE 8-continued

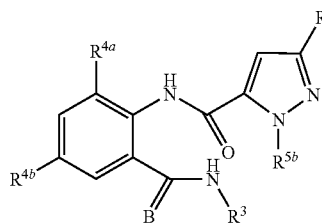

| $R^{4a}$ | $R^{4b}$ | $R^3$ | $R^{5a}$ | $R^{5b}$ |
|---|---|---|---|---|
| Cl | Br | i-Pr | OCH$_2$CF$_3$ | 3-Cl-2-pyridyl |
| Me | H | i-Pr | OCHF$_2$ | 2-Cl-phenyl |
| Cl | H | i-Pr | OCHF$_2$ | 2-Cl-phenyl |
| Me | Cl | i-Pr | OCHF$_2$ | 2-Cl-phenyl |
| Cl | Cl | i-Pr | OCHF$_2$ | 2-Cl-phenyl |
| Me | Br | i-Pr | OCHF$_2$ | 2-Cl-phenyl |
| Cl | Br | i-Pr | OCHF$_2$ | 2-Cl-phenyl |
| Me | H | i-Pr | OCHF$_2$ | 3-Cl-2-pyridyl |
| Cl | H | i-Pr | OCHF$_2$ | 3-Cl-2-pyridyl |
| Me | Cl | i-Pr | OCHF$_2$ | 3-Cl-2-pyridyl |
| Cl | Cl | i-Pr | OCHF$_2$ | 3-Cl-2-pyridyl |
| Me | Br | i-Pr | OCHF$_2$ | 3-Cl-2-pyridyl |
| Cl | Br | i-Pr | OCHF$_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH$_2$CF$_3$ | 2-Cl-phenyl |
| Me | Br | Me | OCH$_2$CF$_3$ | 2-Cl-phenyl |
| Cl | Br | Me | OCH$_2$CF$_3$ | 2-Cl-phenyl |
| Me | H | Me | OCH$_2$CF$_3$ | 3-Cl-2-pyridyl |
| Cl | H | Me | OCH$_2$CF$_3$ | 3-Cl-2-pyridyl |
| Me | Cl | Me | OCH$_2$CF$_3$ | 3-Cl-2-pyridyl |
| Cl | Cl | Me | OCH$_2$CF$_3$ | 3-Cl-2-pyridyl |
| Me | Br | Me | OCH$_2$CF$_3$ | 3-Cl-2-pyridyl |
| Cl | Br | Me | OCH$_2$CF$_3$ | 3-Cl-2-pyridyl |
| Me | H | Me | OCHF$_2$ | 2-Cl-phenyl |
| Cl | H | Me | OCHF$_2$ | 2-Cl-phenyl |
| Me | Cl | Me | OCHF$_2$ | 2-Cl-phenyl |
| Cl | Cl | Me | OCHF$_2$ | 2-Cl-phenyl |
| Me | Br | Me | OCHF$_2$ | 2-Cl-phenyl |
| Cl | Br | Me | OCHF$_2$ | 2-Cl-phenyl |
| Me | H | Me | OCHF$_2$ | 3-Cl-2-pyridyl |
| Cl | H | Me | OCHF$_2$ | 3-Cl-2-pyridyl |
| Me | Cl | Me | OCHF$_2$ | 3-Cl-2-pyridyl |
| Cl | Cl | Me | OCHF$_2$ | 3-Cl-2-pyridyl |
| Me | Br | Me | OCHF$_2$ | 3-Cl-2-pyridyl |
| Cl | Br | Me | OCHF$_2$ | 3-Cl-2-pyridyl |
| B is S=O | | | | |
| Me | H | i-Pr | CF$_3$ | 2-Cl-phenyl |
| Cl | H | i-Pr | CF$_3$ | 2-Cl-phenyl |
| Me | Cl | i-Pr | CF$_3$ | 2-Cl-phenyl |
| Cl | Cl | i-Pr | CF$_3$ | 2-Cl-phenyl |
| Me | Br | i-Pr | CF$_3$ | 2-Cl-phenyl |
| Cl | Br | i-Pr | CF$_3$ | 2-Cl-phenyl |
| Me | H | i-Pr | CF$_3$ | 3-Cl-2-pyridyl |
| Cl | H | i-Pr | CF$_3$ | 3-Cl-2-pyridyl |
| Me | Cl | i-Pr | CF$_3$ | 3-Cl-2-pyridyl |
| Cl | Cl | i-Pr | CF$_3$ | 3-Cl-2-pyridyl |
| Me | Br | i-Pr | CF$_3$ | 3-Cl-2-pyridyl |
| Cl | Br | i-Pr | CF$_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |

TABLE 8-continued

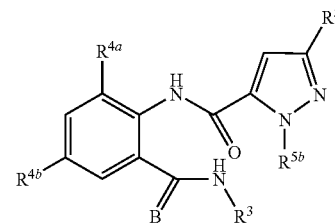

| $R^{4a}$ | $R^{4b}$ | $R^3$ | $R^{5a}$ | $R^{5b}$ |
|---|---|---|---|---|
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF$_3$ | 2-Cl-phenyl |
| Cl | H | Me | CF$_3$ | 2-Cl-phenyl |
| Me | Cl | Me | CF$_3$ | 2-Cl-phenyl |
| Cl | Cl | Me | CF$_3$ | 2-Cl-phenyl |
| Me | Br | Me | CF$_3$ | 2-Cl-phenyl |
| Cl | Br | Me | CF$_3$ | 2-Cl-phenyl |
| Me | H | Me | CF$_3$ | 3-Cl-2-pyridyl |
| Cl | H | Me | CF$_3$ | 3-Cl-2-pyridyl |
| Me | Cl | Me | CF$_3$ | 3-Cl-2-pyridyl |
| Cl | Cl | Me | CF$_3$ | 3-Cl-2-pyridyl |
| Me | Br | Me | CF$_3$ | 3-Cl-2-pyridyl |
| Cl | Br | Me | CF$_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH$_2$CF$_3$ | 2-Cl-phenyl |
| Cl | H | i-Pr | OCH$_2$CF$_3$ | 2-Cl-phenyl |
| Me | Cl | i-Pr | OCH$_2$CF$_3$ | 2-Cl-phenyl |
| Cl | Cl | i-Pr | OCH$_2$CF$_3$ | 2-Cl-phenyl |
| Me | Br | i-Pr | OCH$_2$CF$_3$ | 2-Cl-phenyl |
| Cl | Br | i-Pr | OCH$_2$CF$_3$ | 2-Cl-phenyl |
| Me | H | i-Pr | OCH$_2$CF$_3$ | 3-Cl-2-pyridyl |
| Cl | H | i-Pr | OCH$_2$CF$_3$ | 3-Cl-2-pyridyl |
| Me | Cl | i-Pr | OCH$_2$CF$_3$ | 3-Cl-2-pyridyl |
| Cl | Cl | i-Pr | OCH$_2$CF$_3$ | 3-Cl-2-pyridyl |
| Me | Br | i-Pr | OCH$_2$CF$_3$ | 3-Cl-2-pyridyl |
| Cl | Br | i-Pr | OCH$_2$CF$_3$ | 3-Cl-2-pyridyl |
| Me | H | i-Pr | OCHF$_2$ | 2-Cl-phenyl |
| Cl | H | i-Pr | OCHF$_2$ | 2-Cl-phenyl |
| Me | Cl | i-Pr | OCHF$_2$ | 2-Cl-phenyl |
| Cl | Cl | i-Pr | OCHF$_2$ | 2-Cl-phenyl |
| Me | Br | i-Pr | OCHF$_2$ | 2-Cl-phenyl |
| Cl | Br | i-Pr | OCHF$_2$ | 2-Cl-phenyl |
| Me | H | i-Pr | OCHF$_2$ | 3-Cl-2-pyridyl |

TABLE 8-continued

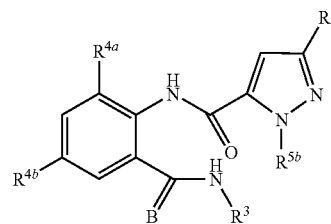

| R⁴ᵃ | R⁴ᵇ | R³ | R⁵ᵃ | R⁵ᵇ |
|---|---|---|---|---|
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | Me | OCH₂CF₃ | 2-Cl-phenyl |
| Cl | H | Me | OCH₂CF₃ | 2-Cl-phenyl |
| Me | Cl | Me | OCH₂CF₃ | 2-Cl-phenyl |
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |
| Me | Cl | Me | OCH₂CF₃ | 3-Cl-2-pyridyl |
| Cl | Cl | Me | OCH₂CF₃ | 3-Cl-2-pyridyl |
| Me | Br | Me | OCH₂CF₃ | 3-Cl-2-pyridyl |
| Cl | Br | Me | OCH₂CF₃ | 3-Cl-2-pyridyl |
| Me | H | Me | OCHF₂ | 2-Cl-phenyl |
| Cl | H | Me | OCHF₂ | 2-Cl-phenyl |
| Me | Cl | Me | OCHF₂ | 2-Cl-phenyl |
| Cl | Cl | Me | OCHF₂ | 2-Cl-phenyl |
| Me | Br | Me | OCHF₂ | 2-Cl-phenyl |
| Cl | Br | Me | OCHF₂ | 2-Cl-phenyl |
| Me | H | Me | OCHF₂ | 3-Cl-2-pyridyl |
| Cl | H | Me | OCHF₂ | 3-Cl-2-pyridyl |
| Me | Cl | Me | OCHF₂ | 3-Cl-2-pyridyl |
| Cl | Cl | Me | OCHF₂ | 3-Cl-2-pyridyl |
| Me | Br | Me | OCHF₂ | 3-Cl-2-pyridyl |
| Cl | Br | Me | OCHF₂ | 3-Cl-2-pyridyl |

B is N—CN

| R⁴ᵃ | R⁴ᵇ | R³ | R⁵ᵃ | R⁵ᵇ |
|---|---|---|---|---|
| Me | H | i-Pr | CF₃ | 2-Cl-phenyl |
| Cl | H | i-Pr | CF₃ | 2-Cl-phenyl |
| Me | Cl | i-Pr | CF₃ | 2-Cl-phenyl |
| Cl | Cl | i-Pr | CF₃ | 2-Cl-phenyl |
| Me | Br | i-Pr | CF₃ | 2-Cl-phenyl |
| Cl | Br | i-Pr | CF₃ | 2-Cl-phenyl |
| Me | H | i-Pr | CF₃ | 3-Cl-2-pyridyl |
| Cl | H | i-Pr | CF₃ | 3-Cl-2-pyridyl |
| Me | Cl | i-Pr | CF₃ | 3-Cl-2-pyridyl |
| Cl | Cl | i-Pr | CF₃ | 3-Cl-2-pyridyl |
| Me | Br | i-Pr | CF₃ | 3-Cl-2-pyridyl |
| Cl | Br | i-Pr | CF₃ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |

TABLE 8-continued

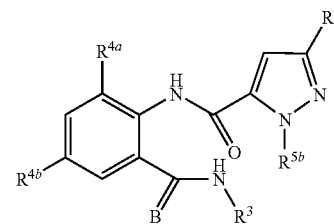

| R⁴ᵃ | R⁴ᵇ | R³ | R⁵ᵃ | R⁵ᵇ |
|---|---|---|---|---|
| Me | Br | i-Pr | Cl | 3-Cl-2-pyridyl |
| Cl | Br | i-Pr | Cl | 3-Cl-2-pyridyl |
| Me | H | Me | CF₃ | 2-Cl-phenyl |
| Cl | H | Me | CF₃ | 2-Cl-phenyl |
| Me | Cl | Me | CF₃ | 2-Cl-phenyl |
| Cl | Cl | Me | CF₃ | 2-Cl-phenyl |
| Me | Br | Me | CF₃ | 2-Cl-phenyl |
| Cl | Br | Me | CF₃ | 2-Cl-phenyl |
| Me | H | Me | CF₃ | 3-Cl-2-pyridyl |
| Cl | H | Me | CF₃ | 3-Cl-2-pyridyl |
| Me | Cl | Me | CF₃ | 3-Cl-2-pyridyl |
| Cl | Cl | Me | CF₃ | 3-Cl-2-pyridyl |
| Me | Br | Me | CF₃ | 3-Cl-2-pyridyl |
| Cl | Br | Me | CF₃ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH₂CF₃ | 2-Cl-phenyl |
| Cl | H | i-Pr | OCH₂CF₃ | 2-Cl-phenyl |
| Me | Cl | i-Pr | OCH₂CF₃ | 2-Cl-phenyl |
| Cl | Cl | i-Pr | OCH₂CF₃ | 2-Cl-phenyl |
| Me | Br | i-Pr | OCH₂CF₃ | 2-Cl-phenyl |
| Cl | Br | i-Pr | OCH₂CF₃ | 2-Cl-phenyl |
| Me | H | i-Pr | OCH₂CF₃ | 3-Cl-2-pyridyl |
| Cl | H | i-Pr | OCH₂CF₃ | 3-Cl-2-pyridyl |
| Me | Cl | i-Pr | OCH₂CF₃ | 3-Cl-2-pyridyl |
| Cl | Cl | i-Pr | OCH₂CF₃ | 3-Cl-2-pyridyl |
| Me | Br | i-Pr | OCH₂CF₃ | 3-Cl-2-pyridyl |
| Cl | Br | i-Pr | OCH₂CF₃ | 3-Cl-2-pyridyl |
| Me | H | i-Pr | OCHF₂ | 2-Cl-phenyl |
| Cl | H | i-Pr | OCHF₂ | 2-Cl-phenyl |
| Me | Cl | i-Pr | OCHF₂ | 2-Cl-phenyl |
| Cl | Cl | i-Pr | OCHF₂ | 2-Cl-phenyl |
| Me | Br | i-Pr | OCHF₂ | 2-Cl-phenyl |
| Cl | Br | i-Pr | OCHF₂ | 2-Cl-phenyl |
| Me | H | i-Pr | OCHF₂ | 3-Cl-2-pyridyl |
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |

TABLE 8-continued

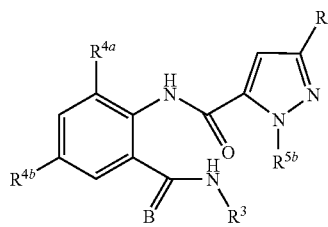

| R4a | R4b | R3 | R5a | R5b |
|---|---|---|---|---|
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |
| Me | Cl | Me | OCH₂CF₃ | 3-Cl-2-pyridyl |
| Cl | Cl | Me | OCH₂CF₃ | 3-Cl-2-pyridyl |
| Me | Br | Me | OCH₂CF₃ | 3-Cl-2-pyridyl |
| Cl | Br | Me | OCH₂CF₃ | 3-Cl-2-pyridyl |
| Me | H | Me | OCHF₂ | 2-Cl-phenyl |
| Cl | H | Me | OCHF₂ | 2-Cl-phenyl |
| Me | Cl | Me | OCHF₂ | 2-Cl-phenyl |
| Cl | Cl | Me | OCHF₂ | 2-Cl-phenyl |
| Me | Br | Me | OCHF₂ | 2-Cl-phenyl |
| Cl | Br | Me | OCHF₂ | 2-Cl-phenyl |
| Me | H | Me | OCHF₂ | 3-Cl-2-pyridyl |
| Cl | H | Me | OCHF₂ | 3-Cl-2-pyridyl |
| Me | Cl | Me | OCHF₂ | 3-Cl-2-pyridyl |
| Cl | Cl | Me | OCHF₂ | 3-Cl-2-pyridyl |
| Me | Br | Me | OCHF₂ | 3-Cl-2-pyridyl |
| Cl | Br | Me | OCHF₂ | 3-Cl-2-pyridyl |
| B is N—NO₂ | | | | |
| Me | H | i-Pr | CF₃ | 2-Cl-phenyl |
| Cl | H | i-Pr | CF₃ | 2-Cl-phenyl |
| Me | Cl | i-Pr | CF₃ | 2-Cl-phenyl |
| Cl | Cl | i-Pr | CF₃ | 2-Cl-phenyl |
| Me | Br | i-Pr | CF₃ | 2-Cl-phenyl |
| Cl | Br | i-Pr | CF₃ | 2-Cl-phenyl |
| Me | H | i-Pr | CF₃ | 3-Cl-2-pyridyl |
| Cl | H | i-Pr | CF₃ | 3-Cl-2-pyridyl |
| Me | Cl | i-Pr | CF₃ | 3-Cl-2-pyridyl |
| Cl | Cl | i-Pr | CF₃ | 3-Cl-2-pyridyl |
| Me | Br | i-Pr | CF₃ | 3-Cl-2-pyridyl |
| Cl | Br | i-Pr | CF₃ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF₃ | 2-Cl-phenyl |
| Cl | H | Me | CF₃ | 2-Cl-phenyl |
| Me | Cl | Me | CF₃ | 2-Cl-phenyl |
| Cl | Cl | Me | CF₃ | 2-Cl-phenyl |
| Me | Br | Me | CF₃ | 2-Cl-phenyl |
| Cl | Br | Me | CF₃ | 2-Cl-phenyl |

TABLE 8-continued

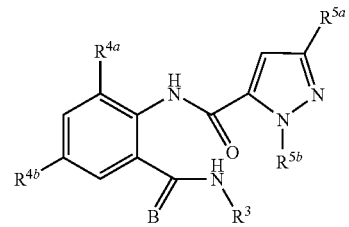

| R4a | R4b | R3 | R5a | R5b |
|---|---|---|---|---|
| Me | H | Me | CF₃ | 3-Cl-2-pyridyl |
| Cl | H | Me | CF₃ | 3-Cl-2-pyridyl |
| Me | Cl | Me | CF₃ | 3-Cl-2-pyridyl |
| Cl | Cl | Me | CF₃ | 3-Cl-2-pyridyl |
| Me | Br | Me | CF₃ | 3-Cl-2-pyridyl |
| Cl | Br | Me | CF₃ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-CJ-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH₂CF₃ | 2-Cl-phenyl |
| Cl | H | i-Pr | OCH₂CF₃ | 2-Cl-phenyl |
| Me | Cl | i-Pr | OCH₂CF₃ | 2-Cl-phenyl |
| Cl | Cl | i-Pr | OCH₂CF₃ | 2-Cl-phenyl |
| Me | Br | i-Pr | OCH₂CF₃ | 2-Cl-phenyl |
| Cl | Br | i-Pr | OCH₂CF₃ | 2-Cl-phenyl |
| Me | H | i-Pr | OCH₂CF₃ | 3-Cl-2-pyridyl |
| Cl | H | i-Pr | OCH₂CF₃ | 3-Cl-2-pyridyl |
| Me | Cl | i-Pr | OCH₂CF₃ | 3-Cl-2-pyridyl |
| Cl | Cl | i-Pr | OCH₂CF₃ | 3-Cl-2-pyridyl |
| Me | Br | i-Pr | OCH₂CF₃ | 3-Cl-2-pyridyl |
| Cl | Br | i-Pr | OCH₂CF₃ | 3-Cl-2-pyridyl |
| Me | H | i-Pr | OCHF₂ | 2-Cl-phenyl |
| Cl | H | i-Pr | OCHF₂ | 2-Cl-phenyl |
| Me | Cl | i-Pr | OCHF₂ | 2-Cl-phenyl |
| Cl | Cl | i-Pr | OCHF₂ | 2-Cl-phenyl |
| Me | Br | i-Pr | OCHF₂ | 2-Cl-phenyl |
| Cl | Br | i-Pr | OCHF₂ | 2-Cl-phenyl |
| Me | H | i-Pr | OCHF₂ | 3-Cl-2-pyridyl |
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | Me | OCH₂CF₃ | 2-Cl-phenyl |
| Cl | H | Me | OCH₂CF₃ | 2-Cl-phenyl |
| Me | Cl | Me | OCH₂CF₃ | 2-Cl-phenyl |
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |
| Me | Cl | Me | OCH₂CF₃ | 3-Cl-2-pyridyl |
| Cl | Cl | Me | OCH₂CF₃ | 3-Cl-2-pyridyl |
| Me | Br | Me | OCH₂CF₃ | 3-Cl-2-pyridyl |

TABLE 8-continued

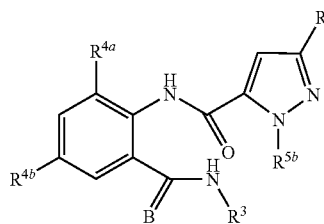

| $R^{4a}$ | $R^{4b}$ | $R^3$ | $R^{5a}$ | $R^{5b}$ |
|---|---|---|---|---|
| Cl | Br | Me | OCH$_2$CF$_3$ | 3-Cl-2-pyridyl |
| Me | H | Me | OCHF$_2$ | 2-Cl-phenyl |
| Cl | H | Me | OCHF$_2$ | 2-Cl-phenyl |
| Me | Cl | Me | OCHF$_2$ | 2-Cl-phenyl |
| Cl | Cl | Me | OCHF$_2$ | 2-Cl-phenyl |
| Me | Br | Me | OCHF$_2$ | 2-Cl-phenyl |
| Cl | Br | Me | OCHF$_2$ | 2-Cl-phenyl |
| Me | H | Me | OCHF$_2$ | 3-Cl-2-pyridyl |
| Cl | H | Me | OCHF$_2$ | 3-Cl-2-pyridyl |
| Me | Cl | Me | OCHF$_2$ | 3-Cl-2-pyridyl |
| Cl | Cl | Me | OCHF$_2$ | 3-Cl-2-pyridyl |
| Me | Br | Me | OCHF$_2$ | 3-Cl-2-pyridyl |
| Cl | Br | Me | OCHF$_2$ | 3-Cl-2-pyridyl |
| B is NMe | | | | |
| Me | H | i-Pr | CF$_3$ | 2-Cl-phenyl |
| Cl | H | i-Pr | CF$_3$ | 2-Cl-phenyl |
| Me | Cl | i-Pr | CF$_3$ | 2-Cl-phenyl |
| Cl | Cl | i-Pr | CF$_3$ | 2-Cl-phenyl |
| Me | Br | i-Pr | CF$_3$ | 2-Cl-phenyl |
| Cl | Br | i-Pr | CF$_3$ | 2-Cl-phenyl |
| Me | H | i-Pr | CF$_3$ | 3-Cl-2-pyridyl |
| Cl | H | i-Pr | CF$_3$ | 3-Cl-2-pyridyl |
| Me | Cl | i-Pr | CF$_3$ | 3-Cl-2-pyridyl |
| Cl | Cl | i-Pr | CF$_3$ | 3-Cl-2-pyridyl |
| Me | Br | i-Pr | CF$_3$ | 3-Cl-2-pyridyl |
| Cl | Br | i-Pr | CF$_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF$_3$ | 2-Cl-phenyl |
| Cl | H | Me | CF$_3$ | 2-Cl-phenyl |
| Me | Cl | Me | CF$_3$ | 2-Cl-phenyl |
| Cl | Cl | Me | CF$_3$ | 2-Cl-phenyl |
| Me | Br | Me | CF$_3$ | 2-Cl-phenyl |
| Cl | Br | Me | CF$_3$ | 2-Cl-phenyl |
| Me | H | Me | CF$_3$ | 3-Cl-2-pyridyl |
| Cl | H | Me | CF$_3$ | 3-Cl-2-pyridyl |
| Me | Cl | Me | CF$_3$ | 3-Cl-2-pyridyl |
| Cl | Cl | Me | CF$_3$ | 3-Cl-2-pyridyl |
| Me | Br | Me | CF$_3$ | 3-Cl-2-pyridyl |
| Cl | Br | Me | CF$_3$ | 3-Cl-2-pyridyl |
| Me | H | Me | Br | 2-Cl-phenyl |
| Cl | H | Me | Br | 2-Cl-phenyl |

TABLE 8-continued

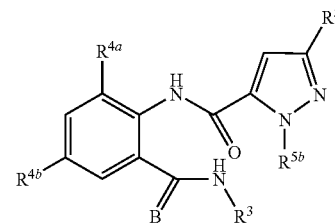

| $R^{4a}$ | $R^{4b}$ | $R^3$ | $R^{5a}$ | $R^{5b}$ |
|---|---|---|---|---|
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH$_2$CF$_3$ | 2-Cl-phenyl |
| Cl | H | i-Pr | OCH$_2$CF$_3$ | 2-Cl-phenyl |
| Me | Cl | i-Pr | OCH$_2$CF$_3$ | 2-Cl-phenyl |
| Cl | Cl | i-Pr | OCH$_2$CF$_3$ | 2-Cl-phenyl |
| Me | Br | i-Pr | OCH$_2$CF$_3$ | 2-Cl-phenyl |
| Cl | Br | i-Pr | OCH$_2$CF$_3$ | 2-Cl-phenyl |
| Me | H | i-Pr | OCH$_2$CF$_3$ | 3-Cl-2-pyridyl |
| Cl | H | i-Pr | OCH$_2$CF$_3$ | 3-Cl-2-pyridyl |
| Me | Cl | i-Pr | OCH$_2$CF$_3$ | 3-Cl-2-pyridyl |
| Cl | Cl | i-Pr | OCH$_2$CF$_3$ | 3-Cl-2-pyridyl |
| Me | Br | i-Pr | OCH$_2$CF$_3$ | 3-Cl-2-pyridyl |
| Cl | Br | i-Pr | OCH$_2$CF$_3$ | 3-Cl-2-pyridyl |
| Me | H | i-Pr | OCHF$_2$ | 2-Cl-phenyl |
| Cl | H | i-Pr | OCHF$_2$ | 2-Cl-phenyl |
| Me | Cl | i-Pr | OCHF$_2$ | 2-Cl-phenyl |
| Cl | Cl | i-Pr | OCHF$_2$ | 2-Cl-phenyl |
| Me | Br | i-Pr | OCHF$_2$ | 2-Cl-phenyl |
| Cl | Br | i-Pr | OCHF$_2$ | 2-Cl-phenyl |
| Me | H | i-Pr | OCHF$_2$ | 3-Cl-2-pyridyl |
| Cl | H | i-Pr | OCHF$_2$ | 3-Cl-2-pyridyl |
| Me | Cl | i-Pr | OCHF$_2$ | 3-Cl-2-pyridyl |
| Cl | Cl | i-Pr | OCHF$_2$ | 3-Cl-2-pyridyl |
| Me | Br | i-Pr | OCHF$_2$ | 3-Cl-2-pyridyl |
| Cl | Br | i-Pr | OCHF$_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH$_2$CF$_3$ | 2-Cl-phenyl |
| Me | Br | Me | OCH$_2$CF$_3$ | 2-Cl-phenyl |
| Cl | Br | Me | OCH$_2$CF$_3$ | 2-Cl-phenyl |
| Me | H | Me | OCH$_2$CF$_3$ | 3-Cl-2-pyridyl |
| Cl | H | Me | OCH$_2$CF$_3$ | 3-Cl-2-pyridyl |
| Me | Cl | Me | OCH$_2$CF$_3$ | 3-Cl-2-pyridyl |
| Cl | Cl | Me | OCH$_2$CF$_3$ | 3-Cl-2-pyridyl |
| Me | Br | Me | OCH$_2$CF$_3$ | 3-Cl-2-pyridyl |
| Cl | Br | Me | OCH$_2$CF$_3$ | 3-Cl-2-pyridyl |
| Me | H | Me | OCHF$_2$ | 2-Cl-phenyl |
| Cl | H | Me | OCHF$_2$ | 2-Cl-phenyl |
| Me | Cl | Me | OCHF$_2$ | 2-Cl-phenyl |
| Cl | Cl | Me | OCHF$_2$ | 2-Cl-phenyl |
| Me | Br | Me | OCHF$_2$ | 2-Cl-phenyl |
| Cl | Br | Me | OCHF$_2$ | 2-Cl-phenyl |
| Me | H | Me | OCHF$_2$ | 3-Cl-2-pyridyl |

TABLE 8-continued

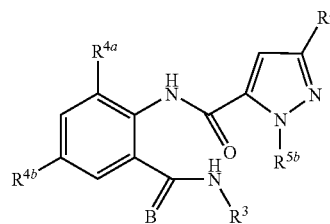

| R⁴ᵃ | R⁴ᵇ | R³ | R⁵ᵃ | R⁵ᵇ |
|---|---|---|---|---|
| Cl | H | Me | OCHF₂ | 3-Cl-2-pyridyl |
| Me | Cl | Me | OCHF₂ | 3-Cl-2-pyridyl |
| Cl | Cl | Me | OCHF₂ | 3-Cl-2-pyridyl |
| Me | Br | Me | OCHF₂ | 3-Cl-2-pyridyl |
| Cl | Br | Me | OCHF₂ | 3-Cl-2-pyridyl |

TABLE 9

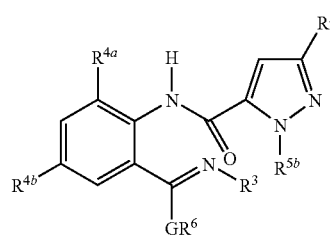

| R⁴ᵃ | R⁴ᵇ | R³ | R⁵ᵃ | R⁵ᵇ |
|---|---|---|---|---|
| GR⁶ is OMe | | | | |
| Me | H | i-Pr | CF₃ | 2-Cl-phenyl |
| Cl | H | i-Pr | CF₃ | 2-Cl-phenyl |
| Me | Cl | i-Pr | CF₃ | 2-Cl-phenyl |
| Cl | Cl | i-Pr | CF₃ | 2-Cl-phenyl |
| Me | Br | i-Pr | CF₃ | 2-Cl-phenyl |
| Cl | Br | i-Pr | CF₃ | 2-Cl-phenyl |
| Me | H | i-Pr | CF₃ | 3-Cl-2-pyridyl |
| Cl | H | i-Pr | CF₃ | 3-Cl-2-pyridyl |
| Me | Cl | i-Pr | CF₃ | 3-Cl-2-pyridyl |
| Cl | Cl | i-Pr | CF₃ | 3-Cl-2-pyridyl |
| Me | Br | i-Pr | CF₃ | 3-Cl-2-pyridyl |
| Cl | Br | i-Pr | CF₃ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF₃ | 2-Cl-phenyl |
| Cl | H | Me | CF₃ | 2-Cl-phenyl |
| Me | Cl | Me | CF₃ | 2-Cl-phenyl |

TABLE 9-continued

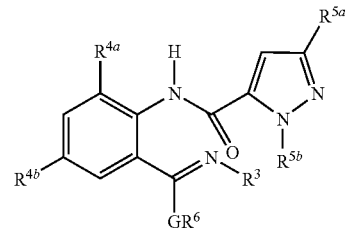

| R⁴ᵃ | R⁴ᵇ | R³ | R⁵ᵃ | R⁵ᵇ |
|---|---|---|---|---|
| Cl | Cl | Me | CF₃ | 2-Cl-phenyl |
| Me | Br | Me | CF₃ | 2-Cl-phenyl |
| Cl | Br | Me | CF₃ | 2-Cl-phenyl |
| Me | H | Me | CF₃ | 3-Cl-2-pyridyl |
| Cl | H | Me | CF₃ | 3-Cl-2-pyridyl |
| Me | Cl | Me | CF₃ | 3-Cl-2-pyridyl |
| Cl | Cl | Me | CF₃ | 3-Cl-2-pyridyl |
| Me | Br | Me | CF₃ | 3-Cl-2-pyridyl |
| Cl | Br | Me | CF₃ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH₂CF₃ | 2-Cl-phenyl |
| Cl | H | i-Pr | OCH₂CF₃ | 2-Cl-phenyl |
| Me | Cl | i-Pr | OCH₂CF₃ | 2-Cl-phenyl |
| Cl | Cl | i-Pr | OCH₂CF₃ | 2-Cl-phenyl |
| Me | Br | i-Pr | OCH₂CF₃ | 2-Cl-phenyl |
| Cl | Br | i-Pr | OCH₂CF₃ | 2-Cl-phenyl |
| Me | H | i-Pr | OCH₂CF₃ | 3-Cl-2-pyridyl |
| Cl | H | i-Pr | OCH₂CF₃ | 3-Cl-2-pyridyl |
| Me | Cl | i-Pr | OCH₂CF₃ | 3-Cl-2-pyridyl |
| Cl | Cl | i-Pr | OCH₂CF₃ | 3-Cl-2-pyridyl |
| Me | Br | i-Pr | OCH₂CF₃ | 3-Cl-2-pyridyl |
| Cl | Br | i-Pr | OCH₂CF₃ | 3-Cl-2-pyridyl |
| Me | H | i-Pr | OCHF₂ | 2-Cl-phenyl |
| Cl | H | i-Pr | OCHF₂ | 2-Cl-phenyl |
| Me | Cl | i-Pr | OCHF₂ | 2-Cl-phenyl |
| Cl | Cl | i-Pr | OCHF₂ | 2-Cl-phenyl |
| Me | Br | i-Pr | OCHF₂ | 2-Cl-phenyl |
| Cl | Br | i-Pr | OCHF₂ | 2-Cl-phenyl |
| Me | H | i-Pr | OCHF₂ | 3-Cl-2-pyridyl |
| Cl | H | i-Pr | OCHF₂ | 3-Cl-2-pyridyl |
| Me | Cl | i-Pr | OCHF₂ | 3-Cl-2-pyridyl |
| Cl | Cl | i-Pr | OCHF₂ | 3-Cl-2-pyridyl |
| Me | Br | i-Pr | OCHF₂ | 3-Cl-2-pyridyl |
| Cl | Br | i-Pr | OCHF₂ | 3-Cl-2-pyridyl |
| Me | H | Me | OCH₂CF₃ | 2-Cl-phenyl |
| Cl | H | Me | OCH₂CF₃ | 2-Cl-phenyl |
| Me | Cl | Me | OCH₂CF₃ | 2-Cl-phenyl |
| Cl | Cl | Me | OCH₂CF₃ | 2-Cl-phenyl |
| Me | Br | Me | OCH₂CF₃ | 2-Cl-phenyl |
| Cl | Br | Me | OCH₂CF₃ | 2-Cl-phenyl |
| Me | H | Me | OCH₂CF₃ | 3-Cl-2-pyridyl |
| Cl | H | Me | OCH₂CF₃ | 3-Cl-2-pyridyl |

TABLE 9-continued

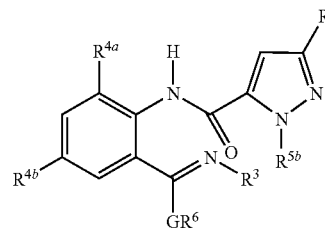

| R4a | R4b | R3 | R5a | R5b |
|---|---|---|---|---|
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |
| GR6 is SMe | | | | |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |

TABLE 9-continued

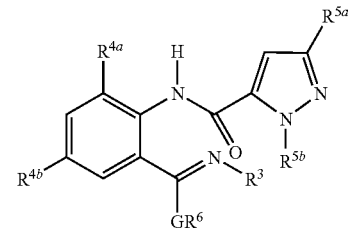

| R4a | R4b | R3 | R5a | R5b |
|---|---|---|---|---|
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |

TABLE 9-continued

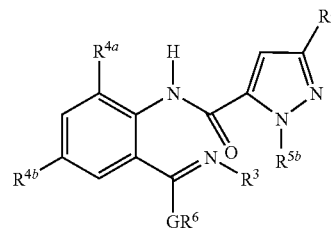

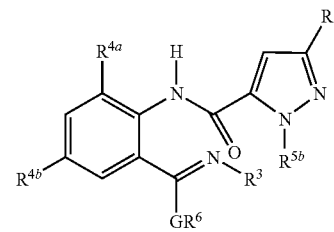

| R4a | R4b | R3 | R5a | R5b |
|---|---|---|---|---|
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |
| GR6 is SCH2Ph | | | | |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | Me | OCH2CF3 | 2-Cl-phenyl |
| Cl | H | Me | OCH2CF3 | 2-Cl-phenyl |
| Me | Cl | Me | OCH2CF3 | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |

TABLE 9-continued

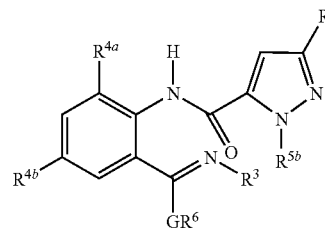

| $R^{4a}$ | $R^{4b}$ | $R^3$ | $R^{5a}$ | $R^{5b}$ |
|---|---|---|---|---|
| | | $GR^6$ is $NMe_2$ | | |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |

TABLE 9-continued

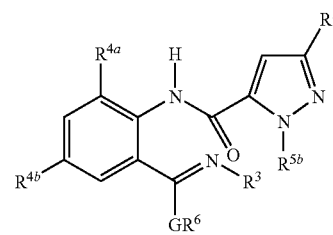

| $R^{4a}$ | $R^{4b}$ | $R^3$ | $R^{5a}$ | $R^{5b}$ |
|---|---|---|---|---|
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |

TABLE 10

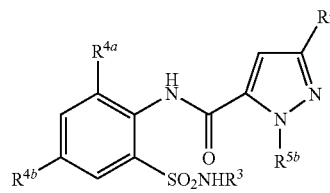

| R4a | R4b | R3 | R5a | R5b |
|---|---|---|---|---|
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |

TABLE 10-continued

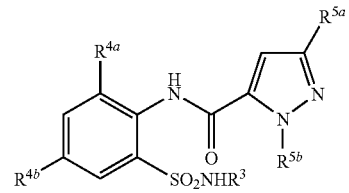

| R4a | R4b | R3 | R5a | R5b |
|---|---|---|---|---|
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | Me | OCH2CF3 | 2-Cl-phenyl |
| Cl | H | Me | OCH2CF3 | 2-Cl-phenyl |
| Me | Cl | Me | OCH2CF3 | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |

TABLE 10-continued

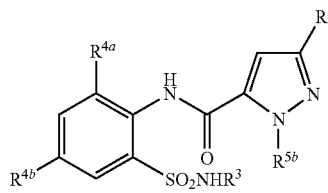

| R4a | R4b | R3 | R5a | R5b |
|---|---|---|---|---|
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |

TABLE 10-continued

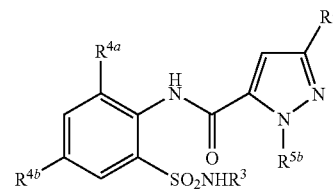

| R4a | R4b | R3 | R5a | R5b |
|---|---|---|---|---|
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |

TABLE 11

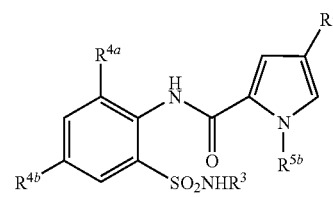

| R4a | R4b | R3 | R5a | R5b |
|---|---|---|---|---|
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |

TABLE 11-continued

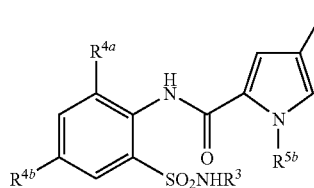

| R4a | R4b | R3 | R5a | R5b |
|---|---|---|---|---|
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |

TABLE 11-continued

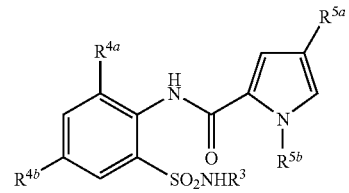

| R4a | R4b | R3 | R5a | R5b |
|---|---|---|---|---|
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |
| Me | Br | i-Pr | OCHF2 | 3-Cl-2-pyridyl |
| Cl | Br | i-Pr | OCHF2 | 3-Cl-2-pyridyl |
| Me | H | Me | OCH2CF3 | 2-Cl-phenyl |
| Cl | H | Me | OCH2CF3 | 2-Cl-phenyl |
| Me | Cl | Me | OCH2CF3 | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |

TABLE 11-continued

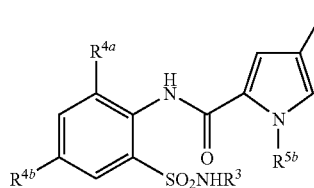

| $R^{4a}$ | $R^{4b}$ | $R^3$ | $R^{5a}$ | $R^{5b}$ |
|---|---|---|---|---|
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |

TABLE 11-continued

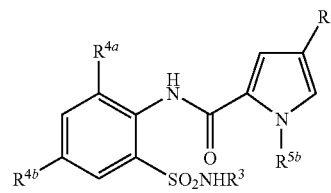

| $R^{4a}$ | $R^{4b}$ | $R^3$ | $R^{5a}$ | $R^{5b}$ |
|---|---|---|---|---|
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |

TABLE 12

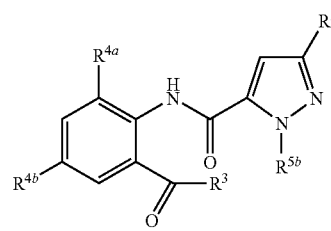

| $R^{4a}$ | $R^{4b}$ | $R^3$ | $R^{5a}$ | $R^{5b}$ |
|---|---|---|---|---|
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |

TABLE 12-continued

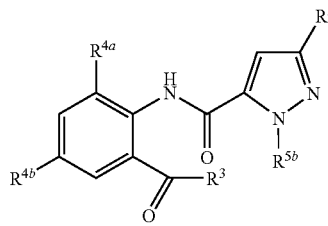

| R4a | R4b | R3 | R5a | R5b |
|---|---|---|---|---|
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |

TABLE 12-continued

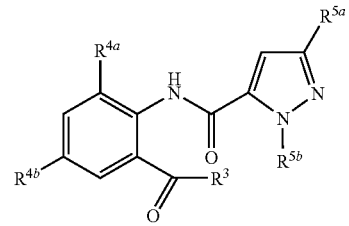

| R4a | R4b | R3 | R5a | R5b |
|---|---|---|---|---|
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |

TABLE 12-continued

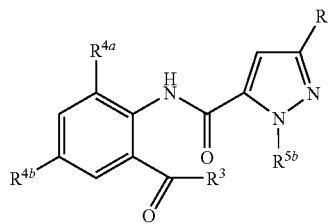

| R4a | R4b | R3 | R5a | R5b |
|---|---|---|---|---|
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | CF3 | 2-Cl-phenyl |
| Cl | H | Me | CF3 | 2-Cl-phenyl |
| Me | Cl | Me | CF3 | 2-Cl-phenyl |
| Cl | Cl | Me | CF3 | 2-Cl-phenyl |
| Me | Br | Me | CF3 | 2-Cl-phenyl |
| Cl | Br | Me | CF3 | 2-Cl-phenyl |
| Me | H | Me | CF3 | 3-Cl-2-pyridyl |
| Cl | H | Me | CF3 | 3-Cl-2-pyridyl |
| Me | Cl | Me | CF3 | 3-Cl-2-pyridyl |
| Cl | Cl | Me | CF3 | 3-Cl-2-pyridyl |
| Me | Br | Me | CF3 | 3-Cl-2-pyridyl |
| Cl | Br | Me | CF3 | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | OCH2CF3 | 2-Cl-phenyl |
| Cl | H | i-Pr | OCH2CF3 | 2-Cl-phenyl |
| Me | Cl | i-Pr | OCH2CF3 | 2-Cl-phenyl |
| Cl | Cl | i-Pr | OCH2CF3 | 2-Cl-phenyl |
| Me | Br | i-Pr | OCH2CF3 | 2-Cl-phenyl |
| Cl | Br | i-Pr | OCH2CF3 | 2-Cl-phenyl |
| Me | H | i-Pr | OCH2CF3 | 3-Cl-2-pyridyl |
| Cl | H | i-Pr | OCH2CF3 | 3-Cl-2-pyridyl |
| Me | Cl | i-Pr | OCH2CF3 | 3-Cl-2-pyridyl |
| Cl | Cl | i-Pr | OCH2CF3 | 3-Cl-2-pyridyl |
| Me | Br | i-Pr | OCH2CF3 | 3-Cl-2-pyridyl |
| Cl | Br | i-Pr | OCH2CF3 | 3-Cl-2-pyridyl |
| Me | H | i-Pr | OCHF2 | 2-Cl-phenyl |
| Cl | H | i-Pr | OCHF2 | 2-Cl-phenyl |
| Me | Cl | i-Pr | OCHF2 | 2-Cl-phenyl |
| Cl | Cl | i-Pr | OCHF2 | 2-Cl-phenyl |
| Me | Br | i-Pr | OCHF2 | 2-Cl-phenyl |
| Cl | Br | i-Pr | OCHF2 | 2-Cl-phenyl |
| Me | H | i-Pr | OCHF2 | 3-Cl-2-pyridyl |
| Cl | H | i-Pr | OCHF2 | 3-Cl-2-pyridyl |
| Me | Cl | i-Pr | OCHF2 | 3-Cl-2-pyridyl |
| Cl | Cl | i-Pr | OCHF2 | 3-Cl-2-pyridyl |

TABLE 12-continued

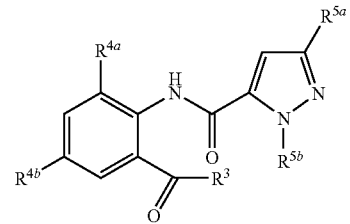

| R4a | R4b | R3 | R5a | R5b |
|---|---|---|---|---|
| Me | Br | i-Pr | OCHF2 | 3-Cl-2-pyridyl |
| Cl | Br | i-Pr | OCHF2 | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | OCH2CF3 | 2-Cl-phenyl |
| Me | Br | Me | OCH2CF3 | 2-Cl-phenyl |
| Cl | Br | Me | OCH2CF3 | 2-Cl-phenyl |
| Me | H | Me | OCH2CF3 | 3-Cl-2-pyridyl |
| Cl | H | Me | OCH2CF3 | 3-Cl-2-pyridyl |
| Me | Cl | Me | OCH2CF3 | 3-Cl-2-pyridyl |
| Cl | Cl | Me | OCH2CF3 | 3-Cl-2-pyridyl |
| Me | Br | Me | OCH2CF3 | 3-Cl-2-pyridyl |
| Cl | Br | Me | OCH2CF3 | 3-Cl-2-pyridyl |
| Me | H | Me | OCHF2 | 2-Cl-phenyl |
| Cl | H | Me | OCHF2 | 2-Cl-phenyl |
| Me | Cl | Me | OCHF2 | 2-Cl-phenyl |
| Cl | Cl | Me | OCHF2 | 2-Cl-phenyl |
| Me | Br | Me | OCHF2 | 2-Cl-phenyl |
| Cl | Br | Me | OCHF2 | 2-Cl-phenyl |
| Me | H | Me | OCHF2 | 3-Cl-2-pyridyl |
| Cl | H | Me | OCHF2 | 3-Cl-2-pyridyl |
| Me | Cl | Me | OCHF2 | 3-Cl-2-pyridyl |
| Cl | Cl | Me | OCHF2 | 3-Cl-2-pyridyl |
| Me | Br | Me | OCHF2 | 3-Cl-2-pyridyl |
| Cl | Br | Me | OCHF2 | 3-Cl-2-pyridyl |

TABLE 13

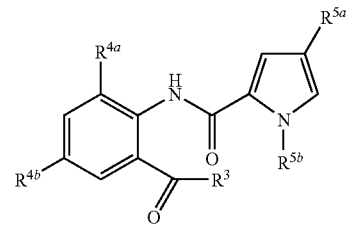

| R4a | R4b | R3 | R5a | R5b |
|---|---|---|---|---|
| Me | H | i-Pr | CF3 | 2-Cl-phenyl |
| Cl | H | i-Pr | CF3 | 2-Cl-phenyl |
| Me | Cl | i-Pr | CF3 | 2-Cl-phenyl |
| Cl | Cl | i-Pr | CF3 | 2-Cl-phenyl |
| Me | Br | i-Pr | CF3 | 2-Cl-phenyl |
| Cl | Br | i-Pr | CF3 | 2-Cl-phenyl |
| Me | H | i-Pr | CF3 | 3-Cl-2-pyridyl |
| Cl | H | i-Pr | CF3 | 3-Cl-2-pyridyl |
| Me | Cl | i-Pr | CF3 | 3-Cl-2-pyridyl |
| Cl | Cl | i-Pr | CF3 | 3-Cl-2-pyridyl |
| Me | Br | i-Pr | CF3 | 3-Cl-2-pyridyl |
| Cl | Br | i-Pr | CF3 | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |

TABLE 13-continued

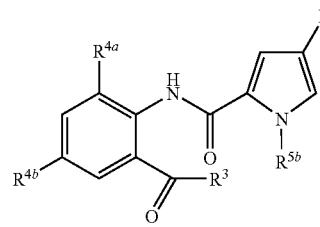

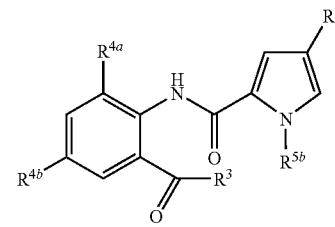

| $R^{4a}$ | $R^{4b}$ | $R^3$ | $R^{5a}$ | $R^{5b}$ |
|---|---|---|---|---|
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |
| Cl | Br | i-Pr | $OCHF_2$ | 3-Cl-2-pyridyl |
| Me | H | Me | $OCH_2CF_3$ | 2-Cl-phenyl |
| Cl | H | Me | $OCH_2CF_3$ | 2-Cl-phenyl |
| Me | Cl | Me | $OCH_2CF_3$ | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |
| Me | H | i-Pr | $CF_3$ | 2-Cl-phenyl |
| Cl | H | i-Pr | $CF_3$ | 2-Cl-phenyl |
| Me | Cl | i-Pr | $CF_3$ | 2-Cl-phenyl |
| Cl | Cl | i-Pr | $CF_3$ | 2-Cl-phenyl |
| Me | Br | i-Pr | $CF_3$ | 2-Cl-phenyl |
| Cl | Br | i-Pr | $CF_3$ | 2-Cl-phenyl |
| Me | H | i-Pr | $CF_3$ | 3-Cl-2-pyridyl |
| Cl | H | i-Pr | $CF_3$ | 3-Cl-2-pyridyl |
| Me | Cl | i-Pr | $CF_3$ | 3-Cl-2-pyridyl |
| Cl | Cl | i-Pr | $CF_3$ | 3-Cl-2-pyridyl |
| Me | Br | i-Pr | $CF_3$ | 3-Cl-2-pyridyl |
| Cl | Br | i-Pr | $CF_3$ | 3-Cl-2-pyridyl |
| Me | H | i-Pr | Br | 2-Cl-phenyl |
| Cl | H | i-Pr | Br | 2-Cl-phenyl |
| Me | Cl | i-Pr | Br | 2-Cl-phenyl |
| Cl | Cl | i-Pr | Br | 2-Cl-phenyl |
| Me | Br | i-Pr | Br | 2-Cl-phenyl |
| Cl | Br | i-Pr | Br | 2-Cl-phenyl |
| Me | H | i-Pr | Br | 3-Cl-2-pyridyl |
| Cl | H | i-Pr | Br | 3-Cl-2-pyridyl |
| Me | Cl | i-Pr | Br | 3-Cl-2-pyridyl |
| Cl | Cl | i-Pr | Br | 3-Cl-2-pyridyl |
| Me | Br | i-Pr | Br | 3-Cl-2-pyridyl |
| Cl | Br | i-Pr | Br | 3-Cl-2-pyridyl |
| Me | H | i-Pr | Cl | 2-Cl-phenyl |
| Cl | H | i-Pr | Cl | 2-Cl-phenyl |
| Me | Cl | i-Pr | Cl | 2-Cl-phenyl |
| Cl | Cl | i-Pr | Cl | 2-Cl-phenyl |
| Me | Br | i-Pr | Cl | 2-Cl-phenyl |
| Cl | Br | i-Pr | Cl | 2-Cl-phenyl |

TABLE 13-continued

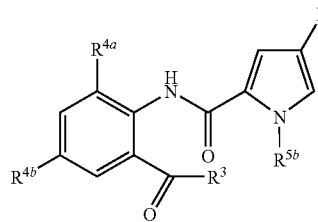

| $R^{4a}$ | $R^{4b}$ | $R^3$ | $R^{5a}$ | $R^{5b}$ |
|---|---|---|---|---|
| Me | H | i-Pr | Cl | 3-Cl-2-pyridyl |
| Cl | H | i-Pr | Cl | 3-Cl-2-pyridyl |
| Me | Cl | i-Pr | Cl | 3-Cl-2-pyridyl |
| Cl | Cl | i-Pr | Cl | 3-Cl-2-pyridyl |
| Me | Br | i-Pr | Cl | 3-Cl-2-pyridyl |
| Cl | Br | i-Pr | Cl | 3-Cl-2-pyridyl |
| Me | H | Me | $CF_3$ | 2-Cl-phenyl |
| Cl | H | Me | $CF_3$ | 2-Cl-phenyl |
| Me | Cl | Me | $CF_3$ | 2-Cl-phenyl |
| Cl | Cl | Me | $CF_3$ | 2-Cl-phenyl |
| Me | Br | Me | $CF_3$ | 2-Cl-phenyl |
| Cl | Br | Me | $CF_3$ | 2-Cl-phenyl |
| Me | H | Me | $CF_3$ | 3-Cl-2-pyridyl |
| Cl | H | Me | $CF_3$ | 3-Cl-2-pyridyl |
| Me | Cl | Me | $CF_3$ | 3-Cl-2-pyridyl |
| Cl | Cl | Me | $CF_3$ | 3-Cl-2-pyridyl |
| Me | Br | Me | $CF_3$ | 3-Cl-2-pyridyl |
| Cl | Br | Me | $CF_3$ | 3-Cl-2-pyridyl |
| Me | H | Me | Br | 2-Cl-phenyl |
| Cl | H | Me | Br | 2-Cl-phenyl |
| Me | Cl | Me | Br | 2-Cl-phenyl |
| Cl | Cl | Me | Br | 2-Cl-phenyl |
| Me | Br | Me | Br | 2-Cl-phenyl |
| Cl | Br | Me | Br | 2-Cl-phenyl |
| Me | H | Me | Br | 3-Cl-2-pyridyl |
| Cl | H | Me | Br | 3-Cl-2-pyridyl |
| Me | Cl | Me | Br | 3-Cl-2-pyridyl |
| Cl | Cl | Me | Br | 3-Cl-2-pyridyl |
| Me | Br | Me | Br | 3-Cl-2-pyridyl |
| Cl | Br | Me | Br | 3-Cl-2-pyridyl |
| Me | H | Me | Cl | 2-Cl-phenyl |
| Cl | H | Me | Cl | 2-Cl-phenyl |
| Me | Cl | Me | Cl | 2-Cl-phenyl |
| Cl | Cl | Me | Cl | 2-Cl-phenyl |
| Me | Br | Me | Cl | 2-Cl-phenyl |
| Cl | Br | Me | Cl | 2-Cl-phenyl |
| Me | H | Me | Cl | 3-Cl-2-pyridyl |
| Cl | H | Me | Cl | 3-Cl-2-pyridyl |
| Me | Cl | Me | Cl | 3-Cl-2-pyridyl |
| Cl | Cl | Me | Cl | 3-Cl-2-pyridyl |
| Me | Br | Me | Cl | 3-Cl-2-pyridyl |
| Cl | Br | Me | Cl | 3-Cl-2-pyridyl |
| Me | H | i-Pr | $OCH_2CF_3$ | 2-Cl-phenyl |
| Cl | H | i-Pr | $OCH_2CF_3$ | 2-Cl-phenyl |
| Me | Cl | i-Pr | $OCH_2CF_3$ | 2-Cl-phenyl |
| Cl | Cl | i-Pr | $OCH_2CF_3$ | 2-Cl-phenyl |
| Me | Br | i-Pr | $OCH_2CF_3$ | 2-Cl-phenyl |
| Cl | Br | i-Pr | $OCH_2CF_3$ | 2-Cl-phenyl |
| Me | H | i-Pr | $OCH_2CF_3$ | 3-Cl-2-pyridyl |
| Cl | H | i-Pr | $OCH_2CF_3$ | 3-Cl-2-pyridyl |
| Me | Cl | i-Pr | $OCH_2CF_3$ | 3-Cl-2-pyridyl |
| Cl | Cl | i-Pr | $OCH_2CF_3$ | 3-Cl-2-pyridyl |
| Me | Br | i-Pr | $OCH_2CF_3$ | 3-Cl-2-pyridyl |
| Cl | Br | i-Pr | $OCH_2CF_3$ | 3-Cl-2-pyridyl |
| Me | H | i-Pr | $OCHF_2$ | 2-Cl-phenyl |
| Cl | H | i-Pr | $OCHF_2$ | 2-Cl-phenyl |
| Me | Cl | i-Pr | $OCHF_2$ | 2-Cl-phenyl |
| Cl | Cl | i-Pr | $OCHF_2$ | 2-Cl-phenyl |
| Me | Br | i-Pr | $OCHF_2$ | 2-Cl-phenyl |
| Cl | Br | i-Pr | $OCHF_2$ | 2-Cl-phenyl |
| Me | H | i-Pr | $OCHF_2$ | 3-Cl-2-pyridyl |
| Cl | H | i-Pr | $OCHF_2$ | 3-Cl-2-pyridyl |
| Me | Cl | i-Pr | $OCHF_2$ | 3-Cl-2-pyridyl |
| Cl | Cl | i-Pr | $OCHF_2$ | 3-Cl-2-pyridyl |
| Me | Br | i-Pr | $OCHF_2$ | 3-Cl-2-pyridyl |

TABLE 13-continued

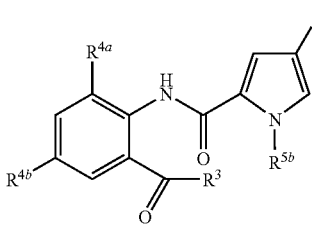

| $R^{4a}$ | $R^{4b}$ | $R^3$ | $R^{5a}$ | $R^{5b}$ |
|---|---|---|---|---|
| Cl | Br | i-Pr | $OCHF_2$ | 3-Cl-2-pyridyl |
| Me | H | i-Pr | Me | 2-Cl-phenyl |
| Cl | H | i-Pr | Me | 2-Cl-phenyl |
| Me | Cl | i-Pr | Me | 2-Cl-phenyl |
| Cl | Cl | Me | $OCH_2CF_3$ | 2-Cl-phenyl |
| Me | Br | Me | $OCH_2CF_3$ | 2-Cl-phenyl |
| Cl | Br | Me | $OCH_2CF_3$ | 2-Cl-phenyl |
| Me | H | Me | $OCH_2CF_3$ | 3-Cl-2-pyridyl |
| Cl | H | Me | $OCH_2CF_3$ | 3-Cl-2-pyridyl |
| Me | Cl | Me | $OCH_2CF_3$ | 3-Cl-2-pyridyl |
| Cl | Cl | Me | $OCH_2CF_3$ | 3-Cl-2-pyridyl |
| Me | Br | Me | $OCH_2CF_3$ | 3-Cl-2-pyridyl |
| Cl | Br | Me | $OCH_2CF_3$ | 3-Cl-2-pyridyl |
| Me | H | Me | $OCHF_2$ | 2-Cl-phenyl |
| Cl | H | Me | $OCHF_2$ | 2-Cl-phenyl |
| Me | Cl | Me | $OCHF_2$ | 2-Cl-phenyl |
| Cl | Cl | Me | $OCHF_2$ | 2-Cl-phenyl |
| Me | Br | Me | $OCHF_2$ | 2-Cl-phenyl |
| Cl | Br | Me | $OCHF_2$ | 2-Cl-phenyl |
| Me | H | Me | $OCHF_2$ | 3-Cl-2-pyridyl |
| Cl | H | Me | $OCHF_2$ | 3-Cl-2-pyridyl |
| Me | Cl | Me | $OCHF_2$ | 3-Cl-2-pyridyl |
| Cl | Cl | Me | $OCHF_2$ | 3-Cl-2-pyridyl |
| Me | Br | Me | $OCHF_2$ | 3-Cl-2-pyridyl |
| Cl | Br | Me | $OCHF_2$ | 3-Cl-2-pyridyl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, N.Y., 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexalnone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147-48, *Perry's Chemical Engineer's Handbook,* 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge,* T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 1041; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science,* John Wiley and Sons, Inc., New York, 1961, pp 81-96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

Example A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
| --- | --- |
| Compound 1 | 10.0% |
| attapulgite granules (low volatile matter, 0.71/0.30 mm; U.S.S. No. 25-50 sieves) | 90.0%. |

Example C

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
| --- | --- |
| Compound 1 | 20.0% |
| blend of oil soluble sulfonates and polyoxyethylene ethers | 10.0% |
| isophorone | 70.0%. |

Example E

| Granule | |
|---|---|
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Huflagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panoychus ulmi* Koch), two spotted spider mite (*Tetraychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, Ad. differentialis Thomas), American grasshoppers (e.g., *Schistocerca americana* Drury), desert locust (*Schistocerca gregaria* Forskal), migratory locust (*Locusta migratoria* Liimaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagous ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis genlinata* Fabricius), red imported fire ant (*Solenopsis invicta* Buren), Argentine ant (*Iridomyrnex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctemocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scuttigera coleoptrata* Linnaeus). Compounds of the present invention also have activity on members of the Classes Nernatoda, Cestoda, Trematoda, and Acanthocephala including economically important members of the orders Strongylida, Ascaridida, Oxyurida, Rhabditida, Spilurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., bama argillacea Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm). *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Limiaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall almyworm), *Trichoplusia ni* Hübner (cabbage looper) and *Tutta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawvberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis gramimum* Rondani (greenbug), *Sitobion avenzae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorim* Westwood (greenhouse whitefly); *Emipoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stal (rice leafhopper), *Nilaparvata lugens* Stal (brown planthopper), *Pereginus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecin* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato-bug), *Dysdercus suturellus* Herrich-Schaffer (cotton stainer), *Euchistus selvus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax*. Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemzlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetaniprid, avelmectin, azadirachtin, azinphosmethyl, bifenthrin, binfenazate, buprofezin, carbofuran, chlorfenapyr, chlorfluazuron, chlorpyrifos, chlorpyrifos-methyl, chromafenozide, clothianidin, cyflutluin, beta-cyfluthrin, cyhalothrin, lambda-cyhalothrin, cypermethrin, cyromazine, deltainethlin, diafenthiuron, diazinon, difluben-zuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyrfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxifen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captani, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neoasozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of exogenously applied invertebrate pest control compounds of this invention may be synergistic with the expressed toxin proteins.

A general reference for these agricultural protectants is *The Pesticide Manual, 12th Edition*, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound or agent is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A and B for compound descriptions. The following abbreviations are used in the Index Tables that follow: "Me" means methyl, "i" means iso, "Pr" means propyl and i-Pr means isopropyl. The abbreviation "Ex." stands for "Example" and is followed by a number indicating in which example the compound is prepared.

INDEX TABLE A

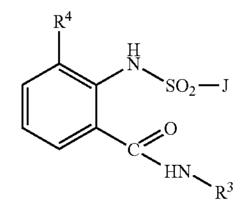

| Compound | $R^4$ | $R^3$ | J | m.p. ° C. |
|---|---|---|---|---|
| 1 | Me | i-Pr | 4-Cl-phenyl | 208-210 |
| 2 (Ex. 2) | Me | i-Pr | 1-(3-Cl-2-pyridinyl)-3-$CF_3$-5-pyrazolyl | 69-72 |

INDEX TABLE B

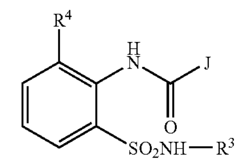

| Compound | $R^4$ | $R^3$ | J | m.p. ° C. |
|---|---|---|---|---|
| B1 | Me | i-Pr | 4-$CF_3$-phenyl | 139-142 |
| B2 (Ex. 1) | Me | i-Pr | 4-$OCF_3$-phenyl | 104-107 |
| B3 | Me | i-Pr | 1-(3-Cl-2-pyridinyl)-3-$CF_3$-5-pyrazolyl | 69-73 |

INDEX TABLE C

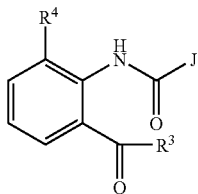

| Compound | R⁴ | R³ | J | m.p. ° C. |
|---|---|---|---|---|
| C1 | Me | i-Bu | 1-(3-Cl-2-pyridinyl)-3-CF₃-5-pyrazolyl | 138-140 |
| C2 (Ex. 3) | Me | i-Bu | 1-(3-Cl-2-pyridinyl)-3-Br-5-pyrazolyl | 119-120 |
| C3 | Me | Et | 1-(3-Cl-2-pyridinyl)-3-Br-5-pyrazolyl | 185-186 |
| C4 | Me | Me | 1-(3-Cl-2-pyridinyl)-3-Br-5-pyrazolyl | 133-135 |
| C5 | Me | Me | 1-(3-Cl-2-pyridinyl)-3-CF₃-5-pyrazolyl | 113-114 |
| C6 | Me | i-Pr | 1-(3-Cl-2-pyridinyl)-3-Br-5-pyrazolyl | 102-104 |
| C7 | Me | i-Pr | 1-(3-Cl-2-pyridinyl)-3-CF₃-5-pyrazolyl | 124-125 |

INDEX TABLE D

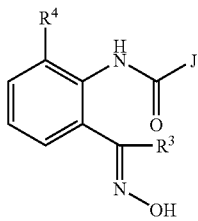

| Compound | R⁴ | R³ | J | m.p. ° C. |
|---|---|---|---|---|
| D1 | Me | Et | 1-(3-Cl-2-pyridinyl)-3-Br-5-pyrazolyl | 152-154 |
| D2 | Me | Me | 1-(3-Cl-2-pyridinyl)-3-Br-5-pyrazolyl | 181-182 |

BIOLOGICAL EXAMPLES OF THE INVENTION

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® (D Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm (or lower) and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (20% or less feeding damage): 1*, B3*, C2**, C5* and C6*.

Test B

For evaluating control of fall armyworm (*Spodoptera frugiperda*) the test unit consisted of a small open container with a 45-day-old corn (maize) plant inside. This was pre-infested with 10-15 1-day-old larvae on a piece of insect diet by use of a core sampler as described for Test A.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided excellent levels of plant protection (20% or less feeding damage): C2* and C5*.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 250 ppm (or lower) as described for Test A. The applications were replicated three times. After spraying, the test units were maintained in a growth chamber and then visually rated as described for Test A.

Of the compounds tested, the following provided excellent levels of plant protection (20% or less feeding damage): C2* and C6*.

*Tested at 50 ppm.
**Tested at 10 ppm.

The invention claimed is:

1. A compound of Formula 2, an N-oxide or a salt thereof

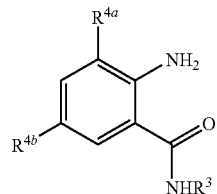

wherein
R³ is i-propyl or methyl;
R⁴ᵃ is methyl or Cl;
R⁴ᵇ is H, Cl or Br;
provided that
(a) when R⁴ᵃ is methyl and R⁴ᵇ is H, then R³ is not i-propyl; and
(b) when R⁴ᵃ is Cl, then R⁴ᵇ is Br.

2. The compound of claim 1 wherein R³ is methyl, R⁴ᵃ is methyl and R⁴ᵇ is H.

3. The compound of claim 1 wherein R³ is methyl, R⁴ᵃ is methyl and R⁴ᵇ is Cl.

* * * * *